US010660928B2

(12) United States Patent
Kim et al.

(10) Patent No.: US 10,660,928 B2
(45) Date of Patent: May 26, 2020

(54) PHARMACEUTICAL COMPOSITION CONTAINING COMBINATION EXTRACTS OF MOUTAN ROOT BARK, ANGELICA DAHURICA ROOT, BUPLEURUM ROOT OR FRACTIONS THEREOF FOR PREVENTION AND TREATMENT OF NEURODEGENERATIVE DISORDER

(71) Applicants: UNIVERSITY-INDUSTRY COOPERATION GROUP OF KYUNG HEE UNIVERSITY, Yongin-si, Gyeonggi-do (KR); DONG-A ST CO., LTD., Seoul (KR)

(72) Inventors: Youngmi Kim, Seoul (KR); Myung Sook Oh, Seoul (KR); Seon-Pyo Hong, Seoul (KR); Mi Won Sohn, Yongin-si (KR); Jin Seok Jeong, Seoul (KR); Hai Hua Jiang, Yongin-si (KR); Eunjin Kim, Seoul (KR); Ja Young Ryu, Seoul (KR); Young Woong Cho, Suwon-si (KR); Xiao Fei Du, Yongin-si (KR); Sang Zin Choi, Suwon-si (KR); Jeong Soo Kim, Yongin-si (KR); Byoung Moon Kim, Seoul (KR)

(73) Assignees: UNIVERSITY-INDUSTRY COOPERATION GROUP OF KYUNG HEE UNIVERSITY, Yongin-si (KR); DONG-A ST CO., LTD., Seoul (KR)

( * ) Notice: Subject to any disclaimer, the term of this patent is extended or adjusted under 35 U.S.C. 154(b) by 382 days.

(21) Appl. No.: 15/453,511

(22) Filed: Mar. 8, 2017

(65) Prior Publication Data
US 2017/0224754 A1 Aug. 10, 2017

Related U.S. Application Data

(63) Continuation of application No. PCT/KR2015/009717, filed on Sep. 16, 2015.

(30) Foreign Application Priority Data

Sep. 19, 2014 (KR) .................. 10-2014-0124860
Sep. 15, 2015 (KR) .................. 10-2015-0130107

(51) Int. Cl.
*A61K 36/65* (2006.01)
*A61K 36/232* (2006.01)
(Continued)

(52) U.S. Cl.
CPC ............ *A61K 36/65* (2013.01); *A21D 13/047* (2017.01); *A21D 13/40* (2017.01); *A23L 2/52* (2013.01); *A23L 7/109* (2016.08); *A23L 13/422* (2016.08); *A23L 23/10* (2016.08); *A23L 33/10* (2016.08); *A61K 9/0019* (2013.01); *A61K 9/0056* (2013.01); *A61K 9/0095* (2013.01); *A61K 9/08* (2013.01); *A61K 9/14* (2013.01); *A61K 9/20* (2013.01); *A61K 9/48* (2013.01); *A61K 31/12* (2013.01); *A61K 31/352* (2013.01); *A61K 31/357* (2013.01); *A61K 31/7048* (2013.01); *A61K 36/232* (2013.01); *A61K 36/233* (2013.01); *A23V 2002/00* (2013.01);
(Continued)

(58) Field of Classification Search
CPC combination set(s) only.
See application file for complete search history.

(56) References Cited

U.S. PATENT DOCUMENTS

2004/0185128 A1 9/2004 Kim et al.
2009/0226482 A1* 9/2009 Chan ............... A61K 36/00
424/195.15

FOREIGN PATENT DOCUMENTS

CN 101461899 A * 6/2009
JP 2005501018 A 1/2005
(Continued)

OTHER PUBLICATIONS

YaNan Gai, el al., Analysis of the traditional medicine YiGan San by the fragmentation patterns of cadambine indole alkaloids using HPLC coupled with high-resolution MS, J. Sep. Sci., Dec. 2, 2013, vol. 36, pp. 3723-3732.

(Continued)

*Primary Examiner* — Amy L Clark
(74) *Attorney, Agent, or Firm* — Lucas & Mercanti, LLP

(57) ABSTRACT

The present invention relates to a pharmaceutical composition for treating and preventing degenerative neurological disorders, containing, as an active ingredient, a mixture extract of two or more types selected from the group consisting of Moutan Root Bark, Angelica Dahurica Root, and Bupleurum Root, or a fraction thereof. Specifically, the extract of the mixture of the present invention exhibits a recovery effect on mitochondrial function damage, a relieving effect on endoplasmic reticulum stress and also exhibits simultaneously an inhibitory effect on inflammatory response, which are remarkably improved compared with those exhibited in an in vitro single extract, and the extract of the mixture significantly exhibits an improvement effect on motor coordination and a protective effect on dopaminergic neurons in a Parkinson's disease animal model, and thus the extract of the mixture of the present invention or a fraction thereof can be useful as an active ingredient of a pharmaceutical composition for treating and preventing degenerative neurological disorders.

6 Claims, 4 Drawing Sheets
Specification includes a Sequence Listing.

(51) Int. Cl.

| | | |
|---|---|---|
| A61K 36/233 | (2006.01) | |
| A23L 33/10 | (2016.01) | |
| A23L 23/10 | (2016.01) | |
| A23L 13/40 | (2016.01) | |
| A23L 7/109 | (2016.01) | |
| A21D 13/40 | (2017.01) | |
| A21D 13/047 | (2017.01) | |
| A23L 2/52 | (2006.01) | |
| A61K 9/00 | (2006.01) | |
| A61K 9/08 | (2006.01) | |
| A61K 9/14 | (2006.01) | |
| A61K 9/20 | (2006.01) | |
| A61K 9/48 | (2006.01) | |
| A61K 31/12 | (2006.01) | |
| A61K 31/352 | (2006.01) | |
| A61K 31/357 | (2006.01) | |
| A61K 31/7048 | (2006.01) | |

(52) U.S. Cl.
CPC .... *A61K 2236/333* (2013.01); *A61K 2236/51* (2013.01); *A61K 2236/53* (2013.01)

(56) References Cited

FOREIGN PATENT DOCUMENTS

| JP | 2011-037722 A | 2/2011 |
|---|---|---|
| KR | 20020092147 A | 12/2002 |
| KR | 20050047779 A | 5/2005 |
| KR | 20100060279 A | 6/2010 |
| KR | 20110125706 A | 11/2011 |

OTHER PUBLICATIONS

Epifano F, et. al., Natural coumarins as a novel class of neuroprotective agents., Mini Rev Med Chem. Oct. 9, 2009(11):pp. 1262-1271.
Lin B, Polyphenols and neuroprotection against ischemia and neurodegeneration., Mini Rev Med Chem. Dec. 2011;11(14):1222-38.
European Supplementary Search Report, European Application No. 15842648.6-1466, dated Jun. 26, 2017.
YaNan Gai, el al., Analysis of the traditional medicine YiGan San by the fragmentation patterns of cadambine indole alkaloids using HPLC coupled with high-resolution MS, J. Sep. Sci. 2013, 36, 3723-3732.
Epifano F, et. al., Natural coumarins as a novel class of neuroprotective agents., Mini Rev Med Chem. Oct. 2009;9(11):1262-71.
H.G. Kim, et. al; Effects of the root bark of Paeonia suffruticosa on mitochondria-mediated neuroprotection in an MPTP-induced model of Parkinson's disease; Food and Chemical Toxicology; vol. 65; 2014; pps 293-300.
S.-H. Huang, et. al; Protective effects of Angelica sinensis extract on amyloid β-peptide-induced neurotoxicity; Phytomedicine; vol. 15; 2008; pp. 710-721.
International Search Report for PCT/KR2015/009717 dated Dec. 22, 2015.
Buysse, "Insomnia", JAMA, 2013, vol. 309, No. 7, pp. 706-716.
Stacy, "Nonmotor Symptoms in Parkinson's Disease", International Journal of Neuroscience, 2011, vol. 121, pp. 9-17.
Martinez-Martin, "Prevalence of Nonmotor Symptoms in Parkinson's Disease in an International Setting; Study Using Nonmotor Symptoms Questionnaire in 545 Patients", Movement Disorders, 2007, vol. 22, No. 11, pp. 1623-1629.

* cited by examiner

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: COX III forward primer, synthesized

<400> SEQUENCE: 1
caatgatggc gcgatgtaac                                          20

<210> SEQ ID NO 2
<211> LENGTH: 20
<212> TYPE: DNA
<213> ORGANISM: Artificial Sequence
<220> FEATURE:
<223> OTHER INFORMATION: COX III reverse primer, synthesized

<400> SEQUENCE: 2
ggtgattgat actcctgatg                                          20

<210> SEQ ID NO 3
<211> LENGTH: 20
<212> TYPE: DNA
<213> ORGANISM: Artificial Sequence
<220> FEATURE:
<223> OTHER INFORMATION: PARK7 forward primer, synthesized

<400> SEQUENCE: 3
cgagctggga ttaaggtcac                                          20

<210> SEQ ID NO 4
<211> LENGTH: 20
```

```
<212> TYPE: DNA
<213> ORGANISM: Artificial Sequence
<220> FEATURE:
<223> OTHER INFORMATION: PARK7 reverse primer, synthesized

<400> SEQUENCE: 4
ttcatgagcc aacagagcag                                              20

<210> SEQ ID NO 5
<211> LENGTH: 21
<212> TYPE: DNA
<213> ORGANISM: Artificial Sequence
<220> FEATURE:
<223> OTHER INFORMATION: GRP78 forward primer, synthesized

<400> SEQUENCE: 5
gagatcatcg ccaacgatca g                                            21

<210> SEQ ID NO 6
<211> LENGTH: 21
<212> TYPE: DNA
<213> ORGANISM: Artificial Sequence
<220> FEATURE:
<223> OTHER INFORMATION: GRP78 reverse primer, synthesized

<400> SEQUENCE: 6
acttgatgtc ctgctgcaca g                                            21

<210> SEQ ID NO 7
<211> LENGTH: 22
<212> TYPE: DNA
<213> ORGANISM: Artificial Sequence
<220> FEATURE:
<223> OTHER INFORMATION: XBP1p forward primer, synthesized

<400> SEQUENCE: 7
ggtctgctga gtccgcagca gg                                           22

<210> SEQ ID NO 8
<211> LENGTH: 19
<212> TYPE: DNA
<213> ORGANISM: Artificial Sequence
<220> FEATURE:
<223> OTHER INFORMATION: XBP1p reverse primer, synthesized

<400> SEQUENCE: 8
gggcttggta tatatgtgg                                               19

<210> SEQ ID NO 9
<211> LENGTH: 20
<212> TYPE: DNA
<213> ORGANISM: Artificial Sequence
<220> FEATURE:
<223> OTHER INFORMATION: iNOS forward primer, synthesized

<400> SEQUENCE: 9
cctggaggtt ctggatgaga                                              20

<210> SEQ ID NO 10
<211> LENGTH: 20
<212> TYPE: DNA
<213> ORGANISM: Artificial Sequence
<220> FEATURE:
<223> OTHER INFORMATION: iNOS reverse primer, synthesized

<400> SEQUENCE: 10
```

```
gtagtagcgg ggcttcaaga                                              20

<210> SEQ ID NO 11
<211> LENGTH: 24
<212> TYPE: DNA
<213> ORGANISM: Artificial Sequence
<220> FEATURE:
<223> OTHER INFORMATION: IL-6 forward primer, synthesized

<400> SEQUENCE: 11
ctggagtacc atagctacct ggag                                         24

<210> SEQ ID NO 12
<211> LENGTH: 22
<212> TYPE: DNA
<213> ORGANISM: Artificial Sequence
<220> FEATURE:
<223> OTHER INFORMATION: IL-6 reverse primer, synthesized

<400> SEQUENCE: 12
gtccttagcc actccttctg tg                                           22

<210> SEQ ID NO 13
<211> LENGTH: 22
<212> TYPE: DNA
<213> ORGANISM: Artificial Sequence
<220> FEATURE:
<223> OTHER INFORMATION: p65/RELA forward primer, synthesized

<400> SEQUENCE: 13
gaccaacaat aaccccttc ac                                            22

<210> SEQ ID NO 14
<211> LENGTH: 21
<212> TYPE: DNA
<213> ORGANISM: Artificial Sequence
<220> FEATURE:
<223> OTHER INFORMATION: p65/RELA reverse primer, synthesized

<400> SEQUENCE: 14
gtttgagatc tgccctgatg g                                            21

<210> SEQ ID NO 15
<211> LENGTH: 20
<212> TYPE: DNA
<213> ORGANISM: Artificial Sequence
<220> FEATURE:
<223> OTHER INFORMATION: 18s rRNA forward primer, synthesized

<400> SEQUENCE: 15
gagcgaaagc atttgccaag                                              20

<210> SEQ ID NO 16
<211> LENGTH: 20
<212> TYPE: DNA
<213> ORGANISM: Artificial Sequence
<220> FEATURE:
<223> OTHER INFORMATION: 18s rRNA reverse primer, synthesized

<400> SEQUENCE: 16
ggcatcgttt atggtcggaa                                              20
```

PHARMACEUTICAL COMPOSITION CONTAINING COMBINATION EXTRACTS OF MOUTAN ROOT BARK, ANGELICA DAHURICA ROOT, BUPLEURUM ROOT OR FRACTIONS THEREOF FOR PREVENTION AND TREATMENT OF NEURODEGENERATIVE DISORDER

CROSS-REFERENCE TO RELATED APPLICATIONS

This application is a continuation of PCT/KR2015/009717, filed Sep. 16, 2015, which claims the benefit of Korean Patent Application No. 10-2014-0124860, filed Sep. 19, 2014 and of Korean Patent Application No. 10-2015-0130107, filed Sep. 15, 2015, the contents of each of which are incorporated herein by reference.

BACKGROUND OF THE INVENTION

Field of the Invention

The present invention relates to a pharmaceutical composition for treating and preventing degenerative neurological disorders containing a mixture extract of two or more types selected from the group consisting of Moutan Root Bark (Moutan Radicis Cortex), Angelica Dahurica Root (Angelicae Dahuricae Radix) and Bupleurum Root (Bupleuri Radix) or a fraction thereof as an active ingredient.

Description of the Related Art

Over the past two decades, patients with degenerative neurological disorders have been increased rapidly in the world. In the treatment of degenerative neurological disorder, the most important step is the prevention. However, the cause of the disease has not been clearly understood yet and thus a treatment method is still needed to be studied. The common pathological phenomenon of degenerative neurological disorders is the death of central nervous system cells. Unlike other organ cells, central nervous system cells are almost impossible to regenerate after cell-death, resulting in permanent loss of function. The methods for the treatment of such brain diseases developed so far are mainly focused on the analysis of the death mechanism of nerve cells themselves and the prevention of the death based on the analysis. According to the results of recent basic and clinical studies on Alzheimer's disease and Parkinson's disease, inflammatory reaction in the brain is a major cause of neuronal death. In reality, the increase of inflammation mediators and reactive oxygen has been confirmed in the cerebrospinal fluid of brain disease patients. Also, numbers of active microglial cells are observed in the area of brain damage, indicating brain inflammation is a major cause of Parkinson's disease. Therefore, inhibition of brain inflammation by neuroglial cells has become a target of treating degenerative neurological disorder. However, therapeutic agents that have been developed so far are only effective in regulating the symptoms of the disease but are not effective in treating degenerative neurological disorder itself. Many environmental pollutants that are constantly exposed in modern society and the mutation of genes resulting from the pollutants cause degenerative neurological disorder. Therefore it is required to develop a preventive and therapeutic agent for degenerative neurological disorder based on the totally different concept from the conventional ones.

Degenerative neurological disorder includes Alzheimer's disease, Parkinson's disease, stroke, Huntington's disease, and spinal cord injury, etc. Among those diseases, Parkinson's disease is the second most common degenerative neurological disorder that affects 1~2% of Koreans aged over 60 and 4~5% of Koreans aged over 85. Parkinson's disease is rapidly increasing in Korea's middle-aged people in their 40~50 s recently. In a previous report, Parkinson's disease seemed to be induced by the lack of dopamine resulted from the death of dopaminergic neurons in the substantia nigra and corpus striatum in the midbrain. The reason of the selective death of dopaminergic neurons has not been explained, yet. Accordingly, an effective treating agent and a diagnostic reagent have not been developed, yet. Parkinson's disease displays such symptoms as expressionless face, rigidity, tremor, curved posture, and bradykinesia.

It has been recently proposed that malfunctioning of mitochondria might be a cause of various neurodegenerative diseases including Parkinson's disease. As the causing genes of familial Parkinson's disease (Familial PD), genes involved in the generation of reactive oxygen species (ROS) and proteolysis such as PARK1/4 (α-synuclein), PARK2 (parkin), PARK6 (PTEN-induced putative kinase 1, PINK1), PARK7 (DJ-1), and PARK8 (leucine-rich repeat kinase 2, LRRK2) existing in the outer membrane of mitochondria, and PARK13 (HTRA2/0MI) existing in the inner membrane of mitochondria were identified (Nat. Clin. Pract. Neurol 2, 136-146, 2006). PINKI, parkin, and DJ-1 are involved in such actions in mitochondrial dynamics as fission and fusion to support the network structure of mitochondria (PLoS Biol. 6, e1000298, 2010).

Sporadic Parkinson's disease (sporadic PD) taking 95% of all Parkinson's disease is also characterized by mitochondrial activity impairment. Insecticides/herbicides such as paraquat and rotenone are known as a causing material to damage the activity of mitochondria by suppressing electron transport system of mitochondria. MPTP (1-methyl-4-phenyl-1,2,3,6-tetrahydropyridine) used to establish Parkinson's disease animal model and its metabolite MPP+ are known as the selective inhibitors of mitochondria electron transport system complex 1. This example suggests that the selective death of dopaminergic neurons due to mitochondrial dysfunction may be a cause of Parkinson's disease and at the same time the recovery of mitochondrial activity may be an important target for the treatment of Parkinson's disease Endoplasmic reticulum, an intracellular organelle, is classified into rough endoplasmic reticulum (rough ER, RER) with ribosomes attached and smooth endoplasmic reticulum (smooth ER, SER). The major function of rough endoplasmic reticulum is protein synthesis. Approximately ⅓ of intracellular proteins are synthesized in rough endoplasmic reticulum. In the meantime, various lipids and steroid hormones are synthesized in smooth endoplasmic reticulum. Smooth ER also plays an important role in regulating intracellular calcium concentration. However, abnormal folding of proteins due to various reasons causes functional damage of endoplasmic reticulum, which is called endoplasmic reticulum stress. When endoplasmic reticulum stress continues, apoptosis and massive reactive oxygen species (ROS) formation are increased through various signal transductions, resulting in cell damage. It has also been reported that endoplasmic reticulum stress is also a cause of degenerative neurological disorders such as Alzheimer's disease, Parkinson's disease, stroke, Huntington's disease, and spinal cord injury along with metabolic syndrome, diabetes mellitus, obesity, and dyslipidemia mediated by the damage of mitochondria (Lindholm et al., 2006; Penas et al., 2007; Yoshida, 2007; Zhang et al., 2006).

Moutan Root Bark (Moutan Radicis Cortex) is the root bark of *Paeonia suffruticosa* Andrews, which is an herb medicine containing paeonol, paeoniflorin, oxypaeoniflorin, and garlic acid or paeoniflorigenone. In Oriental medicine, it is known that Moutan Root Bark is effective in relaxation, pain-killing, anti-inflammation, and treating inflammatory disease thereby. Recently, Moutan Root Bark has been known to have antimicrobial, anti-inflammatory, antioxidant, and anti-aging activities, and its efficacy of treating brain disease as a component of various mixtures has been reported.

Angelica Dahurica Root (Angelicae dahuricae Radix) is the dried root of Angelica dahurica Bentham et Hooker f. or Angelica dahurica Bentham et Hooker f. var. formosana Shan et Yuan which is a 2~3 year old herb that is native in Korea, China, and Japan. The major bioactive compounds of Angelica Dahurica Root are imperatorin, isoimperatorin, oxypeucedanin, phellopterin, and byakangelicol. In Oriental medicine, various effects of Angelica Dahurica Root have been known. In particular, it is known to be effective in alleviating sweating, sedation, pain, cold, headache or toothache. However, there is no report on the involvement of Angelica Dahurica Root in the improvement of mitochondrial functions and relief of endoplasmic reticulum stress so as to improve neuronal disease treating effect.

Bupleurum Root (Bupleuri Radix) is a medicinal herb that refers to the root of Bupleurum falcatum Linne or its variants (Umbelliferae).

The main pharmacological activities of Bupleurum Root include various pharmacological activities such as antipyretic, soothing, analgesic, antibacterial, antiviral and anti-inflammatory activities. The major pharmacological activities of Bupleurum Root are antipyretic, soothing, analgesic, antibacterial, antiviral and anti-inflammatory activities.

The present inventors tried to develop a therapeutic agent for degenerative neurological disorder from edible herbs. As a result, the inventors found out that the extract of the mixture of two or more types selected from the group consisting of Moutan root bark, Angelica dahurica root and Bupleurum root had the activity to recover the functional damage of mitochondria, to relieve endoplasmic reticulum stress, and to inhibit inflammatory response simultaneously, which was significantly higher than that of each single extract showed. The extract of the mixture above significantly improved motor coordination and showed protective effect on dopaminergic neurons in vivo in Parkinson's disease model, so that the present inventors confirmed that the extract of the mixture of Moutan root bark, Angelica dahurica root and Bupleurum root or the fraction thereof could be useful as an active ingredient of a pharmaceutical composition for treating and preventing degenerative neurological disorders, leading to the completion of the invention.

SUMMARY OF THE INVENTION

It is an object of the present invention to provide a pharmaceutical composition for treating or preventing degenerative neurological disorders comprising an extract of a mixture of two or more selected from the group consisting of Moutan Root Bark (Moutan Radicis Cortex), Angelica Dahurica Root (Angelicae Dahuricae Radix) and Bupleurum Root (Bupleuri Radix) or a fraction thereof as an active ingredient, and a health functional food for improving or preventing degenerative neurological disorders comprising the same.

To achieve the above object, the present invention provides a pharmaceutical composition for treating or preventing degenerative neurological disorders comprising an extract of a mixture of two or more selected from the group consisting of Moutan Root Bark (Moutan Radicis Cortex), Angelica Dahurica Root (Angelicae Dahuricae Radix) and Bupleurum Root (Bupleuri Radix) as an active ingredient.

The present invention also provides a pharmaceutical composition for treating or preventing degenerative neurological disorders comprising an organic solvent fraction of the extract of the mixture above as an active ingredient.

The present invention also provides a health functional food for improving or preventing degenerative neurological disorders comprising an extract of a mixture of two or more selected from the group consisting of Moutan Root Bark, Angelica Dahurica Root and Bupleurum Root as an active ingredient.

The present invention also provides a health functional food for improving or preventing degenerative neurological disorders comprising an organic solvent fraction of the extract of the mixture above as an active ingredient.

The present invention also provides a method for treating or preventing degenerative neurological disorders comprising the step of administering a pharmaceutically effective dose of an extract of a mixture of two or more selected from the group consisting of Moutan Root Bark (Moutan Radicis Cortex), Angelica Dahurica Root (Angelicae Dahuricae Radix) and Bupleurum Root (Bupleuri Radix) to a subject.

The present invention also provides a pharmaceutical composition comprising an extract of a mixture of two or more selected from the group consisting of Moutan Root Bark (Moutan Radicis Cortex), Angelica Dahurica Root (Angelicae Dahuricae Radix) and Bupleurum Root (Bupleuri Radix), for use in treating or preventing degenerative neurological disorders.

The present invention also provides a method for treating or preventing degenerative neurological disorders comprising the step of administering a pharmaceutically effective dose of an organic solvent fraction of the extract of the mixture of two or more selected from the group consisting of Moutan Root Bark, Angelica Dahurica Root and Bupleurum Root to a subject.

In addition, the present invention provides a pharmaceutical composition comprising an organic solvent fraction of the extract of the mixture of two or more selected from the group consisting of Moutan Root Bark, Angelica Dahurica Root and Bupleurum Root, for use in treating or preventing degenerative neurological disorders.

Advantageous Effect

The extract of the mixture of two or more types selected from the group consisting of Moutan Root Bark (Moutan Radicis Cortex), Angelica Dahurica Root (Angelicae Dahuricae Radix) and Bupleurum Root (Bupleuri Radix) could increase the intracellular ATP level, recover the damaged mitochondrial membrane potential; and suppress the ROS generation as strongly as 1.5 times the single extract when mitochondria functional damage, endoplasmic reticulum stress, and inflammation response were induced simultaneously in Parkinson's disease model. The extract of the mixture of the present invention was also confirmed to be significantly effective in improving motor coordination and protecting dopaminergic neurons in Parkinson's disease animal model, so that the extract of the mixture of the invention or the fraction thereof can be effectively used as an active ingredient of a pharmaceutical composition for the prevention and treatment of degenerative neurological disorder.

BRIEF DESCRIPTION OF THE DRAWINGS

The application of the preferred embodiments of the present invention is best understood with reference to the accompanying drawings, wherein.

DETAILED DESCRIPTION OF THE INVENTION

Figure 1:
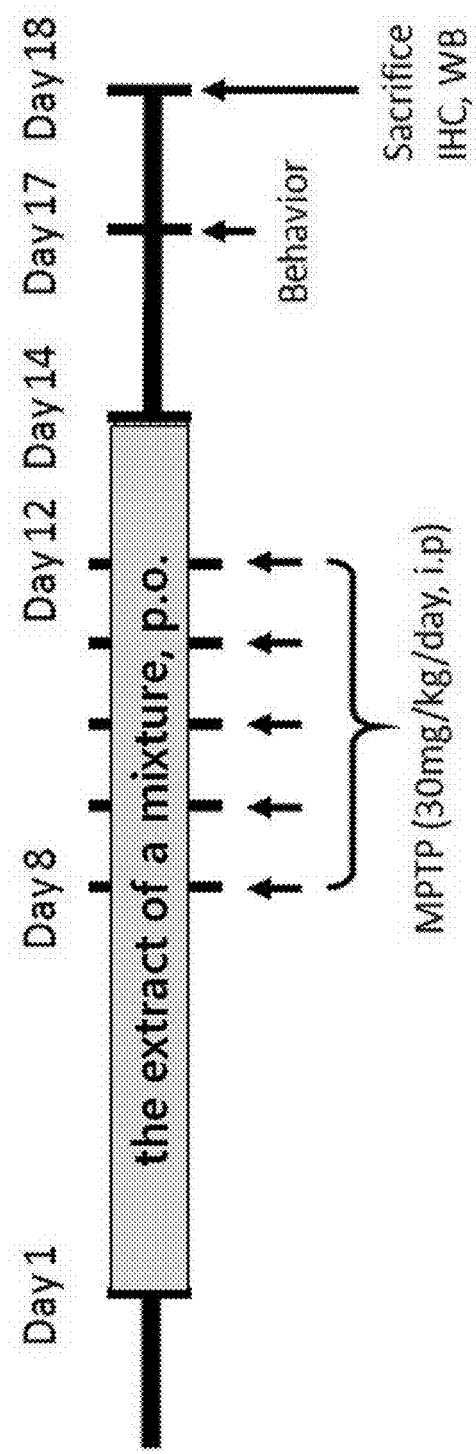
FIG. 1 is a schematic diagram illustrating the process of the construction of Parkinson's disease animal model through the 1-methyl-4-phenyl-1,2,3,6-tetrahydropyridine (MPTP) administration. Particularly, the freeze-dried 90% ethanol extract of a mixture composed of Moutan Root Bark, Angelica Dahurica Root and Bupleurum Root at the ratio of 1:1:1 was dissolved in 3% HPMC, which was administered (per oral, p.o.) to the test mouse (1, 3, or 10 mg/kg), once a day for 14 days. From the 8th day of the experiment, 1-methyl-4-phenyl-1,2,3,6-tetrahydropyridine (MPTP) was administered (intraperitoneal, i.p.) to the mouse at the dose of 30 mg/kg three hours after the oral administration for 5 days, resulting in the construction of Parkinson's disease animal model. The prepared mouse model was used for behavioral test. The animal was sacrificed and cell analysis and western blotting were performed.

Hereinafter, the present invention is described in detail.

The present invention provides a pharmaceutical composition for treating or preventing degenerative neurological disorders comprising an extract of a mixture of two or more selected from the group consisting of Moutan Root Bark (Moutan Radicis Cortex), Angelica Dahurica Root (Angelicae Dahuricae Radix) and Bupleurum Root (Bupleuri Radix) as an active ingredient.

The present invention also provides a pharmaceutical composition for treating or preventing degenerative neurological disorders comprising an organic solvent fraction of the extract of the mixture of two or more selected from the group consisting of Moutan Root Bark, Angelica Dahurica Root and Bupleurum Root as an active ingredient.

It is preferred to mix Moutan Root Bark, Angelica Dahurica Root and Bupleurum Root at the weight ratio of 1:0.2~5:0.2~5 (w:w:w). More preferably Moutan Root Bark, Angelica Dahurica Root and Bupleurum Root are mixed at the ratio of 1:0.5~2:0.5~2 (w:w:w), and most preferably at the ratio of 1:1:1 (w:w:w), but not always limited thereto.

Two materials selected from the group consisting of Moutan Root Bark, Angelica Dahurica Root and Bupleurum Root are preferably mixed at the weight ratio of 1:0.2~5 (w:w), more preferably at the ratio of 1:0.5~2 (w:w), and most preferably at the ratio of 1:1 (w:w), but not always limited thereto.

The extract of the mixture above is preferably extracted by using water, $C_1$~$C_4$ lower alcohol, or a mixture thereof as a solvent, and at this time the lower alcohol is preferably ethanol, methanol, or butanol.

The extract of the mixture is preferably extracted from the mixture composed of at least two materials selected from the group consisting of Moutan Root Bark, Angelica Dahurica Root and Bupleurum Root, but can be extracted from the mixture composed of at least two extracts among each Moutan Root Bark, Angelica Dahurica Root and Bupleurum Root extract.

The extract of the mixture above is preferably prepared by the method comprising the following steps, but not always limited thereto:

1) adding an extraction solvent to the mixture composed of at least two of those materials selected from the group consisting of Moutan Root Bark, Angelica Dahurica Root and Bupleurum Root, followed by extraction;

2) filtering the extract of step 1); and 3) concentrating the filtrate obtained in step 2) under reduced pressure, followed by drying thereof.

In the method above, the Moutan Root Bark, Angelica Dahurica Root and Bupleurum Root of step 1) are either purchased or cultivated.

In the method above, the method for the extraction of the extract is any of those conventional methods such as filtration, hot-water extraction, enfleurage, reflux extraction, and ultrasonic extraction.

In this method, the concentration under reduced pressure in step 3) is preferably performed by using a vacuum concentrator or a vacuum rotary evaporator, but not always limited thereto. Drying herein is preferably performed by reduced-pressurized drying, vacuum drying, boiling drying, spray drying, or freeze drying, but not always limited thereto.

The said fraction is preferably prepared from the extract by adding an organic solvent. The organic solvent herein is preferably one or more solvents selected from the group consisting of hexane, chloroform, ethyl acetate, and butanol, and more preferably butanol, but not always limited thereto.

The said extract preferably contains one or more compounds selected from the group consisting of paeonol (2'-Hydroxy-4'-methoxyacetophenone) represented by formula 1, paeoniflorin represented by formula 2, paeoniflorigenone ([(2s,3as,5s,7ar,8s)-3a-hydroxy-7a-methyl-6-oxohexahydro-2,5-methano-1,3-benzodioxol-8-yl]methyl benzoate) represented by formula 3, imperatorin (9-[(3-Methyl-2-buten-1-yl)oxy]-7h-furo[3,2-g][1]benzopyran-7-one) represented by formula 4, saikosaponin A ((3beta,4alpha,16beta)-13,28-Epoxy-16,23-dihydroxyolean-11-en-3-yl-6-deoxy-3-O-beta-D-glucopyranosyl-beta-D-galactopyranoside) represented by formula 5, saikosaponin B2 ((3b,4a,16a)-16,23,28-Trihydroxyoleana-11,13(18)-dien-3-yl-6-deoxy-3-O-beta-D-glucopyranosyl-beta-D-galactopyranoside) represented by formula 6, saikosaponin B4 ((3β,11α,16α)-16,23,28-Trihydroxy-11-methoxyolean-12-en-3-yl-6-deoxy-3-O-β-D-glucopyranosyl-β-D-galactopyranoside) represented by formula 7, and saikosaponin D ((3b,4a,16a)-13,28-Epoxy-16,23-dihydroxyolean-11-en-3-yl 6-deoxy-3-O-beta-D-glucopyranosyl beta-D-galactopyranoside) represented by formula 8, but not always limited thereto:

[Formula 1]

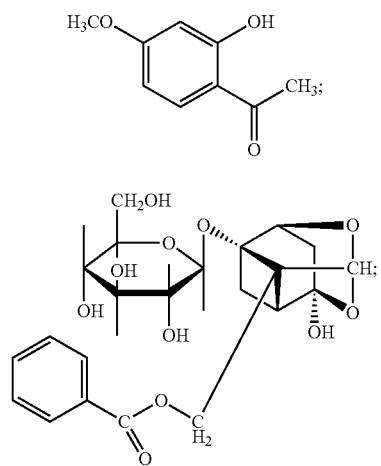

[Formula 2]

[Formula 3]

[Formula 4]

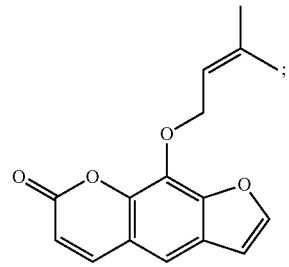

[Formula 5]

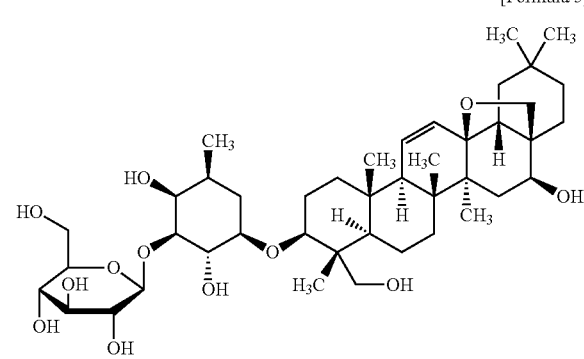

[Formula 6]

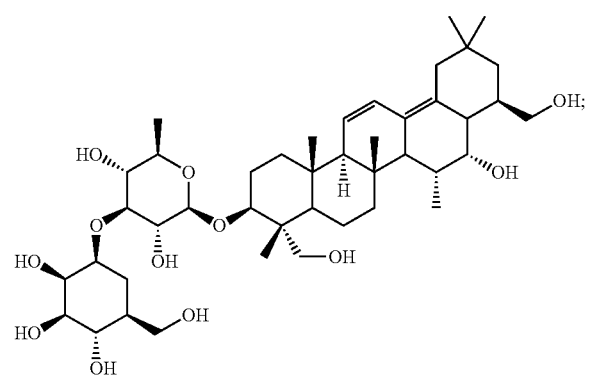

[Formula 7]

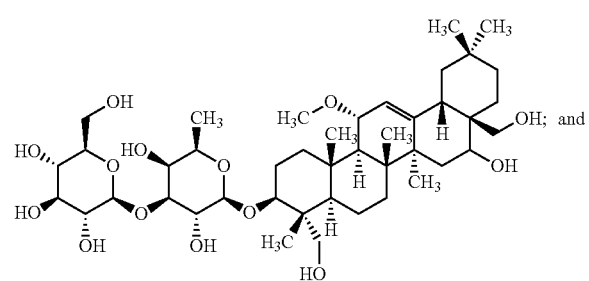

-continued

[Formula 8]

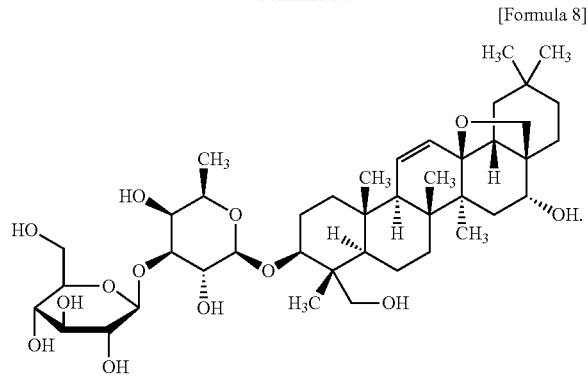

The extract above preferably inhibits mitochondria functional damage, endoplasmic reticulum stress, or inflammatory response, but not always limited thereto.

The degenerative neurological disorder herein is preferably selected from the group consisting of dementia, Huntington's disease, Parkinson's disease, Alzheimer's disease, stroke, Lou Gehrig's disease (amyotrophic lateral sclerosis), and spinal cord injury, but not always limited thereto.

In a preferred embodiment of the present invention, the present inventors investigated the recovery of neuronal cells having induced functional damage in order to confirm the effect of the single extract of Moutan Root Bark, Angelica Dahurica Root, or Bupleurum Root.

As a result, it was confirmed that the single extract of Moutan Root Bark had the recovery effect on functional damage of mitochondria (see Tables 2~7), while the single extract of Angelica Dahurica Root had the recovery effect on endoplasmic reticulum stress (see Tables 8~13). It was also confirmed that the single extract of Bupleurum Root had the recovery effect of inflammation (see Tables 14~20).

The extract of the mixture composed of at least two of those materials selected from the group consisting of Moutan Root Bark, Angelica Dahurica Root and Bupleurum Root according to the present invention demonstrated the ATP level recovery effect and suppressed the generation of reactive oxygen species in Parkinson's disease cell model. In particular, the extract of the mixture of Moutan Root Bark, Angelica Dahurica Root and Bupleurum Root demonstrated the significant recovery effect on functional damage of mitochondria (see Tables 21~24).

The present inventors also investigated the recovery effect of the extract of the mixture of Moutan Root Bark, Angelica Dahurica Root and Bupleurum Root on cell function in Parkinson's disease cell model according to the mixing ratio. As a result, when those herb materials were mixed at the ratio of 1:1:1 (w:w:w), the cell function recovery effect was most efficient (see Tables 24~26). The inventors also investigated the recovery effect of the mixed ethanol extract of Moutan Root Bark, Angelica Dahurica Root and Bupleurum Root on cell function in Parkinson's disease cell model according to the concentration of ethanol. As a result, when the extract of the mixture extracted by using 90% ethanol was treated, the combined cell function recovery effect was most significantly increased (see Tables 28~30). The ethanol extract could increase the recovery effect most significantly, compared with the water extract, methanol extract, and butanol extract (see Tables 31~33).

To confirm the effect of the mixed 90% ethanol extract prepared from the mixture of Moutan Root Bark, Angelica Dahurica Root and Bupleurum Root at the ratio of 1:1:1 (w:w:w), the recovery effect was investigated in the neuronal cell line induced with cell function damage. As a result, it was confirmed that the extract of the mixture exhibited the recovery effect on functional damage of mitochondria, endoplasmic reticulum stress, and inflammation (see Tables 34~38).

In addition, the Parkinson's disease animal models constructed by using 1-methyl-4-phenyl-1,2,3,6-tetrahydropyridine (MPTP), 6-hydroxydopamine (6-OHDA), Rotenone, and (lipopolysaccharide) LPS) were used in order to confirm the therapeutic effect of the extract of the mixture of Moutan Root Bark, Angelica Dahurica Root and Bupleurum Root on Parkinson's disease in vivo. The extract of the mixture was administered to the Parkinson's disease mouse model constructed by the treatment of MPTP, followed by behavioral test. As a result, motor coordination was improved in the Parkinson's disease model, compared with the animal model not treated with the extract of the mixture of the invention. The extract of the mixture of the invention also confirmed to have a protective effect on dopaminergic neurons and a recovery effect on signal transduction system damage in striatum (ST), substantia nigra (SN) and cerebellum (see Tables 39~47). Behavioral test was also performed with the Parkinson's disease mouse model constructed by the treatment of 6-OHDA. As a result, the extract of the mixture of the invention confirmed to have an improvement effect on motor coordination and a protective effect on dopaminergic neurons in striatum and substantia nigra (see Tables 48~52). Behavioral test was also performed with the Parkinson's disease mouse model constructed by the treatment of Rotenone. As a result, the motor function suppressed by rotenone was improved and the accumulation of α-synuclein-oligomer, the major pathogenic factor of Parkinson's disease, was reduced in substantia nigra (see Tables 53~54). In the meantime, in the neuroinflammation mouse model constructed by the administration of LPS, the activation of microglia and astrocytes induced in substantia nigra and hippocampus was inhibited by the extract of the mixture of Moutan Root Bark, Angelica Dahurica Root and Bupleurum Root, suggesting that anti-inflammation effect was shown in there (see Tables 55~58).

The extract of the mixture of Moutan Root Bark, Angelica Dahurica Root and Bupleurum Root of the present invention exhibits a recovery effect on mitochondrial function damage, a relieving effect on endoplasmic reticulum stress and also exhibits simultaneously an inhibitory effect on inflammatory response, which are remarkably improved compared with those exhibited in an in vitro single extract, and the extract of the mixture significantly exhibits an improvement effect on motor coordination and a protective effect on dopaminergic neurons in a Parkinson's disease animal model, and thus the extract of the mixture of the present invention or a fraction thereof can be useful as an active ingredient of a pharmaceutical composition for treating and preventing degenerative neurological disorders.

The composition of the present invention can be administered orally or parenterally and be used in general forms of pharmaceutical formulation. That is, the composition of the present invention can be prepared for oral or parenteral administration by mixing with generally used diluents or excipients such as fillers, extenders, binders, wetting agents, disintegrating agents and surfactants.

Solid formulations for oral administration are tablets, pills, powders, granules and capsules. These solid formulations are prepared by mixing the said betaine with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The composition of the present invention can be administered orally or parenterally and the parenteral administration is preferably exemplified by external skin application, intraperitoneal injection, intrarectal injection, intravenous injection, intramuscular injection, subcutaneous injection, intrauterine injection, and intracerebroventricular injection. Among them, external skin application is more preferred.

The composition of the present invention is preferably administered at a pharmaceutically effective dose. The term "pharmaceutically effective dose" herein indicates the amount enough to treat the disease with applicable, reasonable or risky concentration. The dose can be determined by considering many factors such as the type of disease, severity of the disease, activity of the drug, sensitivity to the drug, administration frequency and pathway, excretion, term of treatment, co-treatment drug and other factors regarded as relevant in the medicinal field. The composition of the present invention can be administered alone or together with other drugs. If co-treatment is needed, the administration could be performed stepwise or simultaneously. The composition can be administered singly or multiply. It is important to take into account all of the above factors and to administer the amount in which the maximum effect can be obtained in the minimum amount without side effects, which can be easily determined by those in the art.

The effective dose of the compound of the present invention can be determined according to weight, age, gender, health condition, diet, administration frequency, administration method, excretion and severity of a disease. The dosage is 0.01~1000 mg/kg per day, preferably 30~500 mg/kg per day, and more preferably 50~300 mg/kg per day, and administration frequency is preferably 1~6 times a day. However, the effective dose can be increased or decreased according to the administration pathway, severity of obesity, gender, body weight, and age of patient, etc, so that the effective dose above cannot limit the present invention in any aspects.

The composition of the present invention can be administered alone or treated together with surgical operation, hormone therapy, chemo-therapy and biological regulators.

The present invention also provides a health functional food for improving or preventing degenerative neurological disorders comprising an extract of a mixture of two or more selected from the group consisting of Moutan Root Bark, Angelica Dahurica Root and Bupleurum Root as an active ingredient.

The present invention also provides a health functional food for improving or preventing degenerative neurological disorders comprising an organic solvent fraction of the extract of the mixture of two or more selected from the group consisting of Moutan Root Bark, Angelica Dahurica Root and Bupleurum Root as an active ingredient.

It is preferred to mix Moutan Root Bark, Angelica Dahurica Root and Bupleurum Root at the weight ratio of 1:0.2~5:0.2~5 (w:w:w). More preferably Moutan Root Bark, Angelica Dahurica Root and Bupleurum Root are mixed at the ratio of 1:0.5~2:0.5~2 (w:w:w), and most preferably at the ratio of 1:1:1 (w:w:w), but not always limited thereto.

Two materials selected from the group consisting of Moutan Root Bark, Angelica Dahurica Root and Bupleurum Root are preferably mixed at the weight ratio of 1:0.2~5 (w:w), more preferably at the ratio of 1:0.5~2 (w:w), and most preferably at the ratio of 1:1 (w:w), but not always limited thereto.

The extract of the mixture above is preferably extracted by using water, $C_1$~$C_4$ lower alcohol, or a mixture thereof as a solvent, and at this time the lower alcohol is preferably ethanol, methanol, or butanol.

The extract of the mixture is preferably extracted from the mixture composed of at least two materials selected from the group consisting of Moutan Root Bark, Angelica Dahurica Root and Bupleurum Root, but can be extracted from the mixture composed of at least two extracts among each Moutan Root Bark, Angelica Dahurica Root and Bupleurum Root extract.

The said mixture extract preferably contains one or more compounds selected from the group consisting of paeonol represented by formula 1, paeoniflorin represented by formula 2, paeoniflorigenone represented by formula 3, imperatorin represented by formula 4, saikosaponin A represented by formula 5, saikosaponin B2 represented by formula 6, saikosaponin B4 represented by formula 7, and saikosaponin D represented by formula 8, but not always limited thereto The extract of the mixture above preferably inhibits mitochondria functional damage, endoplasmic reticulum stress, and inflammatory response, but not always limited thereto.

The degenerative neurological disorder herein is preferably selected from the group consisting of dementia, Huntington's disease, Parkinson's disease, Alzheimer's disease, stroke, Lou Gehrig's disease (amyotrophic lateral sclerosis), and spinal cord injury, and Parkinson's disease is more preferred, but not always limited thereto. The extract of the mixture of Moutan Root Bark, Angelica Dahurica Root and Bupleurum Root of the present invention exhibits a recovery effect on mitochondrial function damage, a relieving effect on endoplasmic reticulum stress and also exhibits simultaneously an inhibitory effect on inflammatory response, which are remarkably improved compared with those exhibited in an in vitro single extract, and the extract of the mixture significantly exhibits an improvement effect on motor coordination and a protective effect on dopaminergic neurons in a Parkinson's disease animal model, and thus the extract of the mixture of the present invention or a fraction thereof can be useful as an active ingredient of a health functional food for improving and preventing degenerative neurological disorders.

The present invention also provides a method for treating or preventing degenerative neurological disorders comprising the step of administering a pharmaceutically effective dose of an extract of a mixture of two or more selected from the group consisting of Moutan Root Bark (Moutan Radicis Cortex), Angelica Dahurica Root (Angelicae Dahuricae Radix) and Bupleurum Root (Bupleuri Radix) to a subject.

The present invention also provides a pharmaceutical composition comprising an extract of a mixture of two or more selected from the group consisting of Moutan Root Bark (Moutan Radicis Cortex), Angelica Dahurica Root (Angelicae Dahuricae Radix) and Bupleurum Root (Bupleuri Radix), for use in treating or preventing degenerative neurological disorders.

The present invention also provides a method for treating or preventing degenerative neurological disorders comprising the step of administering a pharmaceutically effective dose of an organic solvent fraction of the extract of the mixture of two or more selected from the group consisting of Moutan Root Bark, Angelica Dahurica Root and Bupleurum Root to a subject.

In addition, the present invention provides a pharmaceutical composition comprising an organic solvent fraction of the extract of the mixture of two or more selected from the group consisting of Moutan Root Bark, Angelica Dahurica Root and Bupleurum Root, for use in treating or preventing degenerative neurological disorders.

The extract of the mixture of Moutan Root Bark, Angelica Dahurica Root and Bupleurum Root of the present invention exhibits a recovery effect on mitochondrial function damage, a relieving effect on endoplasmic reticulum stress and also exhibits simultaneously an inhibitory effect on inflammatory response, which are remarkably improved compared with those exhibited in an in vitro single extract, and the extract of the mixture significantly exhibits an improvement effect on motor coordination, a protective effect on dopaminergic neurons, and an anti-inflammatory effect in a Parkinson's disease animal model, and thus the extract of the mixture of the present invention or a fraction thereof can be useful as an active ingredient of a pharmaceutical composition for treating and preventing degenerative neurological disorders.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Single Extract of Each Moutan Root Bark, Angelica Dahurica Root and Bupleurum Root <1-1> Preparation of Moutan Root Bark Ethanol Extract 90% ethanol was added to Moutan Root Bark (Moutan Radicis Cortex; Jeungdo Herb Medicine Co., Korea), followed by extraction at room temperature for 110 minutes. An ethanol extract was prepared by filtering the extract. The obtained extract was freeze-dried and stored. At the time of use, the extract was dissolved in a buffer. As an index component of the extract, paeonol was used to confirm the purity.

<1-2> Preparation of Angelica Dahurica Root Ethanol Extract

90% ethanol was added to Angelica Dahurica Root (Angelicae Dahuricae Radix; Jeungdo Herb Medicine Co., Korea). An ethanol extract of Angelica Dahurica Root was prepared by the same manner as described in Example <1-1>. As an index component of the Angelica Dahurica Root extract, Imperatorin was used to confirm the purity.

<1-3> Preparation of Bupleurum Root Ethanol Extract

90% ethanol was added to Bupleurum Root (Bupleuri Radix; Jeungdo Herb Medicine Co., Korea). An ethanol extract of Bupleurum Root was prepared by the same manner as described in Example <1-1>. As an index component of the Bupleurum Root extract, saikosaponin A was used to confirm the purity.

Example 2: Preparation of Mixture Extract of Moutan Root Bark and Angelica Dahurica Root Moutan Root Bark and Angelica Dahurica Root were mixed at the ratio of 1:5, 1:1 or 1:0.2 (w:w), to which 90% ethanol was added, followed by extraction at room temperature for 110 minutes. A mixed ethanol extract of Moutan Root Bark and Angelica Dahurica Root was prepared by filtering the extract. The obtained mixed ethanol extract was freeze-dried and stored. At the time of use, the extract was dissolved in water or a buffer. As index components of the mixture extract, paeonol and imperatorin were used to confirm the purity.

Example 3: Preparation of Mixture Extract of Moutan Root Bark and Bupleurum Root Moutan Root Bark and Bupleurum Root were mixed at the ratio of 1:5, 1:1 or 1:0.2 (w:w), to which 90% ethanol was added, followed by extraction at room temperature for 110 minutes. A mixed ethanol extract of Moutan Root Bark and Bupleurum Root was prepared by filtering the extract. The obtained mixed ethanol extract was freeze-dried and stored. At the time of use, the extract was dissolved in a buffer. As index components of the mixture extract, paeonol and saikosaponin A were used to confirm the purity.

Example 4: Preparation of Mixture Extract of Angelica Dahurica Root and Bupleurum Root Angelica Dahurica Root and Bupleurum Root were mixed at the ratio of 1:5, 1:1 or 1:0.2 (w:w), to which 90% ethanol was added, followed by extraction at room temperature for 110 minutes. A mixed ethanol extract of Angelica Dahurica Root and Bupleurum Root was prepared by filtering the extract. The obtained mixed ethanol extract was freeze-dried and stored. At the time of use, the extract was dissolved in a buffer. As index components of the mixture extract, Imperatorin and saikosaponin A were used to confirm the purity.

Example 5: Preparation of Mixture Extract of Moutan Root Bark, Angelica Dahurica Root and Bupleurum Root <5-1> Preparation of Mixed Ethanol Extract of Moutan Root Bark, Angelica Dahurica Root and Bupleurum Root Moutan Root Bark, Angelica Dahurica Root and Bupleurum Root were mixed at the ratio shown in Table 1 below, to which 10, 30, 50, 70, or 90% ethanol was added, followed by extraction at room temperature for 110 minutes. A mixed ethanol extract of Moutan Root Bark, Angelica Dahurica Root and Bupleurum Root was prepared by filtering the extract. The obtained mixed ethanol extract was freeze-dried and stored. At the time of use, the extract was dissolved in a buffer. As index components of the mixture extract, paeonol, saikosaponin A and imperatorin were used to confirm the purity.

TABLE 1

Mixing ratio of Moutan Root Bark, *Angelica Dahurica* Root and *Bupleurum* Root

| | Mixing ratio (%, w:w:w) | | |
|---|---|---|---|
| No. | Moutan Root Bark | *Angelica Dahurica* Root | *Bupleurum* Root |
| 1 | 1 | 2 | 1 |
| 2 | 1 | 1 | 2 |
| 3 | 1 | 2 | 2 |
| 4 | 1 | 0.5 | 1 |
| 5 | 1 | 1 | 0.5 |
| 6 | 1 | 0.5 | 0.5 |
| 7 | 1 | 3 | 1 |
| 8 | 1 | 1 | 3 |
| 9 | 1 | 3 | 3 |
| 10 | 1 | 0.33 | 1 |
| 11 | 1 | 1 | 0.33 |
| 12 | 1 | 0.33 | 0.33 |
| 13 | 1 | 4 | 1 |
| 14 | 1 | 1 | 4 |
| 15 | 1 | 4 | 4 |
| 16 | 1 | 0.25 | 1 |
| 17 | 1 | 1 | 0.25 |
| 18 | 1 | 0.25 | 0.25 |
| 19 | 1 | 5 | 1 |
| 20 | 1 | 1 | 5 |
| 21 | 1 | 5 | 5 |
| 22 | 1 | 0.2 | 1 |
| 23 | 1 | 1 | 0.2 |
| 24 | 1 | 0.2 | 0.2 |
| 25 | 1 | 1 | 1 |

<5-2> Preparation of Mixed Water Extract of Moutan Root Bark, Angelica Dahurica Root and Bupleurum Root Moutan Root Bark, Angelica Dahurica Root and Bupleurum Root were mixed at the ratio of 1:1:1 (w:w:w), to which water was added. A mixed water extract of Moutan Root Bark, Angelica Dahurica Root and Bupleurum Root was prepared by the same manner as described in Example <5-1>.

<5-3> Preparation of Mixed Methanol Extract of Moutan Root Bark, Angelica Dahurica Root and Bupleurum Root Moutan Root Bark, Angelica Dahurica Root and Bupleurum Root were mixed at the ratio of 1:1:1 (w:w:w), to which 90% methanol was added. A mixed methanol extract of Moutan Root Bark, Angelica Dahurica Root and Bupleurum Root was prepared by the same manner as described in Example <5-1>.

<5-4> Preparation of Mixed Butanol Extract of Moutan Root Bark, Angelica Dahurica Root and Bupleurum Root Moutan Root Bark, Angelica Dahurica Root and Bupleurum Root were mixed at the ratio of 1:1:1 (w:w:w), to which 90% butanol was added. A mixed butanol extract of Moutan Root Bark, Angelica Dahurica Root and Bupleurum Root was prepared by the same manner as described in Example <5-1>.

Experimental Example 1: Evaluation of Intracellular Efficacy of Moutan Root Bark Extract and its Active Component <1-1> Effect of Moutan Root Bark Extract and its Active Component on Cell Survival Rate To evaluate the intracellular efficacy of the Moutan Root Bark extract of the present invention and its active component, cytotoxicity in human neuroblastoma cells was investigated.

Particularly, SH-SY5Y, the human neuroblastoma cell line, was inoculated in DMEM/F12 (Dulbeco's Modified Eagle's Medium & Ham's F12; Gibco, USA) supplemented with 10% FBS, followed by culture in a 37° C., 5% $CO_2$/95% air ($O_2$) incubator. Then, the cultured cells were transferred into a serum free medium at the density of $2.5 \times 10^4$ cells/well. The cells were treated with the Moutan Root Bark extract prepared in Example <1-1> or its active component, paeonol, paeoniflorin or paeoniflorigenone at the concentration of 1.0 μg/ml for 4 hours. The cells were collected and the cell survival rate was measured by using calcein. The survival rate of the cells that were increased or decreased compared with that of the normal control cells not-treated with the extract or its active component above and instead treated with DMSO was calculated and presented as percentage (%).

As a result, as shown in Table 2 below, the Moutan Root Bark extract and its active component did not show cytotoxicity in normal cells (Table 2).

TABLE 2

Effect of Moutan Root Bark extract and its active component on cell survival rate

| Treatment substance | | Conc. (μg/ml) | Cell survival rate (% of control) |
|---|---|---|---|
| Normal control group | | — | 100.0 ± 7.35 |
| Moutan Root Bark extract and active ingredient | 90% ethanol extract | 1 | 105.4 ± 6.83 |
| | Paeonol | 1 | 102.2 ± 9.10 |
| | paeoniflorin | 1 | 97.9 ± 7.34 |
| | paeoniflorigenone | 1 | 98.9 ± 8.10 |

<1-2> Inhibitory Effect of Moutan Root Bark Extract and its Active Component on Cell Death Induced by Mitochondrial Damage To investigate the effect of the Moutan Root Bark extract and its active ingredient on the recovery of the mitochondrial functional damage, MTT assay was performed to confirm the recovery effect on the damage of mitochondria complex 1 in cells.

Particularly, SH-SY5Y, the human neuroblastoma cell line, was inoculated in DMEM/F12 (1:1, Dulbeco's Modified Eagle's Medium & Ham's F12; Gibco, USA) supplemented with 10% FBS, followed by culture in a 37° C., 5% $CO_2$/95% air ($O_2$) incubator. Then, the cultured cells were transferred into a serum free medium at the density of $1 \times 10^5$ cells/well. The cells were treated with the Moutan Root Bark 90% ethanol extract prepared in Example <1-1> or its active component, paeonol, paeoniflorin or paeoniflorigenone at the concentration of 1.0 μg/ml, followed by culture for 4 hours. The cells were then treated with 50 μg/ml of atrazine (2-chloro-4-(ethylamine)-6-(isopropylamine)-s-triazine, ATZ), followed by culture for 24 hours to induce malfunction of mitochondria. The cells with the malfunctioned mitochondria were treated with 0.2 mg/ml of MTT (3-(4,5-dimethylthiazol-2yl)-2,5-diphenyl-2H-tetrazolium bromide, MTT; Sigma, USA), followed by culture for 4 hours. Then, the MTT formazan precipitate formed by survived cells was dissolved in 100 μl of 0.04 N HCl/isopropanol. $OD_{540}$ was measured with an ELISA microplate reader (Molecular Devices, USA). The damage of mitochondria complex 1 was confirmed to see how the damage level was either increased or decreased, compared with the normal control group treated with DMSO without the extract or its active component. In the meantime, the negative control group was treated with 50 μg/ml of atrazine alone to induce mitochondrial damage and was not treated with the extract or its active component. Then, MTT assay was performed by the same manner as described above.

As a result, as shown in Table 3 below, the mitochondrial damage induced by atrazine was recovered to the normal level by the treatment of the Moutan Root Bark 90% ethanol extract, paeonol, paeoniflorin, or paeoniflorigenone (Table 3).

TABLE 3

Recovery effect of Moutan Root Bark extract and its active component on the damage of mitochondrial complex 1

| Treatment | | Inducer | |
|---|---|---|---|
| Treatment substance | Conc. (μg/ml) | (atrazine, μg/ml) | MTT (% of control) |
| Normal control | — | — | 100.0 ± 2.79 |
| Negative control | — | 50 | 76.7 ± 7.35 |
| Moutan Root Bark extract | 1 | 50 | 94.3 ± 5.55 |
| Paeonol | 1 | 50 | 101.8 ± 7.21 |
| paeoniflorin | 1 | 50 | 96.4 ± 7.44 |
| paeoniflorigenone | 1 | 50 | 95.5 ± 6.09 |

<1-3> Recovery Effect of Moutan Root Bark Extract and its Active Component on the Loss of ATP Resulted from the Damage of Mitochondria To investigate the effect of the Moutan Root Bark extract and its active ingredient on the recovery of the mitochondrial functional damage, ATP assay was performed to confirm the recovery effect on the loss of ATP in cells.

Particularly, SH-SY5Y cells were cultured by the same manner as described in Experimental Example <1-2>, to which 50 μg/ml of atrazine was treated to induce malfunction of mitochondria. Then, 100 μl of the cell lysate obtained from the cells with the malfunctioned mitochondria was mixed with 100 μl of luciferin-luciferase by using ATP bioluminescent somatic cell assay kit (Sigma, USA), followed by culture at 20° C. for 10 minutes. The supernatant was obtained. Fluorescence signal was measured by using LB 9501 Lumat luminometer (Berthold, Germany). The fluorescence of the control well containing the cell free medium was used as the background. The measured values were calculated by subtracting the background, and the amount of ATP was normalized to the protein concentration. The normal control was not treated with the extract of the invention or the active component thereof but instead treated with DMSO alone. All the results were presented as % by the normal control to present the intracellular ATP level. The negative control was treated with 50 μg/ml of atrazine alone to induce mitochondrial damage and not treated with the extract or the active component thereof. The Intracellular ATP level was measured by the same manner as described above.

As a result, as shown in Table 4 below, the mitochondrial damage induced by atrazine was recovered to the normal level by the treatment of the Moutan Root Bark 90% ethanol extract, paeonol, paeoniflorin, or paeoniflorigenone (Table 4).

TABLE 4

Recovery effect of Moutan Root Bark extract and its active component on the loss of intracellular ATP

| Treatment | | Inducer | Intracellular |
|---|---|---|---|
| Treatment substance | Conc. (μg/ml) | (atrazine, μg/ml) | ATP content (% of control) |
| Normal control | — | — | 100.0 ± 6.45 |
| Negative control | — | 50 | 68.7 ± 8.09 |
| Moutan Root Bark extract | 1 | 50 | 91.2 ± 4.08 |
| Paeonol | 1 | 50 | 101.9 ± 7.42 |
| paeoniflorin | 1 | 50 | 94.3 ± 6.44 |
| paeoniflorigenone | 1 | 50 | 89.1 ± 7.97 |

<1-4> Expression of the Gene Involved in Parkinson's Disease or Mitochondria According to Moutan Root Bark Extract and its Active Component To investigate the effect of the Moutan Root Bark extract of the present invention and its active component on the recovery of damaged mitochondrial function, the expression levels of cytochrome c oxidase subunit III (COX III) gene synthesized by mitochondria gene and Park? (DJ-1), one of the causing genes of familial Parkinson's disease, were measured by real-time PCR (RT-PCR).

Particularly, SH-SY5Y cells were cultured by the same manner as described in Experimental Example <1-2>, and mitochondrial malfunction was induced. Then, the cells with the malfunctioned mitochondria were suspended in TRIzol (Invitrogen, USA) and total RNA was extracted therefrom according to the manufacturer's protocol. Total cDNA was synthesized with 1 μg of the extracted RNA was. PCR was performed with GeneAmp PCR system 9700 (Applied Biosystem, USA) under the required optimum condition by using the synthesized cDNA as a template in the presence of the forward and reverse primers listed in Table 5 below, leading to the amplification of COX III and Park? (DJ-1) genes. The amplified PCR products were electrophoresed on 1.5% agarose gel. The relative concentration was measured by using an image densitometer (Alpha Ease FC software; Alpha Innotech, USA) under UV. The level of mRNA was standardized by comparison with the level of 18S rRNA. The normal control was not treated with the extract of the invention or the active component thereof but instead treated with DMSO alone. The negative control was treated with 50 μg/ml of atrazine alone to induce mitochondrial damage and not treated with the extract or the active component thereof. The gene expression level was investigated by the same manner as described above.

TABLE 5

Sequences of the primers used in this invention

| Gene name | Primer name | Primer sequence | SEQ. ID. NO: | Product length (bp) | Temp. (° C.) |
|---|---|---|---|---|---|
| COX III | COX III_F | 5'-CAATGATGGCGCGATGTAAC-3' | SEQ. ID. NO: : 1 | 270 | 60 |
| | COX III_R | 5'-GGTGATTGATACTCCTGATG-3' | SEQ. ID. NO: : 2 | | |

TABLE 5-continued

Sequences of the primers used in this invention

| Gene name | Primer name | Primer sequence | SEQ. ID. NO: | Product length (bp) | Temp. (° C.) |
|---|---|---|---|---|---|
| PARK7 | PARK7_F | 5'-CGAGCTGGGATTAAGGTCAC-3' | SEQ. ID. NO: : 3 | 267 | 60 |
|  | PARK7_R | 5'-TTCATGAGCCAACAGAGCAG-3' | SEQ. ID. NO: : 4 |  |  |
| GRP78 | GRP78_F | 5'-GAGATCATCGCCAACGATCAG-3' | SEQ. ID. NO: : 5 | 188 | 55 |
|  | GRP78_R | 5'-ACTTGATGTCCTGCTGCACAG-3' | SEQ. ID. NO: : 6 |  |  |
| XBP1p | XBP1p_F | 5'-GGTCTGCTGAGTCCGCAGCAGG-3' | SEQ. ID. NO: : 7 | 335 | 60 |
|  | XBP1p_R | 5'-GGGCTTGGTATATATGTGG-3' | SEQ. ID. NO: : 8 |  |  |
| iNOS | iNOS_F | 5'-CCTGGAGGTTCTGGATGAGA-3' | SEQ. ID. NO: : 9 | 320 | 60 |
|  | iNOS_R | 5'-GTAGTAGCGGGGCTTCAAGA-3' | SEQ. ID. NO: : 10 |  |  |
| IL-6 | IL-6_F | 5'-CTGGAGTACCATAGCTACCTGGAG-3' | SEQ. ID. NO: : 11 | 190 | 60 |
|  | IL-6_R | 5'-GTCCTTAGCCACTCCTTCTGTG-3' | SEQ. ID. NO: : 12 |  |  |
| p65/RELA | p65/RELA_F | 5'-GACCAACAATAACCCCTTTCAC-3' | SEQ. ID. NO: : 13 | 700 | 60 |
|  | p65/RELA_R | 5'-GTTTGAGATCTGCCCTGATGG-3' | SEQ. ID. NO: : 14 |  |  |
| 18s rRNA | 18s rRNA_F | 5'-GAGCGAAAGCATTTGCCAAG-3' | SEQ. ID. NO: : 15 | 101 | 60 |
|  | 18s rRNA_R | 5'-GGCATCGTTTATGGTCGGAA-3' | SEQ. ID. NO: : 16 |  |  |

As a result, as shown in Table 6 and Table 7, the reduced expressions of COX III synthesized by mitochondrial gene and Park7 (DJ-1), one of the causing genes of familial Parkinson's disease, were both recovered to the normal level (Tables 6 and 7).

TABLE 6

Expression of COX III according to Moutan Root Bark extract and its active component

| Treatment substance | | Conc. (µg/ml) | COX III/18S rRNA |
|---|---|---|---|
| Normal control | — | — | 1.00 ± 0.04 |
| Moutan Root Bark extract | — | 1 | 0.93 ± 0.06 |
| Paeonol | — | 1 | 1.05 ± 0.03 |
| paeoniflorin | — | 1 | 1.11 ± 0.04 |
| paeoniflorigenone | — | 1 | 1.04 ± 0.05 |
| Negative control | atrazine | — | 0.52 ± 0.08 |
| Moutan Root Bark extract | atrazine | 1 | 0.91 ± 0.08 |
| Paeonol | atrazine | 1 | 1.07 ± 0.07 |
| paeoniflorin | atrazine | 1 | 0.92 ± 0.08 |
| paeoniflorigenone | atrazine | 1 | 0.86 ± 0.07 |

TABLE 7

Expression of Park7 (DJ-1) according to Moutan Root Bark extract and its active component

| Treatment substance | | Conc. (µg/ml) | Park7(DJ-1)/18S rRNA |
|---|---|---|---|
| Normal control | — | — | 1.00 ± 0.08 |
| Moutan Root Bark extract | — | 1 | 0.98 ± 0.07 |
| Paeonol | — | 1 | 1.22 ± 0.08 |
| paeoniflorin | — | 1 | 1.05 ± 0.08 |
| paeoniflorigenone | — | 1 | 0.98 ± 0.08 |
| Negative control | atrazine | — | 0.39 ± 0.02 |
| Moutan Root Bark extract | atrazine | 1 | 1.30 ± 0.08 |
| Paeonol | atrazine | 1 | 0.95 ± 0.07 |
| paeoniflorin | atrazine | 1 | 2.03 ± 0.07 |
| paeoniflorigenone | atrazine | 1 | 0.45 ± 0.02 |

Experimental Example 2: Evaluation of Intracellular Efficacy of Angelica Dahurica Root Extract and its Active Component <2-1> Effect of Angelica Dahurica Root Extract and its Active Component on Cell Survival Rate To evaluate the intracellular efficacy of the Angelica Dahurica Root extract of the present invention and its active component, cytotoxicity in human neuroblastoma cells was investigated.

Particularly, SH-SY5Y cells were cultured by the same manner as described in Experimental Example <1-1>. The cultured cells were transferred in a serum free medium at the density of $2.5 \times 10^4$ cells/well. The cells were treated with 1.0 µg/ml of the Angelica Dahurica Root extract prepared in Example <1-2> or 0.5 µg/ml or 1.0 µg/ml of the active component thereof, Imperatorin, for 4 hours. The cells were collected and the cell survival rate was measured by using calcein. The cell survival rate that was increased or decreased compared with that of the normal control group not-treated with the extract or its active component above and instead treated with DMSO was calculated and presented as percentage (%).

As a result, as shown in table 8, the Angelica Dahurica Root extract and Imperatorin did not cause cytotoxicity in the normal cells at the concentration of 0.5 µg/ml. However, Imperatorin did cause toxicity at a low level at the concentration of 1 µg/ml (Table 8).

TABLE 8

Cell survival rate according to *Angelica Dahurica* Root extract and its active component

| Treatment substance | | Conc. (µg/ml) | Cell survival rate (% of control) |
|---|---|---|---|
| Normal control | — | — | 100.00 ± 0.89 |
| *Angelica Dahurica* Root extract and active ingredient | 90% ethanol extract | 1.0 | 99.50 ± 1.02 |
| | Imperatorin | 0.5 | 101.16 ± 0.59 |
| | Imperatorin | 1.0 | 79.16 ± 1.39 |

<2-2> Inhibitory Effect of Angelica Dahurica Root Extract and its Active Component on Cell Death Induced by Endoplasmic Reticulum Stress To investigate whether or not the Angelica Dahurica Root extract of the invention and the active component thereof could induce recovery of endoplasmic reticulum stress, MTT assay was performed with the cells having endoplasmic reticulum stress induced by the treatment of tunicamycin (Tuni) known to induce endoplasmic reticulum stress by inhibiting N-glycosylation or by the treatment of thapsigargin (Thap) known to induce endoplasmic reticulum stress by destroying calcium homeostasis to confirm the recovery of mitochondria complex 1 damage in living cells.

Particularly, SH-SY5Y cells were cultured by the same manner as described in Experimental Example <1-2>. The cells were treated with 1.0 ug/ml of the Angelica Dahurica Root extract prepared in Example <1-2> or 0.5 µg/ml or 1.0 µg/ml of Imperatorin, the active component thereof, followed by culture for 4 hours. The cells were treated with 0.5 µg/ml of thapsigargin (Thap) or 1 µg/ml of tunicamycin (Tuni), followed by culture for 24 hours to induce endoplasmic reticulum stress. Then, MTT assay was performed by the same manner as described in Experimental Example <1-2>. Compared with the normal control cells not treated with the extract or the active component thereof but treated with DMSO, the damage of mitochondria complex 1 in the cells, either increased or decreased, was investigated. The negative control was treated with 0.5 µg/ml of thapsigargin or 1 µg/ml of tunicamycin to cause endoplasmic reticulum stress but not treated with the extract or the active component thereof, followed by MTT assay by the same manner as described above.

As a result, as shown in Table 9 and Table 10, the functional damage of mitochondria and cell death induced by endoplasmic reticulum stress caused by thapsigargin or tunicamycin were recovered to the normal level by the treatment of the Angelica Dahurica Root 90% ethanol extract and imperatorin (Tables 9 and 10).

TABLE 9

Recovery effect of *Angelica Dahurica* Root extract and the active component thereof on the endoplasmic reticulum stress mediated mitochondria complex 1 damage induced by thapsigargin

| Treatment | | Inducer | |
| --- | --- | --- | --- |
| Treatment substance | Conc. (μg/ml) | (thapsigargin, μg/ml) | MTT (% of control) |
| Normal control | — | — | 100.00 ± 4.09 |
| Negative control | — | 0.5 | 65.61 ± 1.37 |
| Angelica Dahurica Root extract | 1.0 | 0.5 | 82.45 ± 3.80 |
| Imperatorin | 0.5 | 0.5 | 86.23 ± 5.31 |

TABLE 10

Recovery effect of *Angelica Dahurica* Root extract and the active component thereof on the endoplasmic reticulum stress mediated mitochondria complex 1 damage induced by tunicamycin

| Treatment | | Inducer | |
| --- | --- | --- | --- |
| Treatment substance | Conc. (μg/ml) | (tunicamycin, μg/ml) | MTT (% of control) |
| Normal control | — | — | 100.00 ± 5.73 |
| Negative control | — | 1.0 | 69.63 ± 3.42 |
| Angelica Dahurica Root extract | 1.0 | 1.0 | 83.99 ± 2.01 |
| Imperatorin | 0.5 | 1.0 | 84.93 ± 3.68 |

<2-3> Recovery Effect of Angelica Dahurica Root Extract and the Active Component of the Same on the Loss of ATP Resulted from Endoplasmic Reticulum Stress To investigate the effect of the Angelica Dahurica Root extract and its active component on the recovery of endoplasmic reticulum stress, ATP assay was performed to confirm the recovery effect on the loss of ATP in cells.

Particularly, SH-SY5Y cells were cultured by the same manner as described in Experimental Example <2-2>, and endoplasmic reticulum stress was induced. Then, the intracellular ATP level was measured by the same manner as described in Experimental Example <1-3>. The normal control was not treated with the extract of the invention or the active component thereof but treated with DMSO alone. All the results were presented as % by the normal control to present the intracellular ATP level. The negative control was not treated with the extract or the active component but treated with 0.5 μg/ml of thapsigargin or 1.0 μg/ml of tunicamycin alone to induce endoplasmic reticulum stress. Then, the Intracellular ATP level was measured by the same manner as described above.

As a result, as shown in Table 11, the functional damage of mitochondria and the cell death of human neuroblastoma cells induced by endoplasmic reticulum stress caused by thapsigargin or tunicamycin were recovered to the normal level by the treatment of the Angelica Dahurica Root 90% ethanol extract and Imperatorin (Table 11).

TABLE 11

Recovery effect of *Angelica Dahurica* Root extract and its active component on the loss of intracellular ATP

| Treatment | | | Intracellular |
| --- | --- | --- | --- |
| Treatment substance | Conc. (μg/ml) | Inducer (μg/ml) | ATP content (% of control) |
| Normal control | — | — | 100.00 ± 6.06 |
| Negative control | — | thapsigargin, 0.5 | 77.89 ± 3.28 |
| Angelica Dahurica Root extract | 1.0 | thapsigargin, 0.5 | 112.05 ± 7.21 |
| Imperatorin | 0.5 | thapsigargin, 0.5 | 104.85 ± 5.13 |
| Negative control | — | tunicamycin, 1.0 | 69.25 ± 2.09 |
| Angelica Dahurica Root extract | 1.0 | tunicamycin, 1.0 | 84.85 ± 3.05 |
| Imperatorin | 0.5 | tunicamycin, 1.0 | 86.00 ± 1.18 |

<2-4> Expression of Endoplasmic Reticulum Stress Marker Gene According to Angelica Dahurica Root Extract and its Active Component To investigate the effect of the Angelica Dahurica Root extract of the present invention and its active component on the recovery of endoplasmic reticulum stress, the expression levels of the endoplasmic reticulum stress marker genes GRP78 and XBP1p were measured.

Particularly, SH-SY5Y cells were cultured by the same manner as described in Experimental Example <2-2>, and endoplasmic reticulum stress was induced. Then, RT-PCR was performed with the cells having endoplasmic reticulum stress by the same manner as described in Experimental Example <1-4>, followed by electrophoresis to investigate the expression levels of GRP78 and XBP1p genes on 1.5% agarose gel under UV. The normal control was not treated with the extract of the invention or the active component thereof but treated with DMSO alone. The negative control was not treated with the extract or the active component but treated with 0.5 μg/ml of thapsigargin alone to induce endoplasmic reticulum stress. Then, the expression of the endoplasmic reticulum stress marker gene was confirmed by the same manner as described above.

As a result, as shown in Table 12 and Table 13, the expression levels of the endoplasmic reticulum stress marker genes GRP78 and XBP1p were recovered to the normal level in the cells having endoplasmic reticulum stress induced therein by the treatment of the Angelica Dahurica Root 90% ethanol extract and imperatorin (Tables 12 and 13).

TABLE 12

Expression of GRP78 mRNA according to *Angelica Dahurica* Root extract and its active component in cells having endoplasmic reticulum stress induced by thapsigargin

| Treatment | | Inducer | |
| --- | --- | --- | --- |
| Treatment substance | Conc. (μg/ml) | (thapsigargin, μg/ml) | GRP78/18S mRNA |
| Normal control | — | — | 1.93 ± 0.03 |
| Negative control | — | 0.5 | 100.00 ± 2.37 |
| Angelica Dahurica Root extract | 1.0 | 0.5 | 2.78 ± 0.03 |
| Imperatorin | 0.5 | 0.5 | 2.97 ± 0.05 |

TABLE 13

Expression of XBP1p mRNA according to *Angelica Dahurica* Root extract and its active component in cells having endoplasmic reticulum stress induced by thapsigargin

| Treatment | | Inducer | |
|---|---|---|---|
| Treatment substance | Conc. (μg/ml) | (thapsigargin, μg/ml) | XBP1p/18S mRNA |
| Normal control | — | — | 3.58 ± 0.06 |
| Negative control | — | 0.5 | 100.00 ± 3.18 |
| *Angelica Dahurica* Root extract | 1.0 | 0.5 | 4.89 ± 0.07 |
| Imperatorin | 0.5 | 0.5 | 4.01 ± 0.05 |

Experimental Example 3: Evaluation of Intracellular Efficacy of Bupleurum Root Extract and its Active Component <3-1> Effect of Bupleurum Root Extract and its Active Component on Cell Survival Rate To evaluate the intracellular efficacy of the Bupleurum Root extract of the present invention and its active component, cytotoxicity in murine microglial cells was investigated.

Particularly, BV2, the mouse microglial cell line, was inoculated in 1:1 DMEM (Dulbeco's Modified Eagle's Medium; Gibco, USA) supplemented with 10% FBS, followed by culture in a 37° C., 5% $CO_2$/95% air ($O_2$) incubator. Then, the cultured cells were transferred into a serum free medium at the density of $2.5 \times 10^4$ cells/well. The cells were treated with the Bupleurum Root 90% ethanol extract prepared in Example <1-3>, saikosaponin A, saikosaponin B2, saikosaponin B4, or saikosaponin D at the concentration of 1.0 μg/ml for 4 hours. The cells were collected and the cell survival rate was measured by using calcein. The survival rate of the cells that were increased or decreased compared with that of the normal control cells not-treated with the extract or its active component above and instead treated with DMSO was calculated and presented as percentage (%).

As a result, as shown in Table 14 below, the Bupleurum Root extract and its active component did not show cytotoxicity in normal cells (Table 14).

TABLE 14

Effect of *Bupleurum* Root extract and its active component on cell survival rate

| Treatment substance | | Conc. (μg/ml) | Cell survival rate (% of control) |
|---|---|---|---|
| Normal control | | — | 100.00 ± 6.48 |
| *Bupleurum* Root extract and its active component | 90% ethanol extract | 1.0 | 101.46 ± 9.38 |
| | Saikosaponin A | 1.0 | 98.38 ± 7.69 |
| | saikosaponin B2 | 1.0 | 102.74 ± 8.55 |
| | saikosaponin B4 | 1.0 | 97.99 ± 2.86 |
| | saikosaponin D | 1.0 | 97.45 ± 3.99 |

<3-2> Inhibitory Effect of Bupleurum Root Extract and its Active Component on Cell Death Induced by Inflammatory Response To investigate the inhibitory effect of the Bupleurum Root extract of the present invention and its active ingredient on inflammatory response, MTT assay was performed with the cells having inflammatory response induced by lipopolysaccharide (LPS) to confirm the recovery effect on the damage of mitochondria complex 1 in living cells.

Particularly, BV2 cells were cultured by the same manner as described in Experimental Example <3-1>. Then, the cultured cells were transferred into a serum free medium at the density of $1 \times 10^5$ cells/well. The cells were treated with the Bupleurum Root 90% ethanol extract prepared in Example <1-3>, saikosaponin A, saikosaponin B2, saikosaponin B4, or saikosaponin D at the concentration of 1.0 μg/ml, followed by culture for 4 hours. The cells were then treated with 100 ng/ml of lipopolysaccharide (LPS), followed by culture for 20 hours to induce inflammatory response. MTT assay was performed with the cells induced with inflammatory response by the same manner as described in Experimental Example <1-2>. The damage of mitochondria complex 1 was confirmed to see how the damage level was either increased or decreased, compared with the normal control group treated with DMSO without the extract or its active component. In the meantime, the negative control group was treated with 100 ng/ml of LPS alone to induce inflammatory response and was not treated with the extract or its active component. Then, MTT assay was performed by the same manner as described above.

As a result, as shown in Table 15 below, the inflammatory response induced by LPS was recovered to the normal level by the treatment of the Bupleurum Root 90% ethanol extract, saikosaponin A, saikosaponin B2, saikosaponin B4, or saikosaponin D (Table 15).

TABLE 15

Recovery effect of *Bupleurum* Root extract and its active component on the damage of mitochondrial complex 1

| Treatment | | | |
|---|---|---|---|
| Treatment substance | Conc. (μg/ml) | Inducer (LPS, ng/ml) | MTT (% of control) |
| Normal control | — | — | 100.00 ± 9.56 |
| Negative control | — | 100 | 52.17 ± 7.86 |
| *Bupleurum* Root extract | 1.0 | 100 | 89.06 ± 6.78 |
| saikosaponin A | 1.0 | 100 | 91.49 ± 6.20 |
| saikosaponin B2 | 1.0 | 100 | 88.85 ± 6.48 |
| saikosaponin B4 | 1.0 | 100 | 87.12 ± 2.56 |
| saikosaponin D | 1.0 | 100 | 86.73 ± 1.25 |

<3-3> Reduction of Inflammatory Response Dependent Nitric Oxide (NO) by Bupleurum Root Extract and its Active Component To investigate the recovery effect of the Bupleurum Root extract of the present invention and its active component on inflammatory response, Griess method was performed to measure the concentration of nitrite/nitrate ($NO_x$) in the cell culture medium.

Particularly, BV2 cells were cultured by the same manner as described in Experimental Example <3-1>, and inflammatory response was induced. Then, 100 μl of the cell culture medium was obtained, to which 100 μl of Griess reagent comprising hydrochloric acid containing 5% sulfanilamide and 2% naphthylethylenediamine was added, followed by reaction in a dark room for 30 minutes. Upon completion of the reaction, $OD_{540}$ was measured with an EISA microplate reader (Versamax, USA). The concentration of nitric oxide in the medium was calculated using the standard calibration curve of sodium nitrite. The normal control was not treated with the extract or the active component thereof but treated with DMSO. The negative control was treated with 100 ng/ml of LPS alone to induce inflammatory response but not treated with the extract or the active component. Then, the nitric oxide concentration reduction effect was investigated by the same manner as described above.

As a result, as shown in Table 16, the Bupleurum Root 90% ethanol extract, saikosaponin A, saikosaponin B2, saikosaponin B4, and saikosaponin D were confirmed to have the effect of suppressing LPS mediated NO generation (Table 16).

TABLE 16

Nitric oxide (NO) concentration reduction effect of Bupleurum Root extract and its active component

| Treatment substance | Conc. (µg/ml) | Inducer (LPS, ng/ml) | NO (mM) |
|---|---|---|---|
| Normal control | — | — | 3.29 ± 0.03 |
| Negative control | — | 100 | 28.17 ± 4.73 |
| Bupleurum Root extract | 1.0 | 100 | 13.06 ± 2.34 |
| saikosaponin A | 1.0 | 100 | 10.75 ± 3.60 |
| saikosaponin B2 | 1.0 | 100 | 18.97 ± 2.68 |
| saikosaponin B4 | 1.0 | 100 | 17.21 ± 2.11 |
| saikosaponin D | 1.0 | 100 | 18.12 ± 2.93 |

<3-4> Expression of Inflammatory Response Marker Gene According to Bupleurum Root Extract and its Active Component To investigate the effect of the Bupleurum Root extract of the present invention and its active component on the recovery of inflammatory response, the expression levels of the inflammatory response marker genes inducible nitric oxide synthase (iNOS), interleukin-6, (IL-6) and NF-kB p65/ReIA.

Particularly, BV2 cells were cultured by the same manner as described in Experimental Example <3-1>, and inflammatory response was induced. Then, RT-PCR was performed with the cells by the same manner as described in Experimental Example <1-4>, followed by quantitative analysis of the expression levels of iNOS, IL-6, and NF-kB p65/ReIA genes. The normal control was not treated with the extract of the invention or the active component thereof but treated with DMSO alone. The negative control was not treated with the extract or the active component but treated with 100 ng/ml of LPS alone to induce inflammatory response. Then, the expression of the inflammatory response marker gene was confirmed by the same manner as described above.

As a result, as shown in Tables 17~19, the expression levels of the inflammatory response marker genes iNOS, IL-6 and NF-kB p65/ReIA were recovered to the normal level in the cells having inflammatory response induced therein by the treatment of the Bupleurum Root 90% ethanol extract, saikosaponin A, saikosaponin B2, saikosaponin B4, and saikosaponin D (Tables 17~19).

TABLE 17

Expression of iNOS mRNA according to Bupleurum Root extract and its active component

| Treatment substance | Conc. (µg/ml) | Inducer (LPS, ng/ml) | iNOS mRNA (% of control) |
|---|---|---|---|
| Normal control | — | — | 0.52 ± 0.01 |
| Negative control | — | 100 | 100.00 ± 1.82 |
| Bupleurum Root extract | 1.0 | 100 | 15.25 ± 0.11 |
| saikosaponin A | 1.0 | 100 | 14.85 ± 1.47 |
| saikosaponin B2 | 1.0 | 100 | 18.11 ± 2.39 |
| saikosaponin B4 | 1.0 | 100 | 26.06 ± 3.27 |
| saikosaponin D | 1.0 | 100 | 21.23 ± 1.99 |

TABLE 18

Expression of IL-6 mRNA according to Bupleurum Root extract and its active component

| Treatment substance | Conc. (µg/ml) | Inducer (LPS, ng/ml) | IL-6 mRNA (% of control) |
|---|---|---|---|
| Normal control | — | — | 1.18 ± 0.07 |
| Negative control | — | 100 | 100.00 ± 3.73 |
| Bupleurum Root extract | 1.0 | 100 | 26.30 ± 2.37 |
| saikosaponin A | 1.0 | 100 | 18.05 ± 1.23 |
| saikosaponin B2 | 1.0 | 100 | 29.67 ± 2.39 |
| saikosaponin B4 | 1.0 | 100 | 28.53 ± 1.92 |
| saikosaponin D | 1.0 | 100 | 26.58 ± 1.75 |

TABLE 19

Expression of p65/ReIA mRNA mRNA according to Bupleurum Root extract and its active component

| Treatment substance | Conc. (µg/ml) | Inducer (LPS, ng/ml) | p65/ReIA mRNA (% of control) |
|---|---|---|---|
| Normal control | — | — | 11.48 ± 0.53 |
| Negative control | — | 100 | 100.00 ± 1.12 |
| Bupleurum Root extract | 1.0 | 100 | 46.01 ± 3.19 |
| saikosaponin A | 1.0 | 100 | 40.38 ± 1.05 |
| saikosaponin B2 | 1.0 | 100 | 50.18 ± 2.67 |
| saikosaponin B4 | 1.0 | 100 | 53.70 ± 4.72 |
| saikosaponin D | 1.0 | 100 | 49.80 ± 3.54 |

<3-5> Reduction of Reactive Oxygen Species (ROS) Generation by Bupleurum Root Extract and its Active Component To investigate the recovery effect of the Bupleurum Root extract of the present invention and the active component thereof on inflammatory response, the concentration of intracellular ROS was measured by using 2',7'-dichlorofluoroscein diacetate (DCF-DA).

Particularly, BV2 cells were cultured by the same manner as described in Experimental Example <3-1>, and inflammatory response was induced. Then, the cells induced with inflammatory response were treated with 1 µM DCF-DA and 0.05 µM bisbenzimide (Hoechst 33342), followed by staining at 37° C. for 1 hour. After the staining, the fluorescence intensity of DCF-DA was measured at 485 nm/535 nm, and the fluorescence intensity of bisbenzimide was measured at 335 nm/460 nm. Based on the ratio of DCF-DA/bisbenzimide, ROS was quantified. The amount of ROS, either increased or decreased, was compared with that of the normal control not treated with the extract or the active component thereof but treated with DMSO, and the results were presented as %. The negative control was treated with 100 ng/ml of LPS alone to induce inflammatory response but not treated with the extract or the active component thereof. Then, the generation of ROS was investigated by the same manner as described above.

As a result, as shown in Table 20, the Bupleurum Root 90% ethanol extract of the present invention, saikosaponin A, saikosaponin B2, saikosaponin B4, and saikosaponin D were confirmed to have the effect of reducing the DCF-DA mediated ROS generation caused by inflammatory response and stress (Table 20).

TABLE 20

Reactive oxygen species (ROS) generation reduction effect of *Bupleurum* Root extract and its active component

| Treatment | | | |
|---|---|---|---|
| Treatment substance | Conc. (μg/ml) | Inducer (LPS, g/ml) | DCF-DA-ROS (% of control) |
| Normal control | — | — | 100.00 ± 1.09 |
| Negative control | — | 100 | 412.31 ± 4.26 |
| 90% ethanol extract | 1.0 | 100 | 235.45 ± 2.27 |
| saikosaponin A | 1.0 | 100 | 198.24 ± 3.72 |
| saikosaponin B2 | 1.0 | 100 | 214.22 ± 1.87 |
| saikosaponin B4 | 1.0 | 100 | 223.26 ± 2.86 |
| saikosaponin D | 1.0 | 100 | 218.61 ± 2.71 |

Experimental Example 4: Evaluation of Intracellular Efficacy of Mixture Extract Comprising at Least Two of Those Moutan Root Bark, Angelica Dahurica Root and Bupleurum Root <4-1> Recovery Effect of Mixture Extract Comprising at Least Two of Those Moutan Root Bark, Angelica Dahurica Root and Bupleurum Root on Mitochondrial Activity in Parkinson's Disease Cell Model To investigate the recovery effect of the extract of the mixture comprising at least two of those Moutan Root Bark, Angelica Dahurica Root and Bupleurum Root on mitochondrial activity in Parkinson's disease cell model, the mitochondrial activity index was examined in Parkinson's disease cell model.

Particularly, SH-SY5Y, the human neuroblastoma cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of $1 \times 10^5$ cells/well. The cells were treated with the mixed 90% ethanol extract of Moutan Root Bark and Angelica Dahurica Root prepared in Example 2, the mixed 90% ethanol extract of Moutan Root Bark and Bupleurum Root prepared in Example 3, the mixed 90% ethanol extract of Angelica Dahurica Root and Bupleurum Root prepared in Example 4, or the mixed 90% ethanol extract of Moutan Root Bark, Angelica Dahurica Root and Bupleurum Root prepared in Example <5-1> at the concentration of 1 μg/ml, followed by culture for 4 hours. Upon completion of the culture, the cells were treated with 1-methyl-4-phenylpyridinium (MPP+) at the concentration of 1 mM, followed by culture for 24 hours. As a result, Parkinson's disease cell model was constructed. Then, the cell survival rate was measured by the same manner as described in Experimental Example <1-1> using calcein. The cell survival rate that was increased or decreased compared with that of the normal control cells not-treated with the extract or its active component above and instead treated with DMSO was calculated and presented as percentage (%). The negative control was treated with 1 mM MPP+ alone, resulting in the construction of Parkinson's disease cell model that had not been treated with the extract or the active component thereof. Then, the cell survival rate was also measured, either increased or decreased, by comparing with that of the normal control by the same manner as described above.

As a result, as shown in Table 21, the cell survival rate of the Parkinson's disease cell model according to the reduction of mitochondrial activity caused by MPP+ was 65~70% recovered by the treatment of the mixture extract, precisely the ethanol extract of the mixture comprising Moutan Root Bark, Angelica Dahurica Root and Bupleurum Root at various mixing ratios. In the meantime, the recovery effect was increased and reached 77~81% by the treatment of the extract of the mixture of Moutan Root Bark and Bupleurum Root, the extract of the mixture of Moutan Root Bark and Angelica Dahurica Root, and the extract of the mixture of Angelica Dahurica Root and Bupleurum Root. In particular, the recovery effect was highest, that was 92.84%, when the extract of the mixture of Moutan Root Bark, Angelica Dahurica Root and Bupleurum Root was treated (Table 21).

TABLE 21

Effect of mixture extract comprising at least two of those Moutan Root Bark, *Angelica Dahurica* Root and *Bupleurum* Root on cell survival rate

| | Treatment | | | |
|---|---|---|---|---|
| Mixed composition | Mixing ratio | Conc. (μg/ml) | Inducer (MPP+, M) | Cell survival rate (% of control) |
| Normal control | — | — | — | 100.00 ± 4.70 |
| Negative control | — | — | 1.0 | 51.56 ± 2.24 |
| Moutan Root Bark | — | 1.0 | 1.0 | 69.91 ± 2.18 |
| *Angelica Dahurica* Root | — | 1.0 | 1.0 | 65.19 ± 2.87 |
| *Bupleurum* Root | — | 1.0 | 1.0 | 68.68 ± 1.78 |
| Moutan Root Bark + *Angelica Dahurica* Root | 1:5 1:1 1:0.2 | 1.0 1.0 1.0 | 1.0 1.0 1.0 | 78.33 ± 3.89 80.45 ± 4.02 78.24 ± 3.59 |
| Moutan Root Bark + *Bupleurum* Root | 1:5 1:1 1:0.2 | 1.0 1.0 1.0 | 1.0 1.0 1.0 | 78.36 ± 2.35 81.00 ± 4.08 78.31 ± 3.16 |
| *Angelica Dahurica* Root + *Bupleurum* Root | 1:5 1:1 1:0.2 | 1.0 1.0 1.0 | 1.0 1.0 1.0 | 78.22 ± 2.14 79.26 ± 3.18 77.98 ± 1.91 |
| Moutan Root Bark + *Angelica Dahurica* Root + *Bupleurum* Root | 1:1:1 | 1.0 | 1.0 | 92.84 ± 5.51 |

<4-2> Recovery Effect of Mixture Extract Comprising at Least Two of those Moutan Root Bark, Angelica Dahurica Root and Bupleurum Root on the loss of ATP in Parkinson's Disease Cell Model To investigate the effect of the extract of the mixture comprising at least two of those Moutan Root Bark, Angelica Dahurica Root and Bupleurum Root on the recovery of the mitochondrial functional damage in Parkinson's disease cell model, ATP assay was performed to confirm the recovery effect on the loss of ATP in cells.

Particularly, SH-SY5Y, the human neuroblastoma cell line, was inoculated in DMEM/F12 (1:1) supplemented with 10% FBS, followed by culture in a 37° C., 5% $CO_2$/95% air (O₂) incubator. Then, the cultured cells were transferred into a serum free medium at the density of 1×10⁵ cells/well. The cells were treated with the mixed 90% ethanol extract of Moutan Root Bark and Angelica Dahurica Root prepared in Example 2, the mixed 90% ethanol extract of Moutan Root Bark and Bupleurum Root prepared in Example 3, the mixed 90% ethanol extract of Angelica Dahurica Root and Bupleurum Root prepared in Example 4, or the mixed 90% ethanol extract of Moutan Root Bark, Angelica Dahurica Root and Bupleurum Root prepared in Example <5-1> at the concentration of 1 μg/ml, followed by culture for 4 hours. Upon completion of the culture, Parkinson's disease cell model was constructed by the same manner as described in Experimental Example <4-1>. Then, the intracellular ATP level was measured by the same manner as described in Experimental Example <1-3>. The increase or decrease of the intracellular ATP level was calculated by comparing that of the normal control which had not been treated with the extract or the active component but treated with DMSO alone. The negative control was treated with 1 mM MPP+ alone but not treated with the extract or the active component, followed by the investigation of the recovery of ATP level by the same manner as described above. The negative control was treated with 1 mM MPP+ alone, resulting in the construction of Parkinson's disease cell model that had not been treated with the extract or the active component thereof. Then, the recovery effect on the intracellular ATP level was investigated by the same manner as described above.

As a result, as shown in Table 22, the loss of intracellular ATP according to the decrease of mitochondrial activity caused by 1-methyl-4-phenylpyridinium (MPP+) was recovered by the treatment of the 90% ethanol single extract of Moutan Root Bark, Angelica Dahurica Root or Bupleurum Root up to 68~69% by the level of the normal group. In the meantime, the recovery rate was increased up to 78~83% by the treatment of the extract of the mixture of Moutan Root Bark and Bupleurum, the extract of the mixture of Moutan Root Bark and Angelica Dahurica, and the extract of the mixture of Angelica Dahurica Root and Bupleurum Root. In particular, the recovery rate was highest up to 95.82% when the extract of the mixture of Moutan Root Bark, Angelica Dahurica Root and Bupleurum Root was treated (Table 22).

TABLE 22

Recovery effect of the extract of the mixture comprising at least two of those Moutan Root Bark, *Angelica Dahurica* Root and *Bupleurum* Root on the loss of intracellular ATP

| Mixed composition | Mixing ratio | Conc. (μg/ml) | Inducer (MPP+, mM) | Intracellular ATP (% of control) |
|---|---|---|---|---|
| Normal control | — | — | — | 100.00 ± 2.99 |
| Negative control | — | — | 1.0 | 57.13 ± 3.17 |
| Moutan Root Bark | — | 1.0 | 1.0 | 69.28 ± 2.37 |
| Angelica Dahurica Root | — | 1.0 | 1.0 | 68.99 ± 3.57 |
| Bupleurum Root | — | 1.0 | 1.0 | 68.63 ± 2.49 |
| Moutan Root Bark + Angelica Dahurica Root | 1:5 | 1.0 | 1.0 | 78.44 ± 3.44 |
|  | 1:1 | 1.0 | 1.0 | 79.84 ± 3.01 |
|  | 1:0.2 | 1.0 | 1.0 | 78.50 ± 2.68 |
| Moutan Root Bark + Bupleurum Root | 1:5 | 1.0 | 1.0 | 80.93 ± 1.25 |
|  | 1:1 | 1.0 | 1.0 | 83.56 ± 3.15 |
|  | 1:0.2 | 1.0 | 1.0 | 81.43 ± 2.36 |
| Angelica Dahurica Root + Bupleurum Root | 1:5 | 1.0 | 1.0 | 78.29 ± 1.11 |
|  | 1:1 | 1.0 | 1.0 | 81.39 ± 2.89 |
|  | 1:0.2 | 1.0 | 1.0 | 79.92 ± 2.31 |
| Moutan Root Bark + Angelica Dahurica Root + Bupleurum Root | 1:1:1 | 1.0 | 1.0 | 95.82 ± 3.61 |

<4-3> Reduction of Reactive Oxygen Species (ROS) Generation in Parkinson's Disease Cell Model by the Extract of the Mixture Comprising at Least Two of those Moutan Root Bark, Angelica Dahurica Root and Bupleurum Root To investigate the reduction effect on ROS generation caused by mitochondrial functional damage in Parkinson's disease cell model according to the treatment of the extract of the mixture of Moutan Root Bark and Bupleurum, the extract of the mixture of Moutan Root Bark and Angelica Dahurica, the extract of the mixture of Angelica Dahurica Root and Bupleurum Root, and the extract of the mixture of Moutan Root Bark, Angelica Dahurica Root and Bupleurum Root, the concentration of intracellular ROS was measured by using 2′,7′-dichlorofluoroscein diacetate (DCF-DA). Particularly, SH-SY5Y, the human neuroblastoma cell line, was inoculated in DMEM/F12 (1:1) supplemented with 10% FBS, followed by culture in a 37° C., 5% CO₂/95% air (O₂) incubator. Then, the cultured cells were transferred into a serum free medium at the density of 1×10⁵ cells/well. The cells were treated with the mixed 90% ethanol extract of Moutan Root Bark and Angelica Dahurica Root prepared in Example 2, the mixed 90% ethanol extract of Moutan Root Bark and Bupleurum Root prepared in Example 3, the mixed 90% ethanol extract of Angelica Dahurica Root and Bupleurum Root prepared in Example 4, or the mixed 90% ethanol extract of Moutan Root Bark, Angelica Dahurica Root and Bupleurum Root prepared in Example <5-1> at the concentration of 1 μg/ml, followed by culture for 4 hours. Upon completion of the culture, Parkinson's disease cell model was constructed by the same manner as described in Experimental Example <4-1>. Then, ROS was quantified based on the ratio of DCF-DA/bisbenzimide by the same manner as described in Experimental Example <3-5>. The level of ROS, either increased or decreased, was compared with that of the normal control not treated with the extract or the active component thereof but treated with DMSO, and the results were presented as % by the normal control. The negative control Parkinson's disease cell model was constructed by the treatment of 1 mM MPP+ alone but not treated with the extract or the active component thereof. Then, the ROS generation reduction effect was investigated by the same manner as described above.

As a result, as shown in Table 23, the ROS generation resulted from the decreased mitochondrial activity caused by 1-methyl-4-phenylpyridinium (MPP+) was recovered as much as 144~146% by the normal level after the treatment of the 90% ethanol single extract of Moutan Root Bark, Angelica Dahurica Root or Bupleurum Root, while the ROS generation was recovered as much as 120~132% by the normal level after the treatment of the extract of the mixture of Moutan Root Bark and Bupleurum, the extract of the mixture of Moutan Root Bark and Angelica Dahurica, and the extract of the mixture of Angelica Dahurica Root and Bupleurum Root. In particular, the ROS generation was almost recovered to the normal level, which was 108.20%, by the treatment of the extract of the mixture of Moutan Root Bark, Angelica Dahurica Root and Bupleurum Root, suggesting that the extract of the mixture above had the highest recovery effect (Table 23).

TABLE 23

Reactive oxygen species (ROS) generation reduction effect of the extract of the mixture comprising at least two of those Moutan Root Bark, *Angelica Dahurica* Root and *Bupleurum* Root

| Mixed composition | Mixing ratio | Conc. (μg/ml) | Inducer (MPP+, mM) | DCF-DA-ROS (% of control) |
|---|---|---|---|---|
| Normal control | — | — | — | 100.00 ± 3.60 |
| Negative control | — | — | 1.0 | 165.85 ± 4.67 |
| Moutan Root Bark | — | 1.0 | 1.0 | 146.91 ± 5.05 |
| *Angelica Dahurica* Root | — | 1.0 | 1.0 | 144.44 ± 2.97 |
| *Bupleurum* Root | — | 1.0 | 1.0 | 145.67 ± 5.88 |
| Moutan Root Bark + *Angelica Dahurica* Root | 1:5 | 1.0 | 1.0 | 125.01 ± 2.39 |
| | 1:1 | 1.0 | 1.0 | 124.69 ± 2.79 |
| | 1:0.2 | 1.0 | 1.0 | 128.55 ± 1.75 |
| Moutan Root Bark + *Bupleurum* Root | 1:5 | 1.0 | 1.0 | 122.23 ± 1.03 |
| | 1:1 | 1.0 | 1.0 | 120.82 ± 2.37 |
| | 1:0.2 | 1.0 | 1.0 | 123.82 ± 1.23 |
| *Angelica Dahurica* Root + *Bupleurum* Root | 1:5 | 1.0 | 1.0 | 131.86 ± 1.67 |
| | 1:1 | 1.0 | 1.0 | 130.99 ± 3.78 |
| | 1:0.2 | 1.0 | 1.0 | 132.71 ± 4.54 |
| Moutan Root Bark + *Angelica Dahurica* Root + *Bupleurum* Root | 1:1:1 | 1.0 | 1.0 | 108.20 ± 1.90 |

Experimental Example 5: Evaluation of Intracellular Efficacy of Mixture Extract of Moutan Root Bark, Angelica Dahurica Root and Bupleurum Root According to Different Mixing Ratios <5-1> Recovery Effect of Mixture Extract of Moutan Root Bark, Angelica Dahurica Root and Bupleurum Root According to Different Mixing Ratios on Mitochondrial Activity in Parkinson's Disease Cell Model To investigate the recovery effect of the extract of the mixture of Moutan Root Bark, Angelica Dahurica Root and Bupleurum Root according to different mixing ratios on mitochondrial activity in Parkinson's disease cell model, the index for mitochondrial activity was first confirmed to compare the recovery effect.

Particularly, SH-SY5Y, the human neuroblastoma cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of $1\times10^5$ cells/well. The cells were treated with the various mixed 90% ethanol extracts of Moutan Root Bark and Angelica Dahurica Root having different mixing ratios prepared in Example 5 at the concentration of 1 μg/ml, followed by culture for 4 hours. Upon completion of the culture, the Parkinson's disease cell model was constructed by the same manner as described in Experimental Example <4-1>. Then, the cell survival rate was measured by using calcein by the same manner as described in Experimental Example <1-1>. The cell survival rate that was increased or decreased compared with that of the normal control group not-treated with the extract or its active component above but treated with DMSO was calculated and presented as percentage (%). The negative control Parkinson's disease cell model was constructed by the treatment of 1 mM MPP+ alone but not treated with the extract or the active component thereof. Then, the cell survival rate that was increased or decreased compared with that of the normal control group was calculated and presented as percentage (%) by the same manner as described above.

As a result, as shown in Table 24, the reduced mitochondrial activity caused by 1-methyl-4-phenylpyridinium was recovered as much as 93.22% by the normal control after the treatment of the extract of the mixture of Moutan Root Bark, Angelica Dahurica Root and Bupleurum Root (1:1:1), which was the highest (Table 24).

TABLE 24

Effect of mixture extract of Moutan Root Bark, *Angelica Dahurica* Root and *Bupleurum* Root according to different mixing ratios on cell survival rate

| Mixed composition | Mixing ratio* | Conc. (μg/ml) | Inducer (MPP+, mM) | Cell survival rate (% of Control) |
|---|---|---|---|---|
| Normal control | — | — | — | 100.00 ± 4.55 |
| Negative control | — | — | 1.0 | 55.24 ± 3.74 |
| Moutan Root Bark + *Angelica Dahurica* Root + *Bupleurum* Root mixture extract | 1:1:1 | 1.0 | 1.0 | 93.22 ± 3.92 |
| | 1:1:2 | 1.0 | 1.0 | 84.26 ± 2.62 |
| | 1:2:1 | 1.0 | 1.0 | 85.61 ± 2.44 |
| | 1:2:2 | 1.0 | 1.0 | 86.30 ± 5.38 |
| | 1:1:0.5 | 1.0 | 1.0 | 84.27 ± 4.51 |
| | 1:0.5:1 | 1.0 | 1.0 | 83.72 ± 4.65 |
| | 1:0.5:0.5 | 1.0 | 1.0 | 86.88 ± 0.42 |
| | 1:1:3 | 1.0 | 1.0 | 86.78 ± 2.71 |
| | 1:3:1 | 1.0 | 1.0 | 84.87 ± 2.92 |
| | 1:3:3 | 1.0 | 1.0 | 84.06 ± 3.25 |
| | 1:1:0.33 | 1.0 | 1.0 | 84.50 ± 4.83 |
| | 1:0.33:1 | 1.0 | 1.0 | 86.16 ± 3.99 |
| | 1:0.33:0.33 | 1.0 | 1.0 | 83.89 ± 4.83 |
| | 1:1:4 | 1.0 | 1.0 | 87.56 ± 2.82 |
| | 1:4:1 | 1.0 | 1.0 | 84.88 ± 3.59 |
| | 1:4:4 | 1.0 | 1.0 | 85.65 ± 5.92 |
| | 1:1:0.25 | 1.0 | 1.0 | 86.30 ± 2.42 |
| | 1:0.25:1 | 1.0 | 1.0 | 87.99 ± 2.92 |
| | 1:0.25:0.25 | 1.0 | 1.0 | 85.17 ± 1.76 |
| | 1:1:5 | 1.0 | 1.0 | 86.22 ± 0.82 |
| | 1:5:1 | 1.0 | 1.0 | 86.21 ± 0.72 |
| | 1:5:5 | 1.0 | 1.0 | 86.31 ± 2.19 |
| | 1:1:0.2 | 1.0 | 1.0 | 84.14 ± 1.81 |
| | 1:0.2:1 | 1.0 | 1.0 | 85.20 ± 3.02 |
| | 1:0.2:0.2 | 1.0 | 1.0 | 84.47 ± 1.21 |

*Mixing ratio of the extract of the mixture is weight ratio of Moutan Root Bark:*Angelica Dahurica* Root:*Bupleurum* Root(w:w:w).

<5-2> Recovery Effect of Mixture Extract of Moutan Root Bark, Angelica Dahurica Root and Bupleurum Root According to Different Mixing Ratios on the Loss of Intracellular ATP in Parkinson's Disease Cell Model To investigate the effect of the extract of the mixture of Moutan Root Bark, Angelica Dahurica Root and Bupleurum Root according to different mixing ratios on the recovery of the mitochondrial functional damage in Parkinson's disease cell model, ATP assay was performed to confirm the recovery effect on the loss of intracellular ATP.

Particularly, SH-SY5Y, the human neuroblastoma cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of $1\times10^5$ cells/well. The cells were treated with the various mixed 90% ethanol extracts of Moutan Root Bark and Angelica Dahurica Root having different mixing ratios prepared in Example 5 at the concentration of 1 μg/ml, followed by culture for 4 hours. Upon completion of the culture, the Parkinson's disease cell model was constructed by the same manner as described in Experimental Example <4-1>. Then, the intracellular ATP level was measured by the same manner as described in Experimental Example <1-3>. The intracellular ATP level that was increased or decreased compared with that of the normal control group not-treated with the extract or its active component above but treated with DMSO was calculated and presented as percentage (%). The negative control Parkinson's disease cell model was constructed by the treatment of 1 mM MPP+ alone but not treated with the extract or the active component thereof. Then the recovery effect on the loss of intracellular ATP was confirmed by the same manner as described above.

As a result, as shown in Table 25, the loss of intracellular ATP caused by 1-methyl-4-phenylpyridinium was recovered as much as 94.10% by the normal control after the treatment of the extract of the mixture of Moutan Root Bark, Angelica Dahurica Root and Bupleurum Root (1:1:1), which was the highest (Table 25).

TABLE 25

Recovery effect of mixture extract of Moutan Root Bark, *Angelica Dahurica* Root and *Bupleurum* Root according to different mixing ratios on the loss of intracellular ATP

| Mixed composition | Mixing ratio* | Conc. (μg/ml) | Inducer (MPP+, μM) | Intracellular ATP content (% of Control) |
|---|---|---|---|---|
| Normal control | — | — | — | 100.00 ± 1.73 |
| Negative control | — | — | 1.0 | 60.88 ± 1.35 |
| Moutan Root Bark + *Angelica Dahurica* Root + *Bupleurum* Root mixture extract | 1:1:1 | 1.0 | 1.0 | 94.10 ± 3.56 |
| | 1:1:2 | 1.0 | 1.0 | 85.22 ± 1.89 |
| | 1:2:1 | 1.0 | 1.0 | 87.47 ± 2.61 |
| | 1:2:2 | 1.0 | 1.0 | 87.00 ± 2.18 |
| | 1:1:0.5 | 1.0 | 1.0 | 85.18 ± 1.89 |
| | 1:0.5:1 | 1.0 | 1.0 | 90.22 ± 3.96 |
| | 1:0.5:0.5 | 1.0 | 1.0 | 86.32 ± 2.12 |
| | 1:1:3 | 1.0 | 1.0 | 88.14 ± 2.44 |
| | 1:3:1 | 1.0 | 1.0 | 87.21 ± 2.39 |
| | 1:3:3 | 1.0 | 1.0 | 87.47 ± 1.92 |
| | 1:1:0.33 | 1.0 | 1.0 | 88.17 ± 2.15 |
| | 1:0.33:1 | 1.0 | 1.0 | 88.24 ± 2.59 |
| | 1:0.33:0.33 | 1.0 | 1.0 | 86.99 ± 1.44 |
| | 1:1:4 | 1.0 | 1.0 | 86.21 ± 3.60 |
| | 1:4:1 | 1.0 | 1.0 | 84.51 ± 0.13 |
| | 1:4:4 | 1.0 | 1.0 | 86.99 ± 1.39 |
| | 1:1:0.25 | 1.0 | 1.0 | 87.72 ± 4.32 |
| | 1:0.25:1 | 1.0 | 1.0 | 85.14 ± 1.84 |
| | 1:0.25:0.25 | 1.0 | 1.0 | 87.45 ± 3.44 |
| | 1:1:5 | 1.0 | 1.0 | 86.29 ± 3.92 |
| | 1:5:1 | 1.0 | 1.0 | 84.01 ± 1.85 |
| | 1:5:5 | 1.0 | 1.0 | 87.70 ± 1.59 |
| | 1:1:0.2 | 1.0 | 1.0 | 87.38 ± 2.60 |
| | 1:0.2:1 | 1.0 | 1.0 | 87.68 ± 3.14 |
| | 1:0.2:0.2 | 1.0 | 1.0 | 89.34 ± 3.12 |

*Mixing ratio of the extract of the mixture is weight ratio of Moutan Root Bark:*Angelica Dahurica* Root:*Bupleurum* Root(w:w:w).

<5-3> Reactive Oxygen Species (ROS) Generation Reduction Effect of Mixture Extract of Moutan Root Bark, Angelica Dahurica Root and Bupleurum Root According to Different Mixing Ratios in Parkinson's Disease Cell Model To investigate the recovery effect of the extract of the mixture of Moutan Root Bark, Angelica Dahurica Root and Bupleurum Root according to different mixing ratios in Parkinson's disease cell model, the concentration of intracellular ROS was measured by using 2',7'-dichlorofluorosceindiacetate (DCF-DA).

Particularly, BV2, the mouse microglial cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of 1×10⁵ cells/well. The cells were treated with the various mixed 90% ethanol extracts of Moutan Root Bark and Angelica Dahurica Root having different mixing ratios prepared in Example 5 at the concentration of 1 μg/ml, followed by culture for 4 hours. Upon completion of the culture, the Parkinson's disease cell model was constructed by the same manner as described in Experimental Example <4-1>. Then, ROS was quantified based on the ratio of DCF-DA/bisbenzimide by the same manner as described in Experimental Example <3-5>. The level of ROS, either increased or decreased, was compared with that of the normal control not treated with the extract or the active component thereof but treated with DMSO, and the results were presented as % by the normal control. The negative control Parkinson's disease cell model was constructed by the treatment of 1 mM MPP+ alone but not treated with the extract or the active component thereof. Then, the ROS generation reduction effect was investigated by the same manner as described above.

As a result, as shown in Table 26, the ROS generation resulted from the decreased mitochondrial activity caused by 1-methyl-4-phenylpyridinium was recovered as much as 106.23% by the normal control after the treatment of the extract of the mixture of Moutan Root Bark, Angelica Dahurica Root and Bupleurum Root (1:1:1), which was the highest (Table 26).

TABLE 26

Reactive oxygen species (ROS) generation reduction effect of the extract of the mixture of Moutan Root Bark, *Angelica Dahurica* Root and *Bupleurum* Root according to different mixing ratios

| Mixed composition | Mixing ratio* | Conc. (μg/ml) | Inducer (MPP+, mM) | DCF-DA-ROS (% of Control) |
|---|---|---|---|---|
| Normal control | — | — | — | 100.00 ± 1.78 |
| Negative control | — | — | 1.0 | 162.14 ± 0.33 |
| Moutan Root Bark + *Angelica Dahurica* Root + *Bupleurum* Root mixture extract | 1:1:1 | 1.0 | 1.0 | 106.23 ± 1.76 |
| | 1:1:2 | 1.0 | 1.0 | 112.70 ± 2.46 |
| | 1:2:1 | 1.0 | 1.0 | 114.79 ± 1.79 |
| | 1:2:2 | 1.0 | 1.0 | 111.66 ± 1.73 |
| | 1:1:0.5 | 1.0 | 1.0 | 114.60 ± 1.39 |
| | 1:0.5:1 | 1.0 | 1.0 | 112.24 ± 2.03 |
| | 1:0.5:0.5 | 1.0 | 1.0 | 114.84 ± 3.51 |
| | 1:1:3 | 1.0 | 1.0 | 112.02 ± 2.65 |
| | 1:3:1 | 1.0 | 1.0 | 113.82 ± 2.11 |
| | 1:3:3 | 1.0 | 1.0 | 112.51 ± 2.67 |
| | 1:1:0.33 | 1.0 | 1.0 | 109.39 ± 1.01 |
| | 1:0.33:1 | 1.0 | 1.0 | 115.92 ± 1.73 |
| | 1:0.33:0.33 | 1.0 | 1.0 | 115.92 ± 2.94 |
| | 1:1:4 | 1.0 | 1.0 | 112.51 ± 3.39 |
| | 1:4:1 | 1.0 | 1.0 | 113.73 ± 2.78 |
| | 1:4:4 | 1.0 | 1.0 | 113.94 ± 2.77 |
| | 1:1:0.25 | 1.0 | 1.0 | 113.39 ± 2.71 |
| | 1:0.25:1 | 1.0 | 1.0 | 112.78 ± 1.79 |
| | 1:0.25:0.25 | 1.0 | 1.0 | 113.77 ± 1.86 |
| | 1:1:5 | 1.0 | 1.0 | 110.71 ± 2.87 |
| | 1:5:1 | 1.0 | 1.0 | 113.86 ± 2.75 |
| | 1:5:5 | 1.0 | 1.0 | 113.28 ± 2.86 |
| | 1:1:0.2 | 1.0 | 1.0 | 112.75 ± 1.11 |

TABLE 26-continued

Reactive oxygen species (ROS) generation reduction effect of the extract of the mixture of Moutan Root Bark, *Angelica Dahurica* Root and *Bupleurum* Root according to different mixing ratios

| Mixed composition | Treatment | | | |
|---|---|---|---|---|
| | Mixing ratio* | Conc. (μg/ml) | Inducer (MPP+, mM) | DCF-DA-ROS (% of Control) |
| | 1:0.2:1 | 1.0 | 1.0 | 115.85 ± 1.01 |
| | 1:0.2:0.2 | 1.0 | 1.0 | 112.72 ± 3.66 |

*Mixing ratio of the extract of the mixture is weight ratio of Moutan Root Bark:*Angelica Dahurica* Root:*Bupleurum* Root(w:w:w).

Experimental Example 6: Evaluation of Intracellular Efficacy of Mixture Extract of Moutan Root Bark, Angelica Dahurica Root and Bupleurum Root (1:1:1, w:w:w) According to Ethanol Concentration <6-1> Changes of active components in mixture extract of Moutan Root Bark, Angelica Dahurica Root and Bupleurum Root (1:1:1, w:w:w) according to ethanol concentration The changes of active components in the extract of the mixture of Moutan Root Bark, Angelica Dahurica Root and Bupleurum Root according to ethanol concentration were investigated.

Particularly, the extraction solvent ethanol was added to the mixture of Moutan Root Bark, Angelica Dahurica Root and Bupleurum Root (1:1:1, w:w:w) at different concentrations of 10%, 30%, 50%, 70%, and 90%, followed by extraction by the same manner as described in Example <5-1>. The obtained mixture extracts proceeded to quantitative analysis by using HPLC.

As a result, as shown in Table 27, the mixed 90% ethanol extract of Moutan Root Bark, Angelica Dahurica Root and Bupleurum Root (1:1:1) displayed the highest contents of paeonol, paeoniflorin, saikosaponin A, and imperatorin (Table 27).

TABLE 27

Changes of active components in mixture extract of Moutan Root Bark, *Angelica Dahurica* Root and *Bupleurum* Root (1:1:1, w:w:w) according to ethanol concentration

| Ethanol concentration (%) | Index component content (%) | | | |
|---|---|---|---|---|
| | paeonol | paeoniflorin | imperatorin | Saikosaponin A |
| 10 | 1.2 | 2.7 | 0.0 | 0.1 |
| 30 | 2.5 | 2.2 | 0.2 | 1.0 |
| 50 | 4.2 | 2.7 | 0.4 | 1.8 |
| 70 | 4.4 | 2.2 | 0.6 | 1.5 |
| 90 | 4.9 | 4.2 | 1.1 | 1.7 |

<6-2> Recovery effect of mixture extract of Moutan Root Bark, Angelica Dahurica Root and Bupleurum Root (1:1:1, w:w:w) on mitochondrial activity according to ethanol concentration in Parkinson's disease cell model To investigate the recovery effect of the extract of the mixture of Moutan Root Bark, Angelica Dahurica Root and Bupleurum Root (1:1:1) on mitochondrial activity according to ethanol concentration in Parkinson's disease cell model, the mitochondrial activity index was examined in Parkinson's disease cell model.

Particularly, SH-SY5Y, the human neuroblastoma cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of $1 \times 10^5$ cells/well. The cells were treated with the mixed ethanol extracts of Moutan Root Bark and Angelica Dahurica Root (1:1:1) prepared in Example <5-1> by using different concentrations of ethanol at the concentration of 1 μg/ml, followed by culture for 4 hours. Upon completion of the culture, the Parkinson's disease cell model was constructed by the same manner as described in Experimental Example <4-1>. Then, the cell survival rate was measured by the same manner as described in Experimental Example <1-1> using calcein. The cell survival rate that was increased or decreased compared with that of the normal control cells not-treated with the extract or its active component above and instead treated with DMSO was calculated and presented as percentage (%). The negative control was treated with 1 mM MPP+ alone, resulting in the construction of Parkinson's disease cell model that had not been treated with the extract or the active component thereof. Then, the cell survival rate was also measured, either increased or decreased, by comparing with that of the normal control by the same manner as described above.

As a result, as shown in Table 28, the mitochondrial activity reduced by 1-methyl-4-phenylpyridinium was recovered as much as 95.02% by the normal control after the treatment of the mixed 90% ethanol extract of Moutan Root Bark, Angelica Dahurica Root and Bupleurum Root (1:1:1), which was the highest (Table 28).

TABLE 28

Effect of mixture extract of Moutan Root Bark, *Angelica Dahurica* Root and *Bupleurum* Root (1:1:1, w:w:w) on cell survival rate according to ethanol concentration

| Treatment | Treatment | | | |
|---|---|---|---|---|
| Treatment substance | Ethanol concentration (%) | Conc. (μg/ml) | Inducer (MPP+, mM) | Cell survival rate (% of Control) |
| Normal control | — | — | — | 100.00 ± 2.05 |
| Negative control | — | — | 1.0 | 53.73 ± 2.39 |
| Moutan Root Bark + *Angelica Dahurica* Root + *Bupleurum* Root (1:1:1; w:w:w) | 10 | 1.0 | 1.0 | 88.22 ± 1.47 |
| | 30 | 1.0 | 1.0 | 89.85 ± 1.55 |
| | 50 | 1.0 | 1.0 | 90.11 ± 1.14 |
| | 70 | 1.0 | 1.0 | 92.39 ± 1.74 |
| | 90 | 1.0 | 1.0 | 95.02 ± 2.61 |

<6-3> Recovery Effect of Mixture Extract of Moutan Root Bark, Angelica Dahurica Root and Bupleurum Root (1:1:1, w:w:w) on the Loss of ATP According to Ethanol Concentration in Parkinson's Disease Cell Model To investigate the recovery effect of the extract of the mixture of Moutan Root Bark, Angelica Dahurica Root and Bupleurum Root (1:1:1, w:w:w) on the mitochondrial functional damage according to the ethanol concentration in Parkinson's disease cell model, ATP assay was performed to confirm the recovery effect on the loss of intracellular ATP.

Particularly, SH-SY5Y, the human neuroblastoma cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of $1 \times 10^5$ cells/well. The cells were treated with the mixed ethanol extracts of Moutan Root Bark and Angelica Dahurica Root (1:1:1) prepared in Example <5-1> by using different concentrations of ethanol at the concentration of 1 μg/ml, followed by culture for 4 hours. Upon completion of the culture, the Parkinson's disease cell model was constructed by the same manner as described in Experimental Example <4-1>. Then, the intracellular ATP level was measured by the same manner as described in Experimental Example <1-3>. The increase or decrease of the intracellular ATP level was calculated by comparing that of the normal control which had not been treated with the extract or the active component but treated with DMSO alone. The intracellular ATP level that was increased or decreased compared with that of the normal control cells not-treated with the extract or its active component above and instead treated with DMSO was calculated and presented as percentage (%). The negative control was treated with 1 mM MPP+ alone, resulting in the construction of Parkinson's disease cell model that had not been treated with the extract or the active component thereof. Then, the recovery effect on the intracellular ATP level was investigated by the same manner as described above.

As a result, as shown in Table 29, the mitochondrial activity reduced by 1-methyl-4-phenylpyridinium was recovered as much as 96.45% by the normal control after the treatment of the mixed 90% ethanol extract, which was the highest (Table 29).

TABLE 29

Recovery effect of mixture extract of Moutan Root Bark, *Angelica Dahurica* Root and *Bupleurum* Root (1:1:1, w:w:w) on the loss of intracellular ATP according to ethanol concentration

| Treatment substance | Treatment | | | Intracellular ATP (% of Control) |
|---|---|---|---|---|
| | Ethanol concentration (%) | Conc. (μg/ml) | Inducer (MPP+, mM) | |
| Normal control | — | — | — | 100.00 ± 1.34 |
| Negative control | — | — | 1.0 | 59.28 ± 2.45 |
| Moutan Root Bark + *Angelica Dahurica* Root + *Bupleurum* Root (1:1:1; w:w:w) | 10 | 1.0 | 1.0 | 89.31 ± 2.33 |
| | 30 | 1.0 | 1.0 | 89.34 ± 1.68 |
| | 50 | 1.0 | 1.0 | 90.14 ± 1.47 |
| | 70 | 1.0 | 1.0 | 93.81 ± 2.59 |
| | 90 | 1.0 | 1.0 | 96.45 ± 2.41 |

<6-4> Reduction of Reactive Oxygen Species (ROS) Generation in Parkinson's Disease Cell Model by the Mixed Ethanol Extract of Moutan Root Bark, Angelica Dahurica Root and Bupleurum Root (1:1:1) According to Ethanol Concentration To investigate the reduction effect of the mixed ethanol extract of Moutan Root Bark, Angelica Dahurica Root and Bupleurum Root (1:1:1) on the ROS generation caused by mitochondrial functional damage in Parkinson's disease cell model according to ethanol concentration, the concentration of intracellular ROS was measured by using 2',7'-dichlorofluoroscein diacetate (DCF-DA).

Particularly, BV2, the mouse microglial cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of $1 \times 10^5$ cells/well. The cells were treated with the various mixed ethanol extracts of Moutan Root Bark and Angelica Dahurica Root having different mixing ratios prepared in Example 5 by using different concentrations of ethanol at the concentration of 1 μg/ml, followed by culture for 4 hours. Upon completion of the culture, the Parkinson's disease cell model was constructed by the same manner as described in Experimental Example <4-1>. Then, ROS was quantified based on the ratio of DCF-DA/bisbenzimide by the same manner as described in Experimental Example <3-5>. The level of ROS, either increased or decreased, was compared with that of the normal control not treated with the extract or the active component thereof but treated with DMSO, and the results were presented as % by the normal control. The negative control Parkinson's disease cell model was constructed by the treatment of 1 mM MPP+ alone but not treated with the extract or the active component thereof. Then, the ROS generation reduction effect was investigated by the same manner as described above.

As a result, as shown in Table 30, the mitochondrial activity reduced by 1-methyl-4-phenylpyridinium was recovered as much as 106.06% by the normal control after the treatment of the mixed 90% ethanol extract of Moutan Root Bark, Angelica Dahurica Root and Bupleurum Root (1:1:1), which was the highest (Table 30).

TABLE 30

Reactive oxygen species (ROS) generation reduction effect of mixture extract of Moutan Root Bark, *Angelica Dahurica* Root and *Bupleurum* Root (1:1:1, w:w:w) according to ethanol concentration

| Treatment substance | Treatment | | | DCF-DA-ROS (% of Control) |
|---|---|---|---|---|
| | Ethanol concentration (%) | Conc. (μg/ml) | Inducer (MPP+, mM) | |
| Normal control | — | — | — | 100.00 ± 1.05 |
| Negative control | — | — | 1.0 | 161.71 ± 1.88 |
| Moutan Root Bark + *Angelica Dahurica* Root + *Bupleurum* Root (1:1:1; w:w:w) | 10 | 1.0 | 1.0 | 111.22 ± 1.58 |
| | 30 | 1.0 | 1.0 | 110.67 ± 2.23 |
| | 50 | 1.0 | 1.0 | 108.27 ± 2.98 |
| | 70 | 1.0 | 1.0 | 108.75 ± 2.24 |
| | 90 | 1.0 | 1.0 | 105.06 ± 1.55 |

Experimental Example 7: Evaluation of Intracellular Efficacy of Mixture Extract of Moutan Root Bark, Angelica Dahurica Root and Bupleurum Root According to Types of Extraction Solvent <7-1> Recovery Effect of Mixture Extract of Moutan Root Bark, Angelica Dahurica Root and Bupleurum Root on Mitochondrial Activity in Parkinson's Disease Cell Model According to Types of Extraction Solvent To investigate the recovery effect of the extract of the mixture of Moutan Root Bark, Angelica Dahurica Root and Bupleurum Root on mitochondrial activity in Parkinson's disease cell model according to types of extraction solvent, the mitochondrial activity index was examined in Parkinson's disease cell model.

Particularly, SH-SY5Y, the human neuroblastoma cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of $1 \times 10^5$ cells/well. The cells were treated with the mixed ethanol extracts of Moutan Root Bark and Angelica Dahurica Root (1:1:1) prepared in Example <5-1> by using different concentrations of ethanol at the concentration of 1 μg/ml, followed by culture for 4 hours. Upon completion of the culture, the Parkinson's disease cell model was constructed by the same manner as described in Experimental Example <4-1>. Then, the cell survival rate was measured by the same manner as described in Experimental Example <1-1> using calcein. The cell survival rate that was increased or decreased compared with that of the normal control cells not-treated with the extract or its active component above and instead treated with DMSO was calculated and presented as percentage (%). The negative control was treated with 1 mM MPP+ alone, resulting in the construction of Parkinson's disease cell model that had not been treated with the extract or the active component thereof. Then, the cell survival rate was also measured, either increased or decreased, by comparing with that of the normal control by the same manner as described above.

As a result, as shown in Table 31, the mitochondrial activity reduced by 1-methyl-4-phenylpyridinium was recovered as much as 93.09% by the normal control after the treatment of the mixed 90% ethanol extract of Moutan Root Bark, Angelica Dahurica Root and Bupleurum Root, which was the highest (Table 31).

TABLE 31

Effect of mixture extract of Moutan Root Bark, *Angelica Dahurica* Root and *Bupleurum* Root on cell survival rate according to types of extraction solvent

| Treatment substance | Treatment Extraction solvent & conc. (%) | Conc. (μg/ml) | Inducer (MPP+, mM) | Cell survival rate (% of Control) |
|---|---|---|---|---|
| Normal control | — | — | — | 100.00 ± 1.22 |
| Negative control | — | — | 1.0 | 55.29 ± 1.06 |
| Moutan Root Bark + *Angelica Dahurica* Root + *Bupleurum* Root (1:1:1; w:w:w) | Water | 1.0 | 1.0 | 87.80 ± 2.83 |
| | 90% ethanol | 1.0 | 1.0 | 93.09 ± 1.52 |
| | 90% methanol | 1.0 | 1.0 | 87.15 ± 1.36 |
| | 90% butanol | 1.0 | 1.0 | 89.76 ± 2.95 |

<7-2> Recovery Effect of Mixture Extract of Moutan Root Bark, Angelica Dahurica Root and Bupleurum Root on the Loss of Intracellular ATP in Parkinson's Disease Cell Model According to Types of Extraction Solvent To investigate the recovery effect of the extract of the mixture of Moutan Root Bark, Angelica Dahurica Root and Bupleurum Root on the mitochondrial functional damage in Parkinson's disease cell model according to types of extraction solvent, ATP assay was performed to confirm the recovery effect on the loss of intracellular ATP.

Particularly, SH-SY5Y, the human neuroblastoma cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of $1 \times 10^5$ cells/well. The cells were treated with the mixture extracts of Moutan Root Bark and Angelica Dahurica Root (1:1:1) prepared in Example 5 by using different extraction solvents at the concentration of 1 μg/ml, followed by culture for 4 hours. Upon completion of the culture, the Parkinson's disease cell model was constructed by the same manner as described in Experimental Example <4-1>. Then, the intracellular ATP level was measured by the same manner as described in Experimental Example <1-3>. The intracellular ATP level that was increased or decreased compared with that of the normal control cells not-treated with the extract or its active component above and instead treated with DMSO was calculated and presented as percentage (%). The negative control was treated with 1 mM MPP+ alone, resulting in the construction of Parkinson's disease cell model that had not been treated with the extract or the active component thereof. Then, the recovery effect on the intracellular ATP level was investigated by the same manner as described above.

As a result, as shown in Table 32, the mitochondrial activity reduced by 1-methyl-4-phenylpyridinium was recovered as much as 95.90% by the normal control after the treatment of the mixed 90% ethanol extract, which was the highest (Table 32).

TABLE 32

Recovery effect of mixture extract of Moutan Root Bark, *Angelica Dahurica* Root and *Bupleurum* Root on the loss of intracellular ATP according to types of extraction solvent

| Treatment substance | Treatment Extraction solvent & conc. (%) | Conc. (μg/ml) | Inducer (MPP+, mM) | Intracellular ATP (% of Control) |
|---|---|---|---|---|
| Normal control | — | — | — | 100.00 ± 1.78 |
| Negative control | — | — | 1.0 | 54.10 ± 1.69 |
| Moutan Root Bark + *Angelica Dahurica* Root + *Bupleurum* Root (1:1:1; w:w:w) | Water | 1.0 | 1.0 | 89.21 ± 2.34 |
| | 90% ethanol | 1.0 | 1.0 | 95.90 ± 3.64 |
| | 90% methanol | 1.0 | 1.0 | 90.87 ± 1.86 |
| | 90% butanol | 1.0 | 1.0 | 88.97 ± 1.78 |

<7-3> Reduction of Reactive Oxygen Species (ROS) Generation in Parkinson's Disease Cell Model by Mixture Extract of Moutan Root Bark, Angelica Dahurica Root and Bupleurum Root According to Types of Extraction Solvent To investigate the reduction effect of the extract of the mixture of Moutan Root Bark, Angelica Dahurica Root and Bupleurum Root on the ROS generation caused by mitochondrial functional damage in Parkinson's disease cell model according to types of extraction solvent, the concentration of intracellular ROS was measured by using 2',7'-dichlorofluoroscein diacetate (DCF-DA).

Particularly, BV2, the mouse microglial cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of $1 \times 10^5$ cells/well. The cells were treated with the mixture extracts of Moutan Root Bark and Angelica Dahurica Root prepared in Example 5 by using different extraction solvents at the concentration of 1 μg/ml, followed by culture for 4 hours. Upon completion of the culture, the Parkinson's disease cell model was constructed by the same manner as described in Experimental Example <4-1>. Then, ROS was quantified based on the ratio of DCF-DA/bisbenzimide by the same manner as described in Experimental Example <3-5>. The level of ROS, either increased or decreased, was compared with that of the normal control not treated with the extract or the active component thereof but treated with DMSO, and the results were presented as % by the normal control. The negative control Parkinson's disease cell model was constructed by the treatment of 1 mM MPP+ alone but not treated with the extract or the active component thereof. Then, the ROS generation reduction effect was investigated by the same manner as described above.

As a result, as shown in Table 33, the mitochondrial activity reduced by 1-methyl-4-phenylpyridinium was recovered as much as 106.82% by the normal control after the treatment of the mixed 90% ethanol extract of Moutan Root Bark, Angelica Dahurica Root and Bupleurum Root, which was the highest (Table 33).

TABLE 33

Reactive oxygen species (ROS) generation reduction effect of mixture extract of Moutan Root Bark, *Angelica Dahurica* Root and *Bupleurum* Root according to types of extraction solvent

| Treatment substance | Extraction solvent & conc. (%) | Conc. (μg/ml) | Inducer (MPP+, mM) | DCF-DA-ROS (% of Control) |
|---|---|---|---|---|
| Normal control | — | — | — | 100.00 ± 5.55 |
| Negative control | — | — | 1.0 | 161.78 ± 7.06 |
| Moutan Root Bark + *Angelica Dahurica* Root + *Bupleurum* Root (1:1:1; w:w:w) | Water | 1.0 | 1.0 | 112.71 ± 3.28 |
| | 90% ethanol | 1.0 | 1.0 | 106.82 ± 2.22 |
| | 90% methanol | 1.0 | 1.0 | 110.45 ± 1.46 |
| | 90% butanol | 1.0 | 1.0 | 109.47 ± 2.79 |

Experimental Example 8: Evaluation of Intracellular Efficacy of Mixture Extract of Moutan Root Bark, Angelica Dahurica Root and Bupleurum Root <8-1> Improvement of Mitochondrial Activity by Mixture Extract of Moutan Root Bark, Angelica Dahurica Root and Bupleurum Root To evaluate the intracellular efficacy of the extract of the mixture of Moutan Root Bark, Angelica Dahurica Root and Bupleurum Root of the present invention, the expression levels of TFAM and H2AX, the representative markers for mitochondria biogenesis, in human neuroblastoma cells were measured by Western blotting.

Particularly, SH-SY5Y, the human neuroblastoma cell line, was inoculated in DMEM/F12 (1:1) supplemented with 10% FBS, followed by culture in a 37° C., 5% $CO_2$/95% air ($O_2$) incubator. Then, the cultured cells were transferred into a serum free medium at the density of $1 \times 10^5$ cells/well. The cells were treated with the lyophilisate of the mixed 90% ethanol extract of Moutan Root Bark and Angelica Dahurica Root (1:1:1) prepared in Example <5-1> at the concentration of 1.0 μg/ml, followed by culture for 4 hours. Upon completion of the culture, the Parkinson's disease cell model was constructed by the same manner as described in Experimental Example <4-1>. Then, the pre-treated cells were treated with 0.5 mM MPP+, followed by culture for 24 hours to induce malfunction of mitochondrial. Intracellular protein was obtained from the cells, followed by Western blotting to investigate the phosphorylation of STAT protein (S727 and Y705), the phosphorylation of AKT protein (T308 and S473), and the expression levels of TH, TFAM, and H2AX proteins. β-actin was used as the control protein for the comparison of the expression. The normal control was not treated with the extract of the invention but treated with DMSO. The negative control was treated with 0.5 mM MPP+ alone to cause mitochondrial damage and at this time the negative control was not treated with the extract of the invention.

As a result, as shown in Table 34, when the mixed 90% ethanol extract of Moutan Root Bark, Angelica Dahurica Root and Bupleurum Root was treated to the cells at the concentration of 1.0 μg/ml, the phosphorylation of STAT protein (Y705), the phosphorylation of AKT protein (T308 and S473), and the expression levels of TH, TFAM, and H2AX were recovered almost to the normal level (Table 34).

TABLE 34

Protein expression levels of mitochondrial activity related genes according to mixture extract of Moutan Root Bark, *Angelica Dahurica* Root and *Bupleurum* Root

| Treatment substance | Conc. (μg/ml) | Inducer Conc. (MPP+, 0.5 mM) | pSTAT(S727)/ β-actin |
|---|---|---|---|
| Normal control | — | — | 100.00 ± 2.04 |
| Negative control | — | 30 | 95.24 ± 5.27 |
| Moutan Root Bark + *Angelica Dahurica* Root + *Bupleurum* Root(1:1:1, w:w:w) | 1 | 30 | 106.82 ± 2.98 |

| Treatment substance | Conc. (μg/ml) | Inducer Conc. (MPP+, 0.5 mM) | pSTAT(Y705)/ β-actin |
|---|---|---|---|
| Normal control | — | — | 100.00 ± 3.18 |
| Negative control | — | 30 | 7.41 ± 0.91 |
| Moutan Root Bark + *Angelica Dahurica* Root + *Bupleurum* Root(1:1:1, w:w:w) | 1 | 30 | 42.54 ± 5.33 |

| Treatment substance | Conc. (μg/ml) | Inducer Conc. (MPP+, 0.5 mM) | STAT3/ β-actin |
|---|---|---|---|
| Normal control | — | — | 100.00 ± 2.86 |
| Negative control | — | 30 | 101.27 ± 4.05 |
| Moutan Root Bark + *Angelica Dahurica* Root + *Bupleurum* Root(1:1:1, w:w:w) | 1 | 30 | 99.39 ± 2.02 |

| Treatment substance | Conc. (μg/ml) | Inducer Conc. (MPP+, 0.5 mM) | pAKT(T308)/ β-actin |
|---|---|---|---|
| Normal control | — | — | 100.00 ± 3.08 |
| Negative control | — | 30 | 10.45 ± 0.82 |
| Moutan Root Bark + *Angelica Dahurica* Root + *Bupleurum* Root(1:1:1, w:w:w) | 1 | 30 | 98.42 ± 3.07 |

| Treatment substance | Conc. (μg/ml) | Inducer Conc. (MPP+, 0.5 mM) | pAKT(S473)/ β-actin |
|---|---|---|---|
| Normal control | — | — | 100.00 ± 2.10 |
| Negative control | — | 30 | 8.13 ± 0.72 |

TABLE 34-continued

Protein expression levels of mitochondrial activity related genes according to mixture extract of Moutan Root Bark, *Angelica Dahurica* Root and *Bupleurum* Root

| Moutan Root Bark + *Angelica Dahurica* Root + *Bupleurum* Root(1:1:1, w:w:w) | 1 | 30 | 95.32 ± 3.09 |

| Treatment substance | Conc. (μg/ml) | Inducer Conc. (MPP+, 0.5 mM) | AKT1/β-actin |
|---|---|---|---|
| Normal control | — | — | 100.00 ± 2.06 |
| Negative control | — | 30 | 96.21 ± 3.07 |
| Moutan Root Bark + *Angelica Dahurica* Root + *Bupleurum* Root(1:1:1, w:w:w) | 1 | 30 | 99.41 ± 2.02 |

| Treatment substance | Conc. (μg/ml) | Inducer Conc. (MPP+, 0.5 mM) | TH/β-actin |
|---|---|---|---|
| Normal control | — | — | 100.00 ± 3.06 |
| Negative control | — | 30 | 9.28 ± 1.01 |
| Moutan Root Bark + *Angelica Dahurica* Root + *Bupleurum* Root(1:1:1, w:w:w) | 1 | 30 | 97.38 ± 4.37 |

| Treatment substance | Conc. (μg/ml) | Inducer Conc. (MPP+, 0.5 mM) | TFAM/β-actin |
|---|---|---|---|
| Normal control | — | — | 100.00 ± 2.97 |
| Negative control | — | 30 | 15.83 ± 2.12 |
| Moutan Root Bark + *Angelica Dahurica* Root + *Bupleurum* Root(1:1:1, w:w:w) | 1 | 30 | 97.21 ± 3.05 |

| Treatment substance | Conc. (μg/ml) | Inducer Conc. (MPP+, 0.5 mM) | H2AX/β-actin |
|---|---|---|---|
| Normal control | — | — | 100.00 ± 3.07 |
| Negative control | — | 30 | 4.11 ± 0.72 |
| Moutan Root Bark + *Angelica Dahurica* Root + *Bupleurum* Root(1:1:1, w:w:w) | 1 | 30 | 89.32 ± 2.73 |

<8-2> Expression of Endoplasmic Reticulum Stress Marker Gene According to Mixture Extract of Moutan Root Bark, Angelica Dahurica Root and Bupleurum Root To investigate the effect of the extract of the mixture of Moutan Root Bark, Angelica Dahurica Root and Bupleurum Root of the present invention on the recovery of endoplasmic reticulum stress, the expression levels of the endoplasmic reticulum stress marker genes GRP78 and XBP1p were measured.

Particularly, SH-SY5Y cells were cultured by the same manner as described in Experimental Example <2-2>, and endoplasmic reticulum stress was induced. Then, RT-PCR was performed with the cells having endoplasmic reticulum stress by the same manner as described in Experimental Example <1-4>, followed by electrophoresis to investigate the expression levels of GRP78 and XBP1p genes on 1.5% agarose gel under UV. The normal control was not treated with the extract of the invention but treated with DMSO alone. The negative control was not treated with the extract or the active component but treated with 0.5 μg/ml of thapsigargin alone to induce endoplasmic reticulum stress. Then, the expression of the endoplasmic reticulum stress marker gene was confirmed by the same manner as described above.

As a result, as shown in Table 35 and Table 36, the expression levels of the endoplasmic reticulum stress marker genes GRP78 and XBP1p were recovered to the normal level in the cells having endoplasmic reticulum stress induced therein by the treatment of the mixed 90% ethanol extract of Moutan Root Bark, Angelica Dahurica Root and Bupleurum Root at the concentration of 1.0 μg/ml (Tables 35 and 36).

TABLE 35

Expression of GRP78 mRNA according to mixture extract of Moutan Root Bark, *Angelica Dahurica* Root and *Bupleurum* Root in cells having endoplasmic reticulum stress induced by thapsigargin

| | | Inducer | |
|---|---|---|---|
| Treatment substance | Conc. (μg/ml) | (thapsigargin, μg/ml) | GRP78/18S mRNA |
| Normal control | — | — | 2.01 ± 0.04 |
| Negative control | — | 0.5 | 100.0 ± 3.05 |
| Moutan Root Bark + *Angelica Dahurica* Root + *Bupleurum* Root 1:1:1 (w:w:w) mixture extract | 1 | 0.5 | 3.12 ± 0.02 |

TABLE 36

Expression of XBP1p mRNA according to mixture extract of *Moutan* Root Bark, *Angelica Dahurica* Root and *Bupleurum* Root in cells having endoplasmic reticulum stress induced by thapsigargin

| | | Inducer | |
|---|---|---|---|
| Treatment substance | Conc. (μg/ml) | (thapsigargin, μg/ml) | XBP1P/18S mRNA |
| Normal control | — | — | 3.46 ± 0.03 |
| Negative control | — | 0.5 | 100.0 ± 2.79 |
| *Moutan* Root Bark + *Angelica Dahurica* Root + *Bupleurum* Root 1:1:1 (w:w:w) mixture extract | 1 | 0.5 | 2.98 ± 0.01 |

<8-3> Anti-Inflammatory Effect and Anti-Oxidative Effect of Mixture Extract of Moutan Root Bark, Angelica Dahurica Root and Bupleurum Root To investigate the recovery effect of the extract of the mixture of Moutan Root Bark, Angelica Dahurica Root and Bupleurum Root of the present invention on inflammatory response, Griess method was performed to measure the concentration of nitrite/nitrate ($NO_x$) in the cell culture medium and the concentration of intracellular ROS by using 2',7'-dichlorofluorocein diacetate (DCF-DA).

Particularly, BV2 cells were cultured by the same manner as described in Experimental Example <3-1>, and inflammatory response was induced. Then, 100 μl of the cell culture medium was obtained, to which 100 μl of Griess reagent comprising hydrochloric acid containing 5% sulfanilamide and 2% naphthylethylenediamine was added, followed by reaction in a dark room for 30 minutes. Upon completion of the reaction, $OD_{540}$ was measured with an EISA microplate reader (Versamax, USA). The concentration of nitric oxide in the medium was calculated using the standard calibration curve of sodium nitrite. To measure the ROS concentration, the cells were treated with 1 μM DCF-DA and 0.05 μM bisbenzimide (Hoechst 33342), followed by staining at 37° C. for 1 hour. After the staining, the fluorescence intensity of DCF-DA was measured at 485 nm/535 nm, and the fluorescence intensity of bisbenzimide was measured at 335 nm/460 nm. Based on the ratio of DCF-DA/bisbenzimide, ROS was quantified. The amount of ROS, either increased or decreased, was compared with that of the normal control not treated with the extract but treated with DMSO, and the results were presented as %. The negative control was treated with 100 ng/ml of LPS alone to induce inflammatory response but not treated with the extract or the active component thereof. Then, the nitric oxide concentration reduction effect and the ROS concentration reduction effect were investigated by the same manner as described above.

As a result, as shown in table 37, the extract of the mixture of Moutan Root Bark, Angelica Dahurica Root and Bupleurum Root of the present invention was confirmed to have the effect of reducing the LPS mediated NO generation (Table 37) and the effect of reducing the DCF-DA mediated ROS generation caused by inflammatory response and stress (Table 38).

TABLE 37

Nitric oxide (NO) concentration reduction effect of mixture extract of *Moutan* Root Bark, *Angelica Dahurica* Root and *Bupleurum* Root

| Treatment substance | Conc. (μg/ml) | Inducer (LPS, ng/ml) | NO (mM) |
|---|---|---|---|
| Normal control | — | — | 46.79 ± 3.45 |
| Negative control | — | 100 | 200.32 ± 10.24 |
| *Moutan* Root Bark + *Angelica Dahurica* Root + *Bupleurum* Root 1:1:1 (w:w:w) mixture extract | 1 | 100 | 42.67 ± 2.09 |

TABLE 38

Reactive oxygen species (ROS) generation reduction effect of mixture extract of *Moutan* Root Bark, *Angelica Dahurica* Root and *Bupleurum* Root

| Treatment substance | Conc. (μg/ml) | Inducer (LPS, ng/ml) | DCF-DA-ROS (% of control) |
|---|---|---|---|
| Normal control | — | — | 100.24 ± 6.79 |
| Negative control | — | 100 | 134.09 ± 19.13 |
| *Moutan* Root Bark + *Angelica Dahurica* Root + *Bupleurum* Root 1:1:1 (w:w:w) mixture extract | 1 | 100 | 115.83 ± 8.09 |

Experimental Example 9: Therapeutic Effect of Mixture Extract of Moutan Root Bark, Angelica Dahurica Root and Bupleurum Root on Parkinson's Disease In Vivo <9-1> Construction of Parkinson's Disease Animal Model: MPTP-Induced Parkinson's Disease Mouse Model As shown in FIG. 1, Parkinson's disease animal model was constructed in order to investigate the in vivo therapeutic effect of the extract of the mixture of Moutan Root Bark, Angelica Dahurica Root and Bupleurum Root of the present invention on Parkinson's disease (FIG. 1).

Particularly, 5 week old C57BL/6 male mice (weight: approximately 19~22 g) were distributed, followed by adaptation in an animal laboratory of Dong-A ST Research Division for at least 1 week. At this time, the indoor temperature was regulated at 22±2° C. and the humidity was controlled at 53±3%. The light and dark cycle was set at 12 hr/12 hr. Water and feeds were provided freely. After the adaptation, mice were grouped into 5 groups and each group was allocated with 6 mice. The lyophilisate of the mixed 90% ethanol extract of Moutan Root Bark, Angelica Dahurica Root and Bupleurum Root (1:1:1) prepared in Example <5-1> was dissolved in 3% HPMC, which was orally administered (per oral, p.o.) to the mice at the dose of 1, 3, and 10 mg/kg once a day for 14 days. Then, the mice were administered (intraperitoneal, i.p.) with 1-methyl-4-phenyl-1,2,3,6-tetrahydropyridine (MPTP) at the dose of 30 mg/kg 3 hours after the oral administration for 5 days from the 8th day of the experiment, resulting in the construction of Parkinson's disease animal model. The normal control was administered with 3% HPMC at the dose of 5 ml/kg without the mixture extract, and then MPTP free PBS was intraperitoneally administered thereafter.

<9-2> Improvement of Motor Coordination in MPTP-Induced Parkinson's Disease Mouse Model by Mixture Extract of Moutan Root Bark, Angelica Dahurica Root and Bupleurum Root To investigate the in vivo therapeutic effect of the extract of the mixture of Moutan Root Bark, Angelica Dahurica Root and Bupleurum Root of the present invention on Parkinson's disease, behavioral test (Pole test, Rotarod test) was performed with the MPTP-induced Parkinson's disease mouse model after the administration of the extract of the mixture above.

Particularly, Parkinson's disease mouse model was constructed in Experimental Example <8-1>. The animal model, 14 days after the construction, was placed on top of the pole having the rough surface (diameter: 8 mm, height: 55 cm). Time for the mouse to move down completely was measured every 30 seconds, which was defined as time to turn (T-turn), and time for the mouse to arrive on the floor was measured, which was defined as locomotion activity time (T-LA). The animal was placed on the wheel whose rpm could be regulated. Time for the animal to fall down was measured (latency to fall). The normal control was treated with the vehicle of 3% HPMC. The negative control was intraperitoneally administered (i.p.) with MPTP at the dose of 30 mg/kg for 5 days, but not treated with the extract of the mixture thereafter. Then, Pole test was performed with the controls to measure the T-turn and T-LA and rotarod test was performed to measure the latency to fall by the same manner as described above.

As a result, as shown in Table 39 and Table 40, compared with the normal control group treated with the vehicle, T-turn and T-LA were significantly increased in the negative control treated with MPTP alone. In the meantime, in the Parkinson's disease mouse model treated with the mixed 90% ethanol extract of Moutan Root Bark, Angelica Dahurica Root and Bupleurum Root, T-turn and T-LA were reduced (Table 39 and Table 40). As shown in Table 41, it was confirmed from the Rotarod test that latency to fall was significantly reduced in the negative control treated with MPTP alone, while latency to fall was increased in the Parkinson's disease mouse model treated with the mixed 90% ethanol extract of Moutan Root Bark, Angelica Dahurica Root and Bupleurum Root. Therefore, it was confirmed that the motor coordination was recovered in the Parkinson's disease mouse model by the treatment of the mixed 90% ethanol extract of Moutan Root Bark, Angelica Dahurica Root and Bupleurum Root (Tables 39~41).

TABLE 39

Decrease of T-turn by mixture extract of *Moutan* Root Bark, *Angelica Dahurica* Root and *Bupleurum* Root in MPTP-induced Parkinson's disease mouse model

| Treatment substance | Extract dose (mg/kg*) | Inducer dose (MPTP, mg/kg 5x, ip) | T-turn(s) |
|---|---|---|---|
| Normal control | — | — | 1.96 ± 0.17 |
| Negative control | — | 30 | 4.79 ± 0.41 |
| *Moutan* Root Bark + *Angelica Dahurica* Root + *Bupleurum* Root 1:1:1 (w:w:w) mixture extract | 1<br>3<br>10 | 30<br>30<br>30 | 4.06 ± 0.36<br>3.74 ± 0.42<br>2.84 ± 0.19 |

*The dose represents the mass (mg) of the extract of the mixture treated per kg of body weight of the animal model mouse

TABLE 40

Decrease of T-LA by mixture extract of *Moutan* Root Bark, *Angelica Dahurica* Root and *Bupleurum* Root in MPTP-induced Parkinson's disease mouse model

| Treatment substance | Extract dose (mg/kg*) | Inducer dose (MPTP, mg/kg 5x, ip) | T-turn(s) |
|---|---|---|---|
| Normal control | — | — | 4.63 ± 0.37 |
| Negative control | — | 30 | 8.27 ± 0.18 |
| *Moutan* Root Bark + *Angelica Dahurica* Root + *Bupleurum* Root 1:1:1 (w:w:w) mixture extract | 1<br>3<br>10 | 30<br>30<br>30 | 7.93 ± 0.63<br>7.27 ± 0.27<br>6.43 ± 0.44 |

*The dose represents the mass (mg) of the extract of the mixture treated per kg of body weight of the animal model mouse

TABLE 41

Decrease of latency to fall by mixture extract of *Moutan* Root Bark, *Angelica Dahurica* Root and *Bupleurum* Root in MPTP-induced Parkinson's disease mouse model

| Treatment substance | Extract dose (mg/kg*) | Inducer dose (MPTP, mg/kg 5x, ip) | Latency to fall(s) |
|---|---|---|---|
| Normal control | — | — | 211.03 ± 4.69 |
| Negative control | — | 30 | 99.87 ± 32.47 |
| *Moutan* Root Bark + *Angelica Dahurica* Root + *Bupleurum* Root 1:1:1 (w:w:w) mixture extract | 1<br>3<br>10 | 30<br>30<br>30 | 153.34 ± 27.13<br>187.06 ± 24.94<br>181.76 ± 19.81 |

*The dose represents the mass (mg) of the extract of the mixture treated per kg of body weight of the animal model mouse <9-3> Protective Effect of Mixture Extract of Moutan Root Bark, Angelica Dahurica Root and Bupleurum Root on Dopaminergic Neurons In Vivo To investigate the in vivo therapeutic effect of the extract of the mixture of Moutan Root Bark, Angelica Dahurica Root and Bupleurum Root of the present invention on Parkinson's disease, the brain tissue of the MPTP-induced Parkinson's disease mouse model treated with the extract of the mixture of the invention was obtained, with which the protective effect on dopaminergic neurons in striatum (ST) and substantia nigra (SN) was confirmed.

Particularly, the mouse model finished with the behavioral test in Experimental Example <8-2> was administered with zoletil (50 mg/kg) via intramuscular injection for anesthesia. PBS containing 4% paraformaldehyde was perfused through the heart and then the brain was extracted. The extracted brain was fixed in 4% paraformaldehyde once again, and then dipped in 30% sucrose solution at 4° C. until the brain was sunken down, which was then frozen. The frozen brain tissue was cut into 30 μm coronal sections by using cryostat microtome (Product name: CM3000, Leica, Germany), and the sections were stored in a stock solution comprising glycerin, ethyleneglycol, and PBS at 4° C. The sections were placed on a cover slip and washed with PBS, followed by treatment with PBS containing 1% $H_2O_2$ for 15 minutes to eliminate peroxidase activity from the tissue. Then, anti-tyrosine hydroxylase antibody (anti-TH; 1:2000, rabbit originated; Millipore, USA) was treated thereto as the primary antibody, followed by reaction for overnight. Biotinylated anti-rabbit IgG antibody was treated thereto as the secondary antibody, followed by reaction at room temperature for 90 minutes. Upon completion of the reaction, the tissue was treated with avidin-biotin complex solution included in Vectastain ABC kit (Vector Laboratories, USA), followed by reaction for 1 hour. Color development was induced by using diaminobenzidine. To investigate the dopamine cell protective effect, optical density of striatum (ST) was measured and then tyrosine hydroxylase (TH) positive cells in substantia nigra (SN) were counted. The normal control group was treated with a solvent and the negative control was intraperitoneally administered (i.p.) with MPTP at the dose of 30 mg/kg for 5 days, but not treated with the extract of the mixture thereafter.

As a result, as shown in Table 42, optical density of the stained TH in striatum (ST) of the Parkinson's disease animal model administered with the mixed ethanol extract of Moutan Root Bark, Angelica Dahurica Root and Bupleurum Root was increased dose-dependently, suggesting that the extract had the protective effect on dopaminergic neurons. As shown in Table 43, TH positive cells in substantia nigra (SN) were also increased according to the administration of the mixed ethanol extract of Moutan Root Bark, Angelica Dahurica Root and Bupleurum Root, dose-dependently (Tables 42 and 43).

TABLE 42

Increase of TH optical density in striatum (ST) by mixture extract of *Moutan* Root Bark, *Angelica Dahurica* Root and *Bupleurum* Root in MPTP-induced Parkinson's disease mouse model

| Treatment substance | Treatment Extract dose (mg/kg*) | Inducer dose (MPTP, mg/kg 5x, ip) | Optical density (% of control) |
|---|---|---|---|
| Normal control | — | — | 100.00 ± 4.33 |
| Negative control | — | 30 | 43.48 ± 4.02 |
| *Moutan* Root Bark + *Angelica Dahurica* Root + *Bupleurum* Root 1:1:1 (w:w:w) mixture extract | 1 | 30 | 52.70 ± 2.39 |
| | 3 | 30 | 66.45 ± 5.23 |
| | 10 | 30 | 72.00 ± 4.21 |

*The dose represents the mass (mg) of the extract of the mixture treated per kg of body weight of the animal model mouse

TABLE 43

Increase of TH-positive cells in substantia nigra (SN) by mixture extract of *Moutan* Root Bark, *Angelica Dahurica* Root and *Bupleurum* Root in MPTP-induced Parkinson's disease mouse model

| Treatment substance | Treatment Extract dose (mg/kg*) | Inducer dose (MPTP, mg/kg 5x, ip) | TH-positive cell (% of control) |
|---|---|---|---|
| Normal control | — | — | 100.00 ± 2.99 |
| Negative control | — | 30 | 52.83 ± 6.42 |
| *Moutan* Root Bark + *Angelica Dahurica* Root + *Bupleurum* Root 1:1:1 (w:w:w) mixture extract | 1 | 30 | 62.27 ± 2.78 |
| | 3 | 30 | 73.20 ± 3.93 |
| | 10 | 30 | 85.14 ± 4.69 |

*The dose represents the mass (mg) of the extract of the mixture treated per kg of body weight of the animal model mouse <9-4> Effect of Mixture Extract of Moutan Root Bark, Angelica Dahurica Root and Bupleurum Root on In Vivo Dopamine Amount To investigate the in vivo therapeutic effect of the extract of the mixture of Moutan Root Bark, Angelica Dahurica Root and Bupleurum Root of the present invention on Parkinson's disease, the brain tissue of the MPTP-induced Parkinson's disease mouse model treated with the extract of the mixture of the invention was obtained and the level of dopamine therein was measured.

Particularly, the brain was extracted from the mouse finished with the behavioral test in Experimental Example <8-2>. ST was separated from the extracted brain, followed by homogenization. Perchloric acid (Sigma) was added thereto, followed by culture. The cultured ST was filtered and pressurized/concentrated. The concentrated extract proceeded to chromatography to measure the level of dopamine. The normal control group was treated with a solvent and the negative control was intraperitoneally administered (i.p.) with MPTP at the dose of 30 mg/kg for 5 days, but not treated with the extract of the mixture thereafter.

As a result, as shown in table 44, the level of dopamine was significantly reduced in the Parkinson's disease animal model not treated with the mixed ethanol extract of Moutan Root Bark, Angelica Dahurica Root and Bupleurum Root, but the level of dopamine was significantly increased when the mixed ethanol extract of Moutan Root Bark, Angelica Dahurica Root and Bupleurum Root was administered to the animal (Table 44).

TABLE 44

Effect of mixture extract of *Moutan* Root Bark, *Angelica Dahurica* Root and *Bupleurum* Root on dopamine amount in MPTP-induced Parkinson's disease mouse model

| Treatment substance | Treatment Extract dose (mg/kg*) | Inducer dose (MPTP, mg/kg 5x, ip) | Dopamine content (% of control) |
|---|---|---|---|
| Normal control | — | — | 100.02 ± 7.69 |
| Negative control | — | 30 | 34.16 ± 4.77 |
| *Moutan* Root Bark + *Angelica Dahurica* Root + *Bupleurum* Root 1:1:1 (w:w:w) mixture extract | 1 | 30 | 49.87 ± 3.86 |
| | 3 | 30 | 53.77 ± 2.09 |
| | 10 | 30 | 57.02 ± 2.76 |

*The dose represents the mass (mg) of the extract of the mixture treated per kg of body weight of the animal model mouse <9-5> Recovery Effect of Mixture Extract of Moutan Root Bark, Angelica Dahurica Root and Bupleurum Root on Damage of TH, Mitochondria, and Insulin Signaling System In Vivo To investigate the in vivo therapeutic effect of the extract of the mixture of Moutan Root Bark, Angelica Dahurica Root and Bupleurum Root of the present invention on Parkinson's disease, the brain tissue of the MPTP-induced Parkinson's disease mouse model treated with the extract of the mixture of the invention was obtained and the expression levels of TH and ND9, the mitochondria marker, and the phosphorylation level of Akt1, the insulin signaling system marker, were measured.

Particularly, substantia nigra (SN), corpus striatum (ST), and cerebellum sections were obtained by the same manner as described in Experimental Example <8-3>, from which brain tissue protein was obtained. Western blotting was performed with the protein to measure the expression levels of TH and ND9 and the phosphorylation level of Akt1 (S473 and T308). At this time, β-actin was used as the control protein for the comparison of the expression. The normal control group was treated with a solvent and the negative control was intraperitoneally administered (i.p.) with MPTP at the dose of 30 mg/kg for 5 days, but not treated with the extract of the mixture thereafter.

As a result, as shown in Tables 45~47, the expression levels of TH and ND9 in SN, ST, and cerebellium of the animal model administered with the mixed 90% ethanol extract of Moutan Root Bark, Angelica Dahurica Root and Bupleurum Root at the dose of 10 mg/kg were recovered almost to the normal level as high as that of the normal control, and the phosphorylation level of Akt1 protein was also recovered to the normal level (Tables 45~47).

TABLE 45

Recovery effect of mixture extract of *Moutan* Root Bark, *Angelica Dahurica* Root and *Bupleurum* Root on damage of TH, mitochondria, and insulin signaling system in SN of MPTP-induced Parkinson's disease mouse model

| Treatment substance | Extract dose (mg/kg) | Inducer dose (MPTP, mg/kg 5x, ip) | pAkt(T308)/β-actin |
|---|---|---|---|
| Normal control | — | — | 100.00 ± 1.31 |
| Negative control | — | 30 | 5.65 ± 0.97 |
| *Moutan* Root Bark + *Angelica Dahurica* Root + *Bupleurum* Root 1:1:1 (w:w:w) mixture extract | 1<br>3<br>10 | 30<br>30<br>30 | 67.43 ± 4.62<br>71.07 ± 3.99<br>79.03 ± 3.12 |

| Treatment substance | Extract dose (mg/kg) | Inducer dose (MPTP, mg/kg 5x, ip) | pAkt(S473)/β-actin |
|---|---|---|---|
| Normal control | — | — | 100.00 ± 1.82 |
| Negative control | — | 30 | 2.90 ± 0.37 |
| *Moutan* Root Bark + *Angelica Dahurica* Root + *Bupleurum* Root 1:1:1 (w:w:w) mixture extract | 1<br>3<br>10 | 30<br>30<br>30 | 72.74 ± 6.81<br>83.62 ± 2.95<br>87.78 ± 4.12 |

| Treatment substance | Extract dose (mg/kg) | Inducer dose (MPTP, mg/kg 5x, ip) | Akt/β-actin |
|---|---|---|---|
| Normal control | — | — | 100.00 ± 2.95 |
| Negative control | — | 30 | 101.94 ± 1.17 |
| *Moutan* Root Bark + *Angelica Dahurica* Root + *Bupleurum* Root 1:1:1 (w:w:w) mixture extract | 1<br>3<br>10 | 30<br>30<br>30 | 103.71 ± 3.95<br>97.34 ± 2.60<br>97.82 ± 3.78 |

| Treatment substance | Extract dose (mg/kg) | Inducer dose (MPTP, mg/kg 5x, ip) | TH/β-actin |
|---|---|---|---|
| Normal control | — | — | 100.00 ± 1.25 |
| Negative control | — | 30 | 3.79 ± 0.06 |
| *Moutan* Root Bark + *Angelica Dahurica* Root + *Bupleurum* Root 1:1:1 (w:w:w) mixture extract | 1<br>3<br>10 | 30<br>30<br>30 | 76.62 ± 5.65<br>88.76 ± 5.57<br>80.27 ± 4.96 |

TABLE 45-continued

Recovery effect of mixture extract of *Moutan* Root Bark, *Angelica Dahurica* Root and *Bupleurum* Root on damage of TH, mitochondria, and insulin signaling system in SN of MPTP-induced Parkinson's disease mouse model

| Treatment substance | Extract dose (mg/kg) | Inducer dose (MPTP, mg/kg 5x, ip) | ND9/β-actin |
|---|---|---|---|
| Normal control | — | — | 100.00 ± 2.81 |
| Negative control | — | 30 | 6.17 ± 0.57 |
| *Moutan* Root Bark + *Angelica Dahurica* Root + *Bupleurum* Root 1:1:1 (w:w:w) mixture extract | 1<br>3<br>10 | 30<br>30<br>30 | 83.42 ± 2.53<br>86.03 ± 2.78<br>87.71 ± 3.76 |

TABLE 46

Recovery effect of mixture extract of *Moutan* Root Bark, *Angelica Dahurica* Root and *Bupleurum* Root on damage of TH, mitochondria, and insulin signaling system in ST of MPTP-induced Parkinson's disease mouse model

| Treatment substance | Extract dose (mg/kg) | Inducer dose (MPTP, mg/kg 5x, ip) | pAkt(T308)/β-actin |
|---|---|---|---|
| Normal control | — | — | 100.00 ± 3.73 |
| Negative control | — | 30 | 8.82 ± 0.41 |
| *Moutan* Root Bark + *Angelica Dahurica* Root + *Bupleurum* Root 1:1:1 (w:w:w) mixture extract | 1<br>3<br>10 | 30<br>30<br>30 | 76.83 ± 3.96<br>88.86 ± 4.94<br>82.53 ± 7.71 |

| Treatment substance | Extract dose (mg/kg) | Inducer dose (MPTP, mg/kg 5x, ip) | pAkt(S473)/β-actin |
|---|---|---|---|
| Normal control | — | — | 100.00 ± 3.97 |
| Negative control | — | 30 | 6.05 ± 1.03 |
| *Moutan* Root Bark + *Angelica Dahurica* Root + *Bupleurum* Root 1:1:1 (w:w:w) mixture extract | 1<br>3<br>10 | 30<br>30<br>30 | 72.53 ± 5.71<br>86.77 ± 2.65<br>96.18 ± 6.11 |

| Treatment substance | Extract dose (mg/kg) | Inducer dose (MPTP, mg/kg 5x, ip) | Akt/β-actin |
|---|---|---|---|
| Normal control | — | — | 100.00 ± 2.11 |
| Negative control | — | 30 | 101.34 ± 4.14 |
| *Moutan* Root Bark + *Angelica Dahurica* Root + *Bupleurum* Root 1:1:1 (w:w:w) mixture extract | 1<br>3<br>10 | 30<br>30<br>30 | 96.35 ± 6.44<br>104.85 ± 2.24<br>103.51 ± 3.91 |

TABLE 46-continued

Recovery effect of mixture extract of *Moutan* Root Bark, *Angelica Dahurica* Root and *Bupleurum* Root on damage of TH, mitochondria, and insulin signaling system in ST of MPTP-induced Parkinson's disease mouse model

| Treatment substance | Extract dose (mg/kg) | Inducer dose (MPTP, mg/kg 5x, ip) | TH/β-actin |
|---|---|---|---|
| Normal control | — | — | 100.00 ± 2.61 |
| Negative control | — | 30 | 5.41 ± 1.72 |
| *Moutan* Root Bark + *Angelica Dahurica* Root + *Bupleurum* Root 1:1:1 (w:w:w) mixture extract | 1<br>3<br>10 | 30<br>30<br>30 | 87.02 ± 5.97<br>93.53 ± 2.59<br>92.79 ± 5.41 |

| Treatment substance | Extract dose (mg/kg) | Inducer dose (MPTP, mg/kg 5x, ip) | ND9/β-actin |
|---|---|---|---|
| Normal control | — | — | 100.00 ± 4.88 |
| Negative control | — | 30 | 5.03 ± 0.74 |
| *Moutan* Root Bark + *Angelica Dahurica* Root + *Bupleurum* Root 1:1:1 (w:w:w) mixture extract | 1<br>3<br>10 | 30<br>30<br>30 | 79.33 ± 1.18<br>86.85 ± 2.63<br>92.31 ± 3.68 |

TABLE 47

Recovery effect of mixture extract of *Moutan* Root Bark, *Angelica Dahurica* Root and *Bupleurum* Root on damage of TH, mitochondria, and insulin signaling system in cerebellum of MPTP-induced Parkinson's disease mouse model

| Treatment substance | Extract dose (mg/kg) | Inducer dose (MPTP, mg/kg 5x, ip) | pAkt(T308)/β-actin |
|---|---|---|---|
| Normal control | — | — | 100.00 ± 3.73 |
| Negative control | — | 30 | 8.82 ± 0.41 |
| *Moutan* Root Bark + *Angelica Dahurica* Root + *Bupleurum* Root 1:1:1 (w:w:w) mixture extract | 1<br>3<br>10 | 30<br>30<br>30 | 76.83 ± 3.96<br>88.86 ± 4.94<br>82.53 ± 7.71 |

| Treatment substance | Extract dose (mg/kg) | Inducer dose (MPTP, mg/kg 5x, ip) | pAkt(S473)/β-actin |
|---|---|---|---|
| Normal control | — | — | 100.00 ± 3.97 |
| Negative control | — | 30 | 6.05 ± 1.03 |
| *Moutan* Root Bark + *Angelica Dahurica* Root + *Bupleurum* Root 1:1:1 (w:w:w) mixture extract | 1<br>3<br>10 | 30<br>30<br>30 | 72.53 ± 5.71<br>86.77 ± 2.65<br>96.18 ± 6.11 |

TABLE 47-continued

Recovery effect of mixture extract of *Moutan* Root Bark, *Angelica Dahurica* Root and *Bupleurum* Root on damage of TH, mitochondria, and insulin signaling system in cerebellum of MPTP-induced Parkinson's disease mouse model

| Treatment substance | Extract dose (mg/kg) | Inducer dose (MPTP, mg/kg 5x, ip) | Akt/β-actin |
|---|---|---|---|
| Normal control | — | — | 100.00 ± 2.11 |
| Negative control | — | 30 | 101.34 ± 4.14 |
| *Moutan* Root Bark + *Angelica Dahurica* Root + *Bupleurum* Root 1:1:1 (w:w:w) mixture extract | 1<br>3<br>10 | 30<br>30<br>30 | 96.35 ± 6.44<br>104.85 ± 2.24<br>103.51 ± 3.91 |

| Treatment substance | Extract dose (mg/kg) | Inducer dose (MPTP, mg/kg 5x, ip) | TH/β-actin |
|---|---|---|---|
| Normal control | — | — | 100.00 ± 2.61 |
| Negative control | — | 30 | 5.41 ± 1.72 |
| *Moutan* Root Bark + *Angelica Dahurica* Root + *Bupleurum* Root 1:1:1 (w:w:w) mixture extract | 1<br>3<br>10 | 30<br>30<br>30 | 87.02 ± 5.97<br>93.53 ± 2.59<br>92.79 ± 5.41 |

| Treatment substance | Extract dose (mg/kg) | Inducer dose (MPTP, mg/kg 5x, ip) | ND9/β-actin |
|---|---|---|---|
| Normal control | — | — | 100.00 ± 4.88 |
| Negative control | — | 30 | 5.03 ± 0.74 |
| *Moutan* Root Bark + *Angelica Dahurica* Root + *Bupleurum* Root 1:1:1 (w:w:w) mixture extract | 1<br>3<br>10 | 30<br>30<br>30 | 79.33 ± 1.18<br>86.85 ± 2.63<br>92.31 ± 3.68 |

Figure 2:
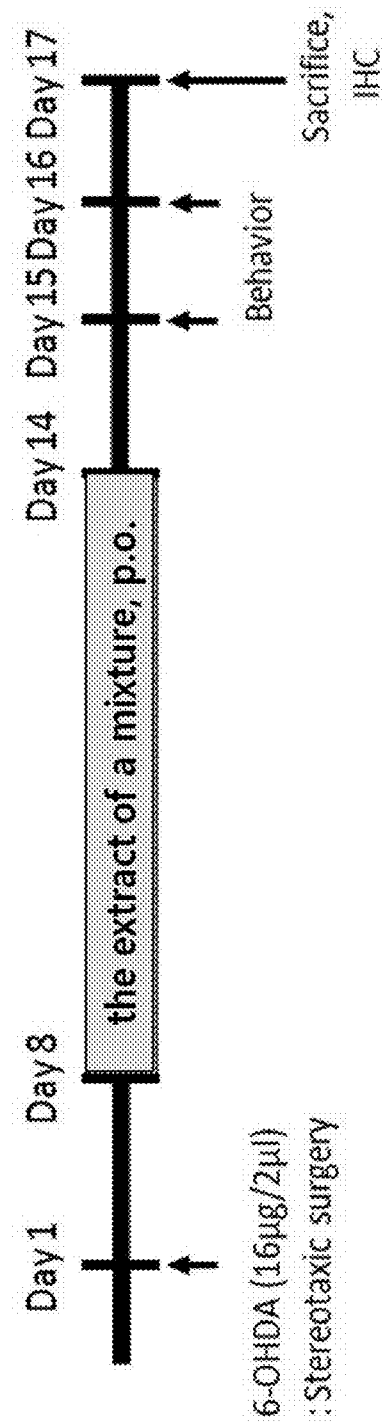
FIG. 2 is a schematic diagram illustrating the process of the construction of Parkinson's disease animal model through the 6-OHDA (6-hydroxydopamine) administration. Particularly, 16 μg of 6-OHDA (6-hydroxydopamine) was diluted in 2 μl of 0.1% ascorbic acid, which was injected through stereotaxic surgery to the test animal once, resulting in the construction of Parkinson's disease animal model. One week after the surgery, the freeze-dried 90% ethanol extract of a mixture composed of Moutan Root Bark, Angelica Dahurica Root and Bupleurum Root at the ratio of 1:1:1 was dissolved in water, which was administered (per oral, p.o.) to the mouse at the dose of 3 mg/kg once a day for 7 days. The prepared mouse model was used for behavioral test. The animal was sacrificed and cell analysis and western blotting were performed.

Experimental Example 10: Therapeutic Effect of Mixture Extract of Moutan Root Bark, Angelica Dahurica Root and Bupleurum Root on Parkinson's Disease In Vivo <10-1> Construction of Parkinson's Disease Animal Model: 6-OHDA(6-hydroxydopamine)-induced Parkinson's Disease Mouse Model To investigate the in vivo therapeutic effect of the extract of the mixture of Moutan Root Bark, Angelica Dahurica Root and Bupleurum Root of the present invention on Parkinson's disease, Parkinson's disease animal model was constructed as shown in FIG. 2 (FIG. 2).

Particularly, 8 week old ICR male mice (weight: approximately 19~22 g) were distributed, followed by adaptation in an animal laboratory of Kyung Hee University College of Pharmacy for at least 1 week. At this time, the indoor temperature was regulated at 22±2° C. and the humidity was controlled at 53±3%. The light and dark cycle was set at 12 hr/12 hr. Water and feeds were provided freely. After the adaptation, mice were grouped into 3 groups and each group was allocated with 6 mice. 16 µg of 6-OHDA (6-hydroxydopamine) was diluted in 2 µl of 0.1% ascorbic acid, which was injected in each mouse via stereotaxic surgery, resulting in the construction of Parkinson's disease animal model. The lyophilisate of the mixed 90% ethanol extract of Moutan Root Bark, Angelica Dahurica Root and Bupleurum Root (1:1:1) prepared in Example <5-1> was dissolved in water, which was orally administered (per oral, p.o.) to the mice at the dose of 3 mg/kg once a day for 7 days. The normal control group was treated with a solvent and the negative control was injected with 0.1% ascorbic acid containing 6-OHDA via stereotaxic surgery.

<10-2> Improvement of Motor Coordination by Mixture Extract of Moutan Root Bark, Angelica Dahurica Root and Bupleurum Root in 6-OHDA-Induced Parkinson's Disease Mouse Model To investigate the in vivo therapeutic effect of the extract of the mixture of Moutan Root Bark, Angelica Dahurica Root and Bupleurum Root of the present invention on Parkinson's disease, behavioral test (Pole test, Rotarod test) was performed with the 6-OHDA-induced Parkinson's disease mouse model after the administration of the extract of the mixture above.

Particularly, Parkinson's disease mouse model was constructed in Experimental Example <9-1>. The animal model, 7 days after the construction, was placed on top of the pole having the rough surface (diameter: 8 mm, height: 55 cm). Time for the mouse to move down completely was measured every 30 seconds, which was defined as time to turn (T-turn), and time for the mouse to arrive on the floor was measured, which was defined as locomotion activity time (T-LA). The animal was placed on the wheel whose rpm could be regulated. Time for the animal to fall down was measured (latency to fall). The normal control group was treated with a solvent and the negative control was injected with 0.1% ascorbic acid containing 6-OHDA via stereotaxic surgery. Then, Pole test was performed with the controls to measure the T-turn and T-LA and rotarod test was performed to measure the latency to fall by the same manner as described above.

As a result, as shown in Table 48 and Table 49, compared with the normal control group treated with a solvent, T-turn and T-LA were significantly increased in the negative control group treated with 6-OHDA alone. In the meantime, in the Parkinson's disease mouse model treated with the mixed 90% ethanol extract of Moutan Root Bark, Angelica Dahurica Root and Bupleurum Root, T-turn and T-LA were reduced (Table 48 and Table 49). As shown in Table 50, it was confirmed from the Rotarod test that latency to fall was significantly reduced in the negative control treated with 6-OHDA alone, while latency to fall was increased in the Parkinson's disease mouse model treated with the mixed 90% ethanol extract of Moutan Root Bark, Angelica Dahurica Root and Bupleurum Root. Therefore, it was confirmed that the motor coordination was recovered in the Parkinson's disease mouse model by the treatment of the mixed 90% ethanol extract of Moutan Root Bark, Angelica Dahurica Root and Bupleurum Root (Tables 48~50).

TABLE 48

Decrease of T-turn by mixture extract of *Moutan* Root Bark, *Angelica Dahurica* Root and *Bupleurum* Root in 6-OHDA-induced Parkinson's disease mouse model

| Treatment substance | Extract dose (mg/kg) | Inducer dose (6-OHDA, µg) | T-turn(s) |
|---|---|---|---|
| Normal control | — | — | 3.75 ± 0.76 |
| Negative control | — | 16 | 15.64 ± 4.01 |
| *Moutan* Root Bark + *Angelica Dahurica* Root + *Bupleurum* Root 1:1:1 (w:w:w) mixture extract | 3 | 16 | 4.71 ± 1.65 |

TABLE 49

Decrease of T-LA by mixture extract of *Moutan* Root Bark, *Angelica Dahurica* Root and *Bupleurum* Root in 6-OHDA-induced Parkinson's disease mouse model

| Treatment substance | Extract dose (mg/kg) | Inducer dose (6-OHDA, µg) | T-LA(s) |
|---|---|---|---|
| Normal control | — | — | 9.54 ± 1.67 |
| Negative control | — | 16 | 17.24 ± 7.01 |
| *Moutan* Root Bark + *Angelica Dahurica* Root + *Bupleurum* Root 1:1:1 (w:w:w) mixture extract | 3 | 16 | 7.87 ± 3.08 |

TABLE 50

Decrease of latency to fall by mixture extract of *Moutan* Root Bark, *Angelica Dahurica* Root and *Bupleurum* Root in 6-OHDA-induced Parkinson's disease mouse model

| Treatment substance | Extract dose (mg/kg) | Inducer dose (6-OHDA, µg) | Latency to fall(s) |
|---|---|---|---|
| Normal control | — | — | 46.08 ± 19.24 |
| Negative control | — | 16 | 3.11 ± 0.38 |
| *Moutan* Root Bark + *Angelica Dahurica* Root + *Bupleurum* Root 1:1:1 (w:w:w) mixture extract | 3 | 16 | 17.20 ± 3.19 |

<10-3> Protective Effect of Mixture Extract of Moutan Root Bark, Angelica Dahurica Root and Bupleurum Root on Dopaminergic Neurons In Vivo To investigate the in vivo therapeutic effect of the extract of the mixture of Moutan Root Bark, Angelica Dahurica Root and Bupleurum Root of the present invention on Parkinson's disease, the brain tissue of the 6-OHDA-induced Parkinson's disease mouse model treated with the extract of the mixture of the invention was obtained, with which the protective effect on dopaminergic neurons in striatum (ST) and substantia nigra (SN) was confirmed.

Particularly, the mouse model finished with the behavioral test in Experimental Example <9-2> was administered with zoletil (50 mg/kg) via intramuscular injection for anesthesia.

PBS containing 4% paraformaldehyde was perfused through the heart and then the brain was extracted. The extracted brain was fixed in 4% paraformaldehyde once again, and then dipped in 30% sucrose solution at 4° C. until the brain was sunken down, which was then frozen. The frozen brain tissue was cut into 30 μm coronal sections by using cryostat microtome (Product name: CM3000, Leica, Germany), and the sections were stored in a stock solution comprising glycerin, ethyleneglycol, and PBS at 4° C. The sections were placed on a cover slip and washed with PBS, followed by treatment with PBS containing 1% $H_2O_2$ for 15 minutes to eliminate peroxidase activity from the tissue. Then, anti-tyrosine hydroxylase antibody (anti-TH; 1:2000, rabbit originated; Millipore, USA) was treated thereto as the primary antibody, followed by reaction for overnight. Biotinylated anti-rabbit IgG antibody was treated thereto as the secondary antibody, followed by reaction at room temperature for 90 minutes. Upon completion of the reaction, the tissue was treated with avidin-biotin complex solution included in Vectastain ABC kit (Vector Laboratories, USA), followed by reaction for 1 hour. Color development was induced by using diaminobenzidine. To investigate the dopamine cell protective effect, optical density of striatum (ST) was measured and then tyrosine hydroxylase (TH) positive cells in substantia nigra (SN) were counted. The normal control group was treated with a solvent and the negative control was injected with 0.1% ascorbic acid containing 6-OHDA via stereotaxic surgery.

As a result, as shown in Table 51 and Table 52, optical density of the stained TH in striatum (ST) of the Parkinson's disease animal model administered with the mixed ethanol extract of Moutan Root Bark, Angelica Dahurica Root and Bupleurum Root was increased dose-dependently, suggesting that the extract had the protective effect on dopaminergic neurons. TH positive cells in substantia nigra (SN) were also increased according to the administration of the mixed ethanol extract of Moutan Root Bark, Angelica Dahurica Root and Bupleurum Root, dose-dependently (Tables 51 and 52).

TABLE 51

Increase of TH optical density in striatum (ST) by mixture extract of Moutan Root Bark, *Angelica Dahurica* Root and *Bupleurum* Root in 6-OHDA-induced Parkinson's disease mouse model

| Treatment substance | Extract dose (mg/kg) | Inducer dose (6-OHDA, μg) | Optical density (% of control) |
|---|---|---|---|
| Normal control | — | — | 100.01 ± 6.58 |
| Negative control | — | 16 | 58.46 ± 4.09 |
| Moutan Root Bark + *Angelica Dahurica* Root + *Bupleurum* Root 1:1:1 (w:w:w) mixture extract | 3 | 16 | 76.84 ± 5.37 |

TABLE 52

Increase of TH-positive cells in substantia nigra (SN) by mixture extract of Moutan Root Bark, *Angelica Dahurica* Root and *Bupleurum* Root in 6-OHDA-induced Parkinson's disease mouse model

| Treatment substance | Extract dose (mg/kg) | Inducer dose (6-OHDA, μg) | TH-positive Cell (% of control) |
|---|---|---|---|
| Normal control | — | — | 100.00 ± 7.94 |
| Negative control | — | 16 | 63.67 ± 3.08 |
| Moutan Root Bark + *Angelica Dahurica* Root + *Bupleurum* Root 1:1:1 (w:w:w) mixture extract | 3 | 16 | 76.90 ± 2.18 |

Figure 3:
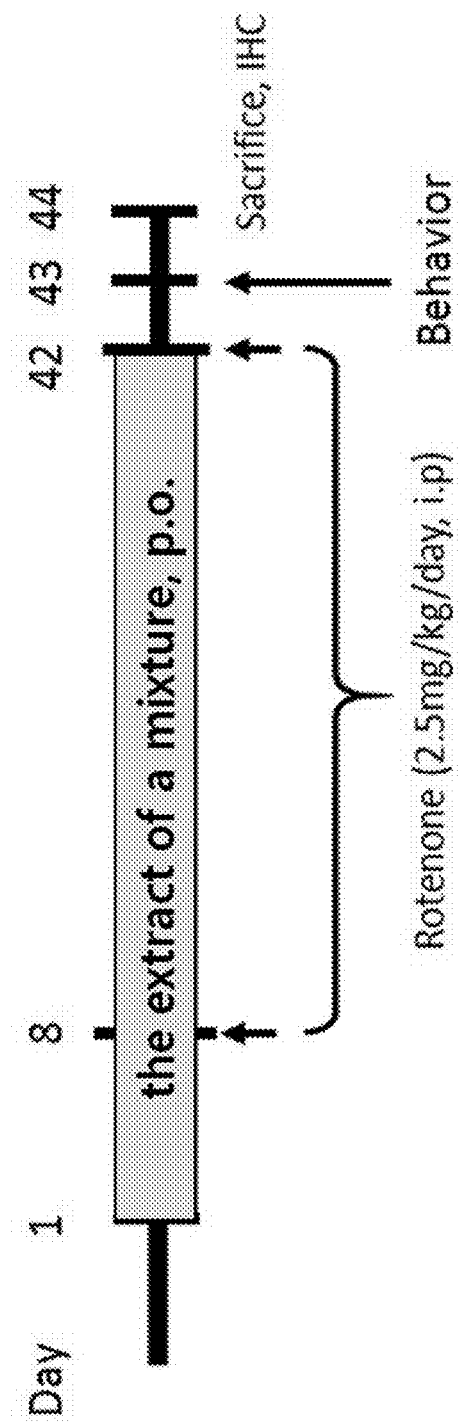
FIG. 3 is a schematic diagram illustrating the process of the construction of Parkinson's disease animal model through the rotenone administration. Particularly, the freeze-dried 90% ethanol extract of a mixture composed of Moutan Root Bark, Angelica Dahurica Root and Bupleurum Root at the ratio of 1:1:1 was dissolved in water, which was administered (per oral, p.o.) to the rat at the dose of 10 mg/kg once a day for 6 weeks. One week after the oral administration, rotenone was injected (intraperitoneal, i.p.) to the rat at the dose of 2.5 mg/kg once a day for 5 weeks, resulting in the construction of Parkinson's disease animal model. The prepared rate model was used for behavioral test. The animal was sacrificed and cell analysis and western blotting were performed.

Experimental Example 11: Therapeutic Effect of Mixture Extract of Moutan Root Bark, Angelica Dahurica Root and Bupleurum Root on Parkinson's Disease In Vivo <11-1> Construction of Parkinson's Disease Animal Model: Rotenone-Induced Parkinson's Disease Rat Model To investigate the in vivo therapeutic effect of the extract of the mixture of Moutan Root Bark, Angelica Dahurica Root and Bupleurum Root of the present invention on Parkinson's disease, Parkinson's disease animal model was constructed as shown in FIG. 3 (FIG. 3).

Particularly, 7 week old SD male rats (weight: 200~220 g) were distributed, followed by adaptation in an animal laboratory of Dong-A ST Research Division for at least 1 week. At this time, the indoor temperature was regulated at 22±2° C. and the humidity was controlled at 53±3%. The light and dark cycle was set at 12 hr/12 hr. Water and feeds were provided freely. After the adaptation, rats were grouped into 3 groups and each group was allocated with 6 rats. The lyophilisate of the mixed 90% ethanol extract of Moutan Root Bark, Angelica Dahurica Root and Bupleurum Root (1:1:1) prepared in Example <5-1> was dissolved in water, which was orally administered (per oral, p.o.) to the rats at the dose of 10 mg/kg once a day for 6 weeks. Then, the rats were administered (intraperitoneal, i.p.) with rotenone at the dose of 2.5 mg/kg 1 week after the oral administration once a day for 5 weeks, resulting in the construction of Parkinson's disease animal model. The normal control group was treated with a solvent and the negative control was administered (intraperitoneal, i.p.) with rotenone at the dose of 2.5 mg/kg once a day for 5 weeks.

<11-2> Improvement of Motor Coordination in Rotenone-Induced Parkinson's Disease Rat Model by Mixture Extract of Moutan Root Bark, Angelica Dahurica Root and Bupleurum Root To investigate the in vivo therapeutic effect of the extract of the mixture of Moutan Root Bark, Angelica Dahurica Root and Bupleurum Root of the present invention on Parkinson's disease, behavioral test (Cylinder test) was performed with the rotenone-induced Parkinson's disease rat model after the administration of the extract of the mixture above.

Particularly, cylinder test was performed with the Parkinson's disease rat model constructed in Experimental Example <11-1>. The rats were placed in a cylinder (height: 30 cm, diameter: 20 cm). It was counted how many times the rat raised the body and placed the paws against the wall for 5 minutes. The normal control group was treated with a solvent and the negative control was intraperitoneally administered with rotenone at the dose of 2.5 mg/kg once a day for 5 weeks. Likewise, it was counted with the controls how many times the rat raised the body and placed the paws against the wall for 5 minutes.

As a result, as shown in Table 53, the number of standing of the negative control group administered with rotenone alone was significantly reduced, compared with that of the normal control group treated with a solvent alone, which was increased when the mixed 90% ethanol extract of Moutan Root Bark, Angelica Dahurica Root and Bupleurum Root was administered (Table 53).

TABLE 53

Effect of mixture extract of Moutan Root Bark, *Angelica Dahurica* Root and *Bupleurum* Root on number of times the paws are placed against the wall for 5 minutes in rotenone-induced Parkinson's disease rat model

| Treatment | | Inducer dose | |
|---|---|---|---|
| Treatment substance | Extract dose (mg/kg) | (Rotenone, mg/kg) | No. of rears per 5 min |
| Normal control | — | — | 13.75 ± 2.14 |
| Negative control | — | 2.5 | 2.19 ± 0.49 |
| Moutan Root Bark + *Angelica Dahurica* Root + *Bupleurum* Root 1:1:1 (w:w:w) mixture extract | 10 | 2.5 | 6.05 ± 1.85 |

<11-3> Decrease of α-synuclein Accumulation by Micture Extract of Moutan Root Bark, Angelica Dahurica Root and Bupleurum Root To investigate the in vivo therapeutic effect of the extract of the mixture of Moutan Root Bark, Angelica Dahurica Root and Bupleurum Root of the present invention on Parkinson's disease, the brain tissues were obtained from the rotenone-induced Parkinson's disease rat model treated with the mixture extract. The pattern of α-synuclein-oligomer accumulation in substantia nigra (SN) of the brain tissue was investigated.

Particularly, the rat model finished with the behavioral test in Experimental Example <11-2> was administered with zoletil (50 mg/kg) via intramuscular injection for anesthesia. PBS containing 4% paraformaldehyde was perfused through the heart and then the brain was extracted. The extracted brain was fixed in 4% paraformaldehyde once again, and then dipped in 30% sucrose solution at 4° C. until the brain was sunken down, which was then frozen. The frozen brain tissue was cut into 30 μm coronal sections by using cryostat microtome (Product name: CM3000, Leica, Germany), and the sections were stored in glycerin, ethyleneglycol, and PBS at 4° C. The sections were placed on a cover slip and washed with PBS, followed by treatment with PBS containing 1% $H_2O_2$ for 15 minutes to eliminate peroxidase activity from the tissue. Then, anti-α-synuclein antibody (1:2000; mouse originated, abcam, England) was treated thereto as the primary antibody, followed by reaction for overnight. Biotinylated anti-mouse IgG antibody was treated thereto as the secondary antibody, followed by reaction at room temperature for 90 minutes. Upon completion of the reaction, the tissue was treated with avidin-biotin complex solution included in Vectastain ABC kit (Vector Laboratories, USA), followed by reaction for 1 hour. Color development was induced by using diaminobenzidine. The accumulation of α-synuclein-oligomer was measured by counting the α-synuclein positive cells. The normal control group was treated with a solvent and the negative control was intraperitoneally administered with rotenone at the dose of 2.5 mg/kg once a day for 5 weeks.

As a result, as shown in Table 54, the number of α-synuclein positive cells was reduced in substantia nigra (SN) of the Parkinson's disease animal model administered with the mixed ethanol extract of Moutan Root Bark, Angelica Dahurica Root and Bupleurum Root (Table 54).

TABLE 54

Decrease of α-synuclein positive cells in substantia nigra (SN) of Parkinson's disease animal model by mixture extract of Moutan Root Bark, *Angelica Dahurica* Root and *Bupleurum* Root

| Treatment | | | α-synuclein- |
|---|---|---|---|
| Treatment substance | Extract dose (mg/kg) | Inducer dose (Rotenone, mg/kg) | positive cell(% of control) |
| Normal control | — | — | 100.27 ± 1.86 |
| Negative control | — | 2.5 | 241.76 ± 15.24 |
| Moutan Root Bark + *Angelica Dahurica* Root + *Bupleurum* Root 1:1:1 (w:w:w) mixture extract | 10 | 2.5 | 116.45 ± 9.08 |

Figure 4:
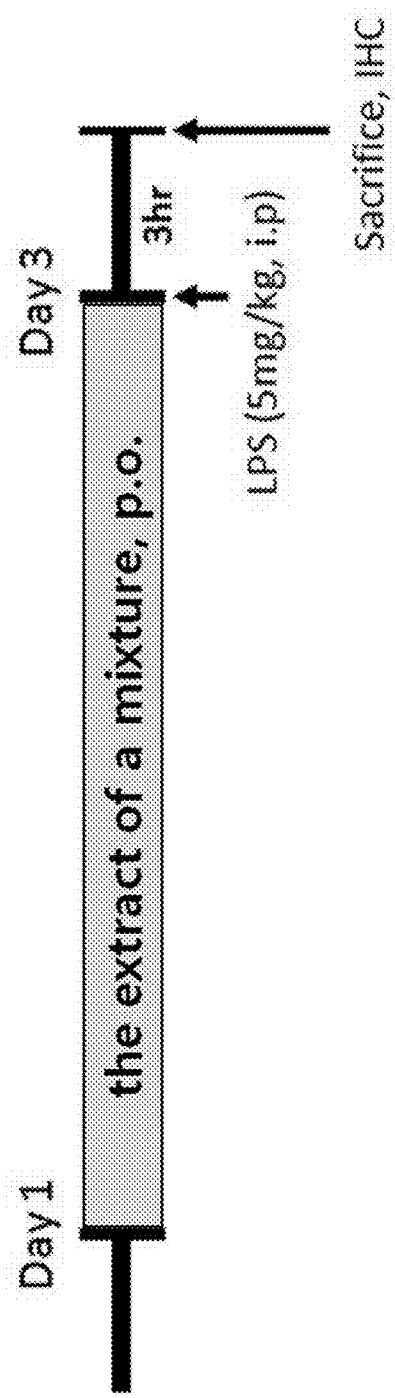
FIG. 4 is a schematic diagram illustrating the process of the construction of Parkinson's disease animal model through the LPS (lipopolysaccharide) administration. Particularly, the freeze-dried 90% ethanol extract of a mixture composed of Moutan Root Bark, Angelica Dahurica Root and Bupleurum Root at the ratio of 1:1:1 was dissolved in water, which was administered (per oral, p.o.) to the mouse at the dose of 10 or 30 mg/kg once a day for 3 days. After the last administration, LPS (lipopolysaccharide) was once administered (intraperitoneal, i.p.) to the mouse at the dose of 5 mg/kg, resulting in the construction of Parkinson's disease animal model. The prepared mouse model was used for anti-brain inflammation efficacy test.

Experimental Example 12: Therapeutic Effect of Mixture Extract of Moutan Root Bark, Angelica Dahurica Root and Bupleurum Root on Parkinson's Disease (Brain Inflammation) In Vivo <12-1> Construction of Neuroinflammation Animal Model: LPS-Induced Parkinson's Disease Mouse Model To investigate the in vivo therapeutic effect of the extract of the mixture of Moutan Root Bark, Angelica Dahurica Root and Bupleurum Root of the present invention on Parkinson's disease, Parkinson's disease animal model was constructed as shown in FIG. 4 (FIG. 4).

Particularly, 8 week old C57BL/6 male mice (weight: approximately 19~22 g) were distributed, followed by adaptation in an animal laboratory of Kyung Hee University College of Pharmacy for at least 1 week. At this time, the indoor temperature was regulated at 22±2° C. and the humidity was controlled at 53±3%. The light and dark cycle was set at 12 hr/12 hr. Water and feeds were provided freely. After the adaptation, mice were grouped into 4 groups and each group was allocated with 6 mice. The lyophilisate of the mixed 90% ethanol extract of Moutan Root Bark, Angelica Dahurica Root and Bupleurum Root (1:1:1) prepared in Example <5-1> was dissolved in water, which was orally administered (per oral, p.o.) to the mice at the dose of 10 or 30 mg/kg once a day for 3 days. Then, the mice were administered (intraperitoneal, i.p.) with LPS (lipopolysaccharide) at the dose of 5 mg/kg after the oral administration, resulting in the construction of Parkinson's disease animal model. The normal control group was treated with a solvent and the negative control was administered with LPS at the dose of 5 mg/kg, but not treated with the extract of the mixture thereafter.

<12-2> Anti-Brain Inflammation Effect of Mixture Extract of Moutan Root Bark, Angelica Dahurica Root and Bupleurum Root To investigate the in vivo therapeutic effect of the extract of the mixture of Moutan Root Bark, Angelica Dahurica Root and Bupleurum Root of the present invention on Parkinson's disease, the brain tissues were obtained from the Parkinson's disease rat model treated with the mixture extract. Anti-brain inflammation effect of the extract of the mixture was confirmed by investigating the activation of astrocytes and microglias in substantia nigra (SN) and hippocampus of the brain tissues obtained above.

Particularly, the neuroinflammation animal model constructed in Experimental Example <12-1> was administered with zoletil (50 mg/kg) via intramuscular injection for anesthesia. PBS containing 4% paraformaldehyde was perfused through the heart and then the brain was extracted. The extracted brain was fixed in 4% paraformaldehyde once again, and then dipped in 30% sucrose solution at 4° C. until the brain was sunken down, which was then frozen. The frozen brain tissue was cut into 30 μm coronal sections by using cryostat microtome (Product name: CM3000, Leica, Germany), and the sections were stored in glycerin, ethyleneglycol, and PBS at 4° C. The sections were placed on a cover slip and washed with PBS, followed by treatment with PBS containing 1% $H_2O_2$ for 15 minutes to eliminate peroxidase activity from the tissue. Then, anti-GFAP antibody (1:5000; rabbit originated, Neuromics, USA) or anti-Iba-1 antibody (1:1000; rabbit originated, Dako, Japan) was treated thereto as the primary antibody, followed by reaction for overnight. Biotinylated anti-rabbit IgG antibody was treated thereto as the secondary antibody, followed by reaction at room temperature for 90 minutes. Upon completion of the reaction, the tissue was treated with avidin-biotin complex solution included in Vectastain ABC kit (Vector Laboratories, USA), followed by reaction for 1 hour. Color development was induced by using diaminobenzidine. The levels of astrocytes and microglias activated in SN and hippocampus were measured by counting the numbers of GFAP and Iba-1 positive cells. The normal control group was treated with a solvent and the negative control was administered with LPS at the dose of 5 mg/kg and not treated with the extract of the mixture of the invention thereafter.

As a result, as shown in Table 55 and Table 56, the GFAP and Iba-1 positive cells increased by LPS in substantia nigra (SN) of the Parkinson's disease mouse model were reduced by the administration of the mixed ethanol extract of Moutan Root Bark, Angelica Dahurica Root and Bupleurum Root dose-dependently. The above result indicated that the activation of astrocyte and microglia was reduced, that is brain inflammation was reduced (Table 55 and Table 56). As shown in Table 57 and Table 58, the GFAP and Iba-1 positive cells increased by LPS in hippocampus of the Parkinson's disease mouse model were reduced by the administration of the mixed ethanol extract of Moutan Root Bark, Angelica Dahurica Root and Bupleurum Root dose-dependently. Likewise, the activation of astrocyte and microglia was reduced, suggesting that brain inflammation was reduced (Table 57 and Table 58).

TABLE 55

Decrease of GFAP-positive cells (astrocytes) in substantia nigra (SN) of LPS-induced Parkinson's disease mouse model by mixture extract of Moutan Root Bark, *Angelica Dahurica* Root and *Bupleurum* Root

| Treatment | | | |
|---|---|---|---|
| Treatment substance | Extract dose (mg/kg) | Inducer dose (LPS, mg/kg) | GFAP-positive cell (% of control) |
| Normal control | — | — | 5.76 ± 0.75 |
| Negative control | — | 5 | 38.15 ± 4.97 |
| Moutan Root Bark + *Angelica Dahurica* Root + *Bupleurum* Root1:1:1(w:w:w) mixture extract | 10 | 5 | 14.28 ± 2.68 |
| | 30 | 5 | 9.41 ± 1.04 |

TABLE 56

Decrease of Iba-1 positive cells in substantia nigra (SN) of LPS-induced Parkinson's disease mouse model by mixture extract of Moutan Root Bark, *Angelica Dahurica* Root and *Bupleurum* Root

| Treatment | | | Iba-1- |
|---|---|---|---|
| Treatment substance | Extract dose (mg/kg) | Inducer dose (LPS, mg/kg) | positive cell (% of control) |
| Normal control | — | — | 8.79 ± 0.75 |
| Negative control | — | 5 | 28.67 ± 0.49 |
| Moutan Root Bark + *Angelica Dahurica* Root + *Bupleurum* Root1:1:1(w:w:w) mixture extract | 10 | 5 | 22.09 ± 2.04 |
| | 30 | 5 | 17.08 ± 1.39 |

TABLE 57

Decrease of GFAP-positive cells in hippocampus of LPS-induced Parkinson's disease mouse model by mixture extract of Moutan Root Bark, *Angelica Dahurica* Root and *Bupleurum* Root

| Treatment | | | |
|---|---|---|---|
| Treatment substance | Extract dose (mg/kg) | Inducer dose (LPS, mg/kg) | GFAP-positive cell (% of control) |
| Normal control | — | — | 20.48 ± 4.98 |
| Negative control | — | 5 | 71.18 ± 3.63 |
| Moutan Root Bark + *Angelica Dahurica* Root + *Bupleurum* Root1:1:1(w:w:w) mixture extract | 10 | 5 | 38.05 ± 3.91 |
| | 30 | 5 | 21.24 ± 2.87 |

TABLE 58

Decrease of Iba-1 positive cells in hippocampus of LPS-induced Parkinson's disease mouse model by mixture extract of Moutan Root Bark, *Angelica Dahurica* Root and *Bupleurum* Root

| Treatment substance | Extract dose (mg/kg) | Inducer dose (LPS, mg/kg) | Iba-1-positive cell (% of control) |
|---|---|---|---|
| Normal control | — | — | 18.67 ± 5.44 |
| Negative control | — | 5 | 58.15 ± 4.76 |
| Moutan Root Bark + *Angelica Dahurica* Root + *Bupleurum* Root 1:1:1(w:w:w) mixture extract | 10 | 5 | 24.70 ± 3.31 |
| | 30 | 5 | 14.75 ± 3.08 |

Manufacturing Example 1: Preparation of Pharmaceutical Formulations

<1-1> Preparation of Powders

| | |
|---|---|
| Mixture extract of the invention or its fraction | 0.1 g |
| Lactose | 1.5 g |
| Talc | 0.5 g |

Powders were prepared by mixing all the above components, which were filled in airtight packs according to the conventional method for preparing powders.

<1-2> Preparation of Tablets

| | |
|---|---|
| Mixture extract of the invention or its fraction | 0.1 g |
| Lactose | 7.9 g |
| Crystalline cellulose | 1.5 g |
| Magnesium stearate | 0.5 g |

Tablets were prepared by mixing all the above components by the conventional direct tableting method.

<1-3> Preparation of Capsules

| | |
|---|---|
| Mixture extract of the invention or its fraction | 0.1 g |
| Corn starch | 5 g |
| Carboxy cellulose | 4.9 g |

Capsules were prepared by mixing all the above components, which were filled in hard capsules according to the conventional method for preparing capsules.

<1-4> Preparation of Injectable Solutions

| | |
|---|---|
| Mixture extract of the invention or its fraction | 0.1 g |
| Sterilized distilled water | proper amount |
| pH regulator | proper amount |

Injectable solutions were prepared by mixing all the above components, putting the mixture into 2 ml ampoules and sterilizing thereof by the conventional method for preparing injectable solutions.

<1-5> Preparation of Liquid Formulations

| | |
|---|---|
| Mixture extract of the invention or its fraction | 0.1 g |
| Isomerized sugar | 10 g |
| Mannitol | 5 g |
| Purified water | proper amount |

All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

Manufacturing Example 2: Preparation of Health Functional Foods

<2-1> Preparation of Flour Foods 0.5~5.0 weight part of the extract of the mixture of the present invention or the fraction thereof was added to the flour. Health enhancing foods such as bread, cake, cookies, crackers and noodles were prepared with the flour mixture according to the conventional method.

<2-2> Preparation of Soups and Gravies 0.1~5.0 weight part of the extract of the mixture of the present invention or the fraction thereof was added to soups and gravies. Health enhancing meat products, soups and gravies were prepared with this mixture by the conventional method.

<2-3> Preparation of Ground Beef

Health enhancing ground beef was prepared by mixing 10 weight part of the extract of the mixture of the present invention or the fraction thereof with ground beef according to the conventional method.

<2-4> Preparation of Ground Beef

5~10 weight part of the extract of the mixture of the present invention or the fraction thereof was added to milk. Health enhancing dairy products such as butter and ice cream were prepared with the milk mixture according to the conventional method.

<2-5> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The extract of the mixture of the present invention or the fraction thereof was concentrated under reduced pressure, spray-dried and pulverized to obtain 60-mesh dry powders.

Sun-Sik was prepared by mixing the dry powders of the grains, seeds and the extract of the mixture of the present invention or the fraction thereof according to the below ratio.

Grains (brown rice: 30 weight part, Yulmu: 15 weight part, barley: 20 weight part), Seeds (wild sesame: 7 weight part, black soybean: 8 weight part, black sesame: 7 weight part), The extract of the mixture of the present invention or the fraction thereof (3 weight part),

*Ganoderma lucidum* (0.5 weight part),

*Rehmannia glutinosa* (0.5 weight part)

<2-6> Preparation of Health Supplement Foods

| | |
|---|---|
| The extract of the mixture of the present invention or the fraction thereof | 100 mg |

| | |
|---|---|
| Vitamin complex | proper amount |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

Manufacturing Example 3: Preparation of Health Beverages

| | |
|---|---|
| The extract of the mixture of the present invention or the fraction thereof | 100 mg |
| Citric acid | 100 mg |
| Oligosaccharide | 100 mg |
| Maesil (*Prunus mume*) Extract | 2 mg |
| Taurine | 100 mg |
| Purified water | up to 500 ml |

The above constituents were mixed according to the conventional method for preparing health beverages. The mixture was heated at 85° C. for 1 hour with stirring and then filtered. The filtrate was loaded in 1 sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating a neurodegenerative disorder in a subject in need thereof comprising administering a composition consisting of an effective amount of an extract of a mixture of Moutan root bark (Moutan Radicis Cortex), Angelica dahurica root (Angelicae dahuricae radix) and Bupleurum root (Bupleuri radix) to said subject.

2. The method of claim 1, wherein the extract is obtained by using water, $C_1$~$C_4$ lower alcohol, or a mixture thereof.

3. The method of claim 2, wherein the lower alcohol is ethanol, methanol, or butanol.

4. The method of claim 1, wherein the extract comprises one or more compounds selected from the group consisting of paeonol (2'-Hydroxy-4'-methoxyacetophenone) represented by formula 1, paeoniflorin represented by formula 2;

paeoniflorigenone ([(2s,3as,5s,7ar,8s)-3a-hydroxy-7a-methyl-6-oxohexahydro-2,5-methano-1,3-benzodioxol-8-yl]methyl benzoate) represented by formula 3;

imperatorin (9-[(3-Methyl-2-buten-1-yl)oxy]-7h-furo[3,2-g][1]benzopyran-7-one) represented by formula 4;

saikosaponin A ((3beta,4alpha,16beta)-13,28-Epoxy-16,23-dihydroxyolean-11-en-3-yl-6-deoxy-3-O-beta-D-glucopyranosyl-beta-D-galactopyranoside) represented by formula 5;

saikosaponin B2 ((3b,4a,16a)-16,23,28-Trihydroxyoleana-11,13(18)-dien-3-yl-6-deoxy-3-O-beta-D-glucopyranosyl-beta-D-galactopyranoside) represented by formula 6;

saikosaponin B4 ((3β,11α,16α)-16,23,28-Trihydroxy-11-methoxyolean-12-en-3-yl-6-deoxy-3-O-β-D-glucopyranosyl-β-D-galactopyranoside) represented by formula 7; and saikosaponin D ((3b,4a,16a)-13,28-Epoxy-16,23-dihydroxyolean-11-en-3-yl 6-deoxy-3-O-beta-D-glucopyranosyl beta-D-galactopyranoside) represented by formula 8,

[Formula 1]

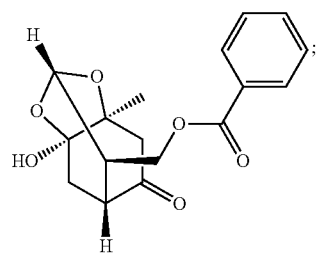

[Formula 2]

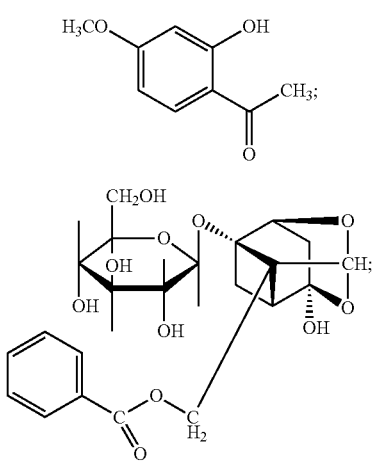

[Formula 3]

[Formula 4]

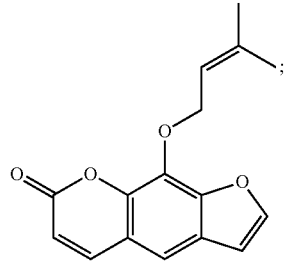

[Formula 5]

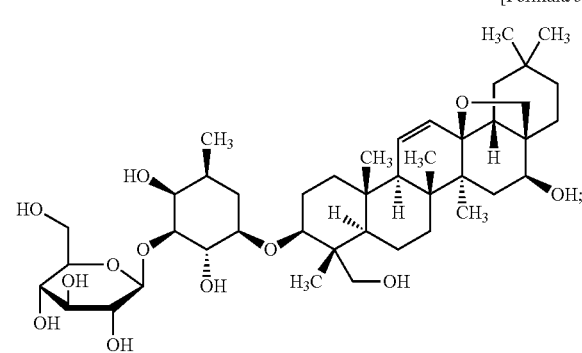

[Formula 6]

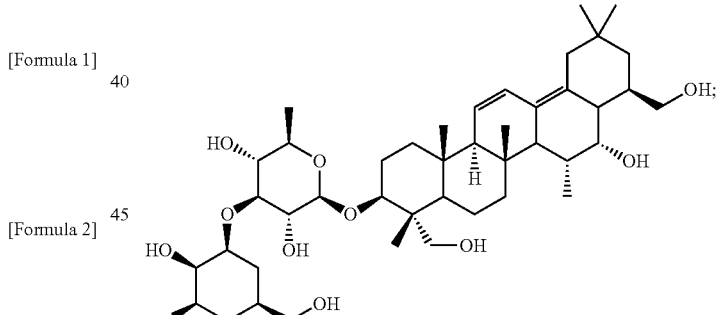

[Formula 7]

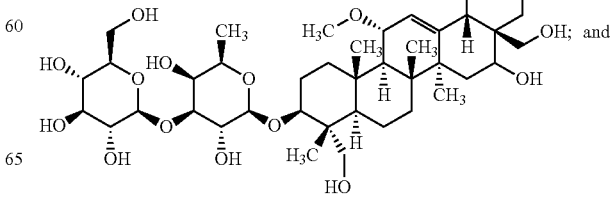

[Formula 8]

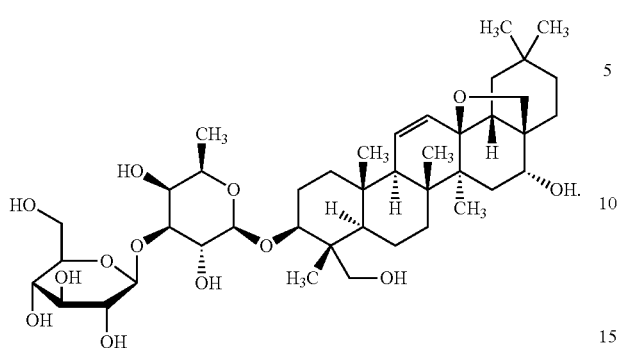

5. The method of claim 1, wherein the extract inhibits mitochondria functional damage, endoplasmic reticulum stress, or inflammatory response.

6. The method of claim 1, wherein the degenerative neurological disorder is selected from the group consisting of dementia, Huntington's disease, Parkinson's disease, Alzheimer's disease, stroke, Lou Gehrig's disease (amyotrophic lateral sclerosis), and spinal cord injury.

* * * * *